US006962613B2

(12) United States Patent
Jenson

(10) Patent No.: US 6,962,613 B2
(45) Date of Patent: Nov. 8, 2005

(54) LOW-TEMPERATURE FABRICATION OF THIN-FILM ENERGY-STORAGE DEVICES

(75) Inventor: Mark L. Jenson, Princeton, MN (US)

(73) Assignee: Cymbet Corporation, Elk River, MN (US)

( * ) Notice: Subject to any disclaimer, the term of this patent is extended or adjusted under 35 U.S.C. 154(b) by 237 days.

(21) Appl. No.: 09/815,919

(22) Filed: Mar. 23, 2001

(65) Prior Publication Data

US 2002/0001746 A1 Jan. 3, 2002

Related U.S. Application Data

(60) Provisional application No. 60/191,774, filed on Mar. 24, 2000, provisional application No. 60/225,134, filed on Aug. 14, 2000, and provisional application No. 60/238,673, filed on Oct. 6, 2000.

(51) Int. Cl.$^7$ ................................................ H01M 6/00
(52) U.S. Cl. ...................... 29/623.5; 427/523; 427/533; 427/529; 427/576; 429/231.95; 429/218.1; 117/92; 117/103; 117/902; 29/729; 29/730
(58) Field of Search .................... 117/92, 103, 902; 29/729, 730, 623.5; 427/523, 529, 533, 576, 577; 429/30, 33, 218.1, 231.8, 162; 204/192.22, 192.15; 438/238

(56) References Cited

U.S. PATENT DOCUMENTS

| | | | |
|---|---|---|---|
| 4,207,119 A | 6/1980 | Tyan | 136/89 TF |
| 4,299,890 A | 11/1981 | Rea et al. | 429/124 |
| 4,333,808 A | 6/1982 | Bhattacharyya et al. | 204/192 D |
| 4,353,160 A | 10/1982 | Armini et al. | 29/572 |
| 4,365,107 A | 12/1982 | Yamauchi | 136/258 |
| 4,435,445 A | 3/1984 | Allred et al. | |
| 4,440,108 A | 4/1984 | Little et al. | 118/719 |
| 4,481,265 A | 11/1984 | Ezawa et al. | 429/9 |
| 4,520,039 A | 5/1985 | Ovshinsky | 427/35 |
| 4,633,129 A | 12/1986 | Cuomo et al. | 313/153 |
| 4,645,726 A | 2/1987 | Hiratani et al. | 429/191 |
| 4,684,848 A | 8/1987 | Kaufman et al. | 315/111.81 |
| 4,696,671 A | 9/1987 | Epstein et al. | |
| 4,730,383 A | 3/1988 | Balkanski | 29/623.5 |
| 4,740,431 A | 4/1988 | Little | 429/9 |
| 4,832,463 A | 5/1989 | Goldner et al. | |
| 4,862,032 A | 8/1989 | Kaufman et al. | 313/359.1 |
| 5,017,550 A | 5/1991 | Shioya et al. | 505/1 |
| 5,022,930 A | 6/1991 | Ackerman et al. | 136/251 |
| 5,051,274 A | 9/1991 | Goldner et al. | 427/38 |
| 5,064,520 A | 11/1991 | Miyake et al. | 204/192.11 |
| 5,089,104 A | 2/1992 | Kanda et al. | 204/192.11 |
| 5,098,737 A | 3/1992 | Collins et al. | 427/53.1 |
| 5,115,378 A | 5/1992 | Tsuchiya et al. | 361/502 |
| 5,151,848 A | 9/1992 | Finello | 361/502 |
| 5,171,413 A | 12/1992 | Arntz et al. | 204/192.15 |
| 5,180,645 A | 1/1993 | More | 429/127 |
| 5,189,550 A | 2/1993 | Goldner et al. | 359/273 |
| 5,192,947 A | 3/1993 | Neustein | 340/825.44 |
| 5,202,196 A | 4/1993 | Wang et al. | 429/86 |
| 5,261,968 A | 11/1993 | Jordan | 136/244 |
| 5,273,837 A | 12/1993 | Aitken et al. | 249/30 |
| 5,296,122 A | 3/1994 | Katsube et al. | 204/298.04 |
| 5,314,765 A | 5/1994 | Bates | 429/194 |
| 5,338,625 A | 8/1994 | Bates et al. | 429/193 |
| 5,348,703 A | 9/1994 | Bishop et al. | 420/590 |
| 5,393,572 A | 2/1995 | Dearnaley | 427/523 |
| 5,411,592 A | 5/1995 | Ovshinsky et al. | 118/718 |
| 5,425,966 A | 6/1995 | Winter et al. | 427/255.1 |
| 5,426,561 A | 6/1995 | Yen et al. | 361/502 |
| 5,433,096 A | 7/1995 | Janssen et al. | 70/278 |
| 5,445,126 A | 8/1995 | Graves, Jr. | |
| 5,445,906 A | 8/1995 | Hobson et al. | 429/162 |
| 5,448,110 A | 9/1995 | Tuttle et al. | 257/723 |
| 5,449,994 A | 9/1995 | Armand et al. | 320/14 |
| 5,455,126 A | 10/1995 | Bates et al. | 429/127 |
| 5,468,521 A | 11/1995 | Kanai et al. | 427/575 |
| 5,482,611 A | 1/1996 | Helmer et al. | 204/298.17 |
| 5,501,175 A | 3/1996 | Tanaka et al. | 117/108 |
| 5,501,924 A | 3/1996 | Swierbut et al. | 429/224 |
| 5,510,209 A | 4/1996 | Abraham et al. | |

(Continued)

FOREIGN PATENT DOCUMENTS

| | | | | |
|---|---|---|---|---|
| DE | 19948742 | 12/2000 | | H01G/9/058 |
| EP | 0078404 | 5/1983 | | H01M/14/00 |
| EP | 0410627 | 1/1991 | | C23C/14/08 |

(Continued)

OTHER PUBLICATIONS

Dobley, Arthur, et al., "High Capacity Cathodes for Lithium–Air Batteries", Yardney Technical Products, Inc./ Lithion, Inc. Pawcatuck, CT <http://www2.electrochem.org/cgi–bin/abs?mtg=206&abs=0496>.

Lugscheider, E. , et al., "Comparison of the Structure of PVD–Thin Films Deposited With Different Deposition Energies", *Surface and Coatings Technology*, 86–87 (1–3), (Dec. 1, 1996),177–183.

McKenzie, D. R., et al., "New Technology for PACVD", *Surface and Coatings Technology*, 82 (3), (1996),326–333, no month available.

(Continued)

*Primary Examiner*—Bruce F. Bell
(74) *Attorney, Agent, or Firm*—Charles A. Lemaire; Lemaire Patent Law Firm, P.L.L.C.

(57) ABSTRACT

A method and system for fabricating solid-state energy-storage devices including fabrication films for devices without an anneal step, especially a cathode anneal of thin-film batteries. A film of an energy-storage device is fabricated by depositing a first material layer to a location on a substrate. Energy is supplied directly to the material forming the film. The energy can be in the form of energized ions of a second material. Supplying energy directly to the material and/or the film being deposited assists the growth of the crystalline structure of film. For lithium-ion energy-storage devices, the first material is an intercalation material, which releasably stores lithium ions therein. Supercapacitors and energy-conversion devices are also fabricated according the methods.

107 Claims, 46 Drawing Sheets

U.S. PATENT DOCUMENTS

| | | | |
|---|---|---|---|
| 5,512,147 A | 4/1996 | Bates et al. ............ 204/192.15 |
| 5,528,222 A | 6/1996 | Moskowitz et al. ........ 340/572 |
| 5,529,671 A | 6/1996 | Debley et al. .......... 204/192.34 |
| 5,536,333 A | 7/1996 | Foote et al. ................ 136/260 |
| 5,549,989 A | 8/1996 | Anani ........................ 429/193 |
| 5,558,953 A | 9/1996 | Matsui et al. ............... 429/194 |
| 5,561,004 A | 10/1996 | Bates et al. ................. 429/162 |
| 5,567,210 A | 10/1996 | Bates et al. ................. 29/623.5 |
| 5,569,520 A | 10/1996 | Bates ......................... 429/162 |
| 5,569,564 A | 10/1996 | Swierbut et al. ............ 424/224 |
| 5,571,749 A | 11/1996 | Matsuda et al. ............ 437/113 |
| 5,585,999 A | 12/1996 | De Long et al. ............ 361/505 |
| 5,593,551 A | 1/1997 | Lai ....................... 204/192.12 |
| 5,597,660 A | 1/1997 | Bates et al. ................. 429/191 |
| 5,599,644 A | 2/1997 | Swierbut et al. ............ 429/224 |
| 5,601,652 A | 2/1997 | Mullin et al. .......... 118/723 EB |
| 5,612,152 A | 3/1997 | Bates ........................ 429/152 |
| 5,626,976 A | 5/1997 | Blanton et al. ................ 429/9 |
| 5,644,207 A | 7/1997 | Lew et al. .................... 320/5 |
| 5,654,084 A | 8/1997 | Egert ......................... 428/215 |
| 5,695,873 A | 12/1997 | Kumar et al. ................ 428/325 |
| 5,695,885 A | 12/1997 | Malhi ........................... 429/7 |
| 5,705,293 A | 1/1998 | Hobson ....................... 429/162 |
| 5,714,404 A | 2/1998 | Mitlitsky et al. |
| 5,763,058 A | 6/1998 | Isen et al. ................... 428/209 |
| 5,830,331 A | 11/1998 | Kim et al. .............. 204/192.15 |
| 5,863,337 A | 1/1999 | Neuman et al. ............ 118/718 |
| 5,868,914 A | 2/1999 | Landsbergen et al. . 204/298.06 |
| 5,872,080 A | 2/1999 | Arendt et al. ............... 505/238 |
| 5,914,507 A | 6/1999 | Polla et al. ................. 257/254 |
| 5,935,727 A | 8/1999 | Chiao .......................... 429/32 |
| 5,953,677 A | 9/1999 | Sato .......................... 455/574 |
| 5,978,207 A | 11/1999 | Anderson et al. ............ 361/311 |
| 5,981,107 A | 11/1999 | Hamano et al. ....... 429/231.95 |
| 5,995,006 A | 11/1999 | Walsh ..................... 340/572.7 |
| 6,001,715 A | 12/1999 | Manka et al. |
| 6,002,208 A | 12/1999 | Maishev et al. .......... 315/111.9 |
| 6,023,610 A | 2/2000 | Wood, Jr. |
| 6,033,471 A | 3/2000 | Nakanishi et al. .......... 117/108 |
| 6,037,717 A | 3/2000 | Maishev et al. ........ 315/111.91 |
| 6,042,687 A | 3/2000 | Singh et al. ................. 156/345 |
| 6,056,857 A * | 5/2000 | Hunt et al. ............ 204/192.15 |
| 6,059,847 A | 5/2000 | Farahmandi et al. ....... 29/25.03 |
| 6,077,621 A * | 6/2000 | Allen et al. ................... 429/33 |
| 6,078,791 A | 6/2000 | Tuttle et al. |
| 6,086,962 A * | 7/2000 | Mahoney et al. ............ 427/577 |
| 6,094,292 A | 7/2000 | Goldner et al. ............. 359/265 |
| 6,103,412 A | 8/2000 | Hirano et al. ................. 429/24 |
| 6,110,620 A | 8/2000 | Singh et al. ................. 429/223 |
| 6,130,507 A | 10/2000 | Maishev et al. ........ 315/111.81 |
| 6,133,159 A | 10/2000 | Vaartstra et al. ............ 438/758 |
| 6,136,165 A | 10/2000 | Moslehi ................. 204/298.06 |
| 6,139,964 A | 10/2000 | Sathrum et al. ............ 428/408 |
| 6,147,354 A | 11/2000 | Maishev et al. ......... 250/423 R |
| 6,153,067 A | 11/2000 | Maishev et al. ....... 204/298.04 |
| 6,181,237 B1 | 1/2001 | Gehlot |
| 6,181,545 B1 | 1/2001 | Amatucci et al. ........... 361/502 |
| 6,203,944 B1 * | 3/2001 | Turner et al. ............. 429/218.1 |
| 6,222,117 B1 | 4/2001 | Shiozaki ..................... 136/256 |
| 6,236,061 B1 | 5/2001 | Walpta ........................ 257/40 |
| 6,238,813 B1 | 5/2001 | Maile et al. ................... 429/9 |
| 6,277,523 B1 | 8/2001 | Giron ......................... 429/304 |
| 6,280,875 B1 | 8/2001 | Kwak et al. ................ 429/162 |
| 6,294,722 B1 | 9/2001 | Kondo et al. |
| 6,327,909 B1 | 12/2001 | Hung et al. .............. 73/514.16 |
| 6,391,664 B1 | 5/2002 | Goruganthu et al. |
| 6,402,796 B1 | 6/2002 | Johnson |
| 6,432,577 B1 | 8/2002 | Shul et al. .................. 429/162 |
| 6,475,854 B2 * | 11/2002 | Narwankar et al. ......... 438/238 |
| 6,558,836 B1 | 5/2003 | Whitacre et al. ........... 429/162 |
| 6,576,369 B1 * | 6/2003 | Moriguchi et al. ...... 429/231.8 |
| 6,599,580 B2 * | 7/2003 | Muffoletto et al. ......... 427/454 |
| 6,608,464 B1 | 8/2003 | Lew et al. |
| 6,610,971 B1 | 8/2003 | Crabtree ..................... 244/3.1 |
| 6,634,232 B1 | 10/2003 | Rettig et al. ............. 73/514.15 |
| 6,645,656 B1 * | 11/2003 | Chen et al. ................... 429/32 |
| 6,741,178 B1 | 5/2004 | Tuttle |
| 2001/0014398 A1 | 8/2001 | Veerasamy .................. 428/408 |
| 2001/0051300 A1 | 12/2001 | Moriguchi et al. ...... 429/231.8 |
| 2002/0076616 A1 | 6/2002 | Lee et al. .................... 429/300 |

FOREIGN PATENT DOCUMENTS

| | | | |
|---|---|---|---|
| EP | 0643544 | 8/1994 | ............ H04Q/7/32 |
| EP | 0860888 | 8/1998 | ............ H01M/8/10 |
| EP | 0867752 | 9/1998 | ............ G02F/1/15 |
| GB | 2318127 | 4/1998 | ........... C23C/14/06 |
| JP | 58126679 | 8/1983 | .......... H01M/10/40 |
| JP | 57230095 | 7/1984 | |
| JP | 59123236 | 7/1984 | |
| JP | 60012679 | 1/1985 | .......... H01M/10/36 |
| JP | 60182961 | 2/1987 | |
| JP | 62044960 | 2/1987 | .......... H01M/10/38 |
| JP | 63166151 | 1/1990 | |
| JP | 03205757 | 9/1991 | ............ H01M/2/10 |
| JP | 03262697 | 11/1991 | ............ B42D/15/10 |
| JP | 06067018 | 3/1994 | ............ G02B/5/28 |
| JP | 6111828 | 4/1994 | ............ H01M/4/86 |
| JP | 6196178 | 7/1994 | |
| JP | 06223805 | 8/1994 | ............ H01M/2/22 |
| JP | 07006933 | 1/1995 | ............ H01G/9/00 |
| JP | 07-050229 | 2/1995 | .......... H01G/9/028 |
| JP | 07057739 | 3/1995 | ............ H01M/4/88 |
| JP | 08017179 | 1/1996 | ............ G11B/33/12 |
| JP | 08293310 | 5/1996 | ............ H01M/8/02 |
| JP | 08236105 | 9/1996 | ............ H01M/4/04 |
| JP | 08287901 | 11/1996 | ............ H01M/4/04 |
| JP | 09035233 | 2/1997 | ............ G11B/5/66 |
| JP | 09211204 | 8/1997 | ............ G02B/1/11 |
| JP | 10021896 | 1/1998 | ............ H01M/2/22 |
| JP | 10021933 | 1/1998 | ............ H01M/4/86 |
| JP | 2000188113 | 7/2000 | ............ H01M/6/18 |
| WO | WO-99/33124 | 7/1990 | ............ H01M/2/10 |
| WO | WO-92/15140 | 9/1992 | ............ H02J/7/00 |
| WO | WO-92/16025 | 9/1992 | ............ H01M/2/22 |
| WO | WO-92/19090 | 10/1992 | ............ H05K/1/16 |
| WO | WO-93/14612 | 7/1993 | ............ H05K/1/00 |
| WO | WO-95/14311 | 5/1995 | ............ H01M/6/18 |
| WO | WO-97/38453 | 10/1997 | ............ H01M/2/02 |
| WO | WO-97/39491 | 10/1997 | .......... H01M/10/44 |
| WO | WO-98/13743 | 4/1998 | ............ G06F/1/26 |
| WO | WO-98/47196 | 10/1998 | ............ H01M/4/58 |
| WO | WO-99/25908 | 5/1999 | .......... C30B/23/02 |

OTHER PUBLICATIONS

Shukla, A. K., et al., "Electrochemical supercapacitors: Energy storage beyond batteries", *Current Science*, vol. 79, No. 12, (Dec. 25, 2000),1656–1661.

Aramoto, T., et al., "16.0% Efficient Thin–Film CdS/CdTe Solar Cells", *Jpn. J. Appl. Phys., vol. 36, Pt. 1, No. 10*, pp. 6304–6305, (1997).

Birkmire, R.W., et al., "Polycrystalline Thin Film Solar Cells: Present Status and Future Potential", *Annu. Rev. Mater. Sci., 27*, pp. 625–653, (1997).

Chu, T.L., et al., "13.4% efficient thin–film CdS/CdTe solar cells", *J. Appl. Phys., 70*(12), pp. 7608–7612, (Dec. 15, 1991).

Dudney, N.J., et al., "Nanocrystalline $Li_xMn_{2-y}O_4$ Cathodes for Solid–State Thin–Film Rechargeable Lithium Batteries", *Journal of the Electrochemical Society*, 146(7), pp. 2455–2464, (1999).

Jacobson, A.J., "Intercalation Chemistry", *In: Encyclopedia of Inorganic Chemistry, vol. 3*, R.B. King, ed., John Wiley & Sons, pp. 1556–1602, (1994).

Yoshida, T., "Photovoltaic Properties of Screen–Printed CdTe/CdS Solar Cells on Indium–Tin–Oxide Coated Glass Substrates", *J. Electrochem. Soc.*, 142 (9), pp. 3232–3237, (Sep. 1995).

Dunn, D., et al., "MoS2 Deposited by ion beam assisted deposition: 2H or random layer structure.", *Naval Research Laboratory*, (1998),pp. 3001–3007.

Goldner, R., "Ambient temperature synthesis of polycrystalline thin films of lithium cobalt oxide with controlled crystallites orientations", *Electrochemical Soc. Proceedings, 98*, (1999),pp. 268–273.

Goldner, R., et al., "Ambient Temperature Synthesis of Polycrystalline Thin Films of Lithium Cobalt Oxide with Controlled Crystallites' Orientation", *Mat. Res. Soc. Symp. Proc., 548*, (1998),pp. 131–136.

Kyokane, J., et al., "Organic Solid Capacitor with Conducting Thin Films as Elecrolyte by Ion–Beam–Assisted Deposition", *Journal of Power Sources, 60*, (1996),pp. 151–155.

Liu, W., et al., "Deposition, Structural Characterization, and Broadband (1KHz–40GHz) Dielectri Behavior of BaxTi2-xOy Thin Films", *Mat. Res. Soc. Symp. Proc., 310*, (1993),pp. 157–162.

Martin, P., et al., "Modification of the optical and structural properties of dielectric ZrO2 films by ion–assisted deposition", *Journal of Applied Physics, 55*(1), (1984),pp. 235–241.

Nomoto, S., et al., "Back–up Performance of Electric Double–Layer Capacitors for Rechargeable Batteries", *Electrochemical Society Proceedings*, vol. 96–25,(1997),268–279.

Shodai, T, et al., "Reaction Mechanisms of Li(2.6)Co(0.4) Anode Material", *Solid State Ionics*, 122,(1999),85–93.

Vereda, F., "A study of electronic shorting in IBDA–deposited Lipon films", *Journal of Power Sources, 89*(2), (2000),pp. 201–205.

Zeitler, M., et al., "In Situ Stress Analysis of Boron Nitride Films Prepared by Ion Beam Assisted Deposition", *Nuclear Instruments and Methods in Physics Research B, 139*, (1998),pp. 327–331.

* cited by examiner

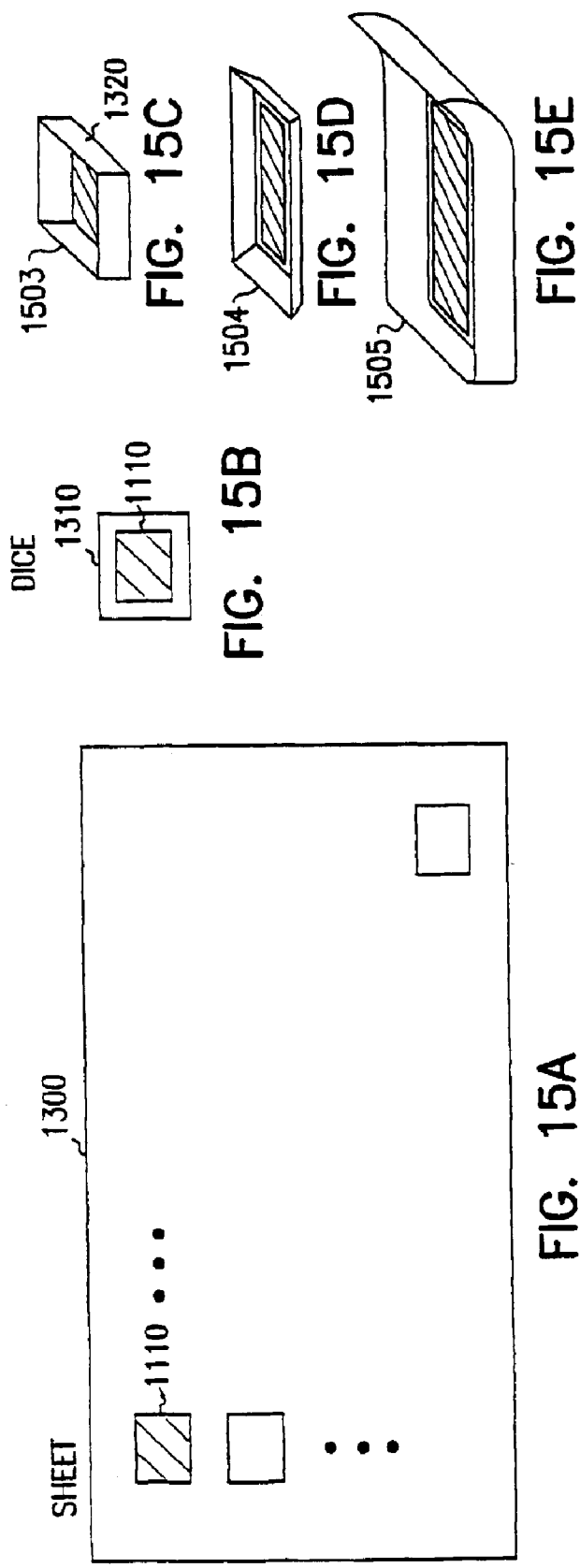

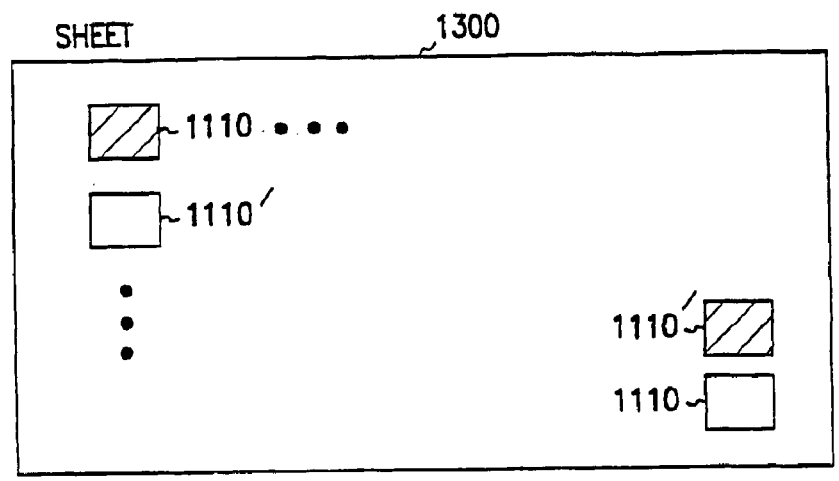
FIG. 15I
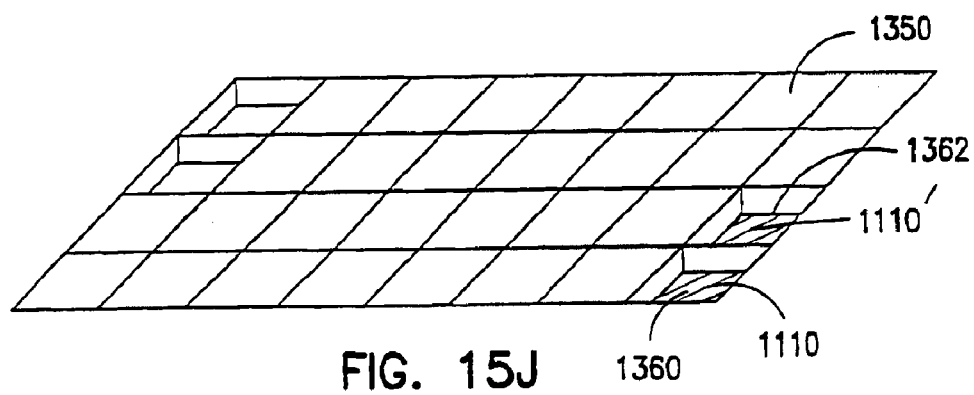
FIG. 15J
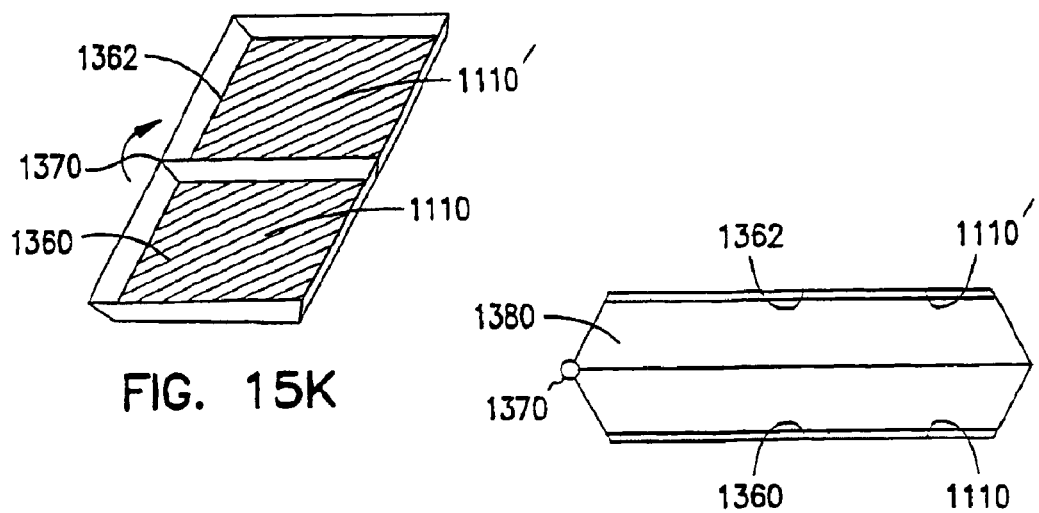
FIG. 15K
FIG. 15L

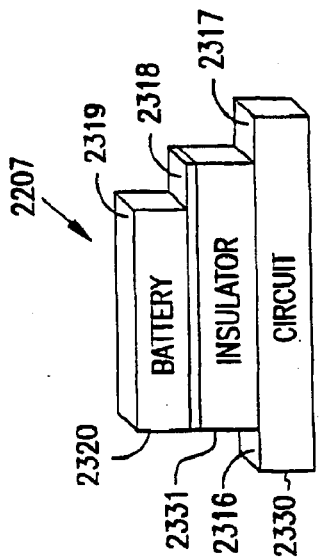
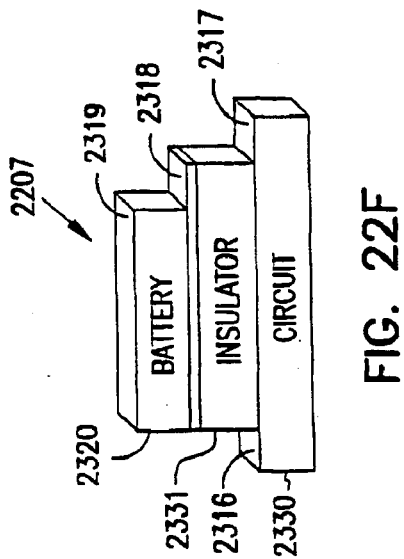
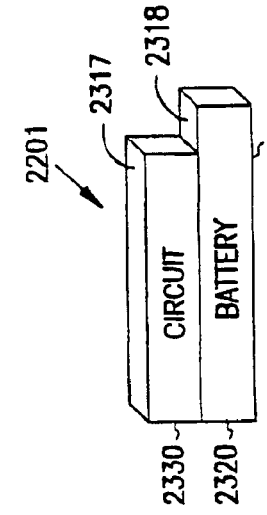
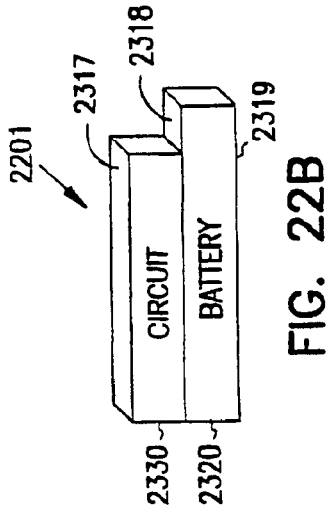
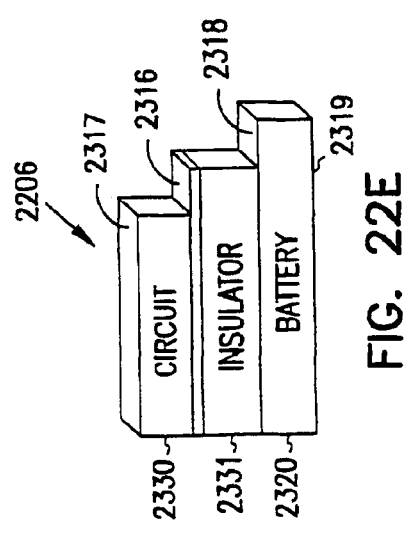
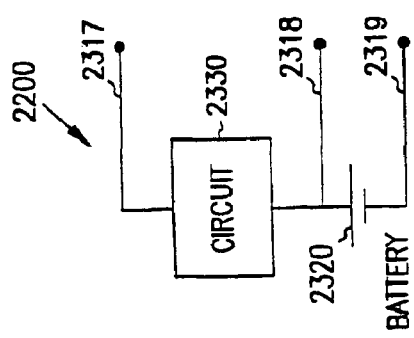

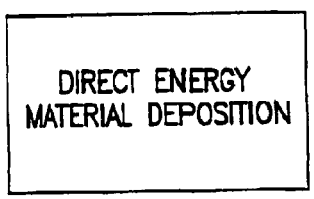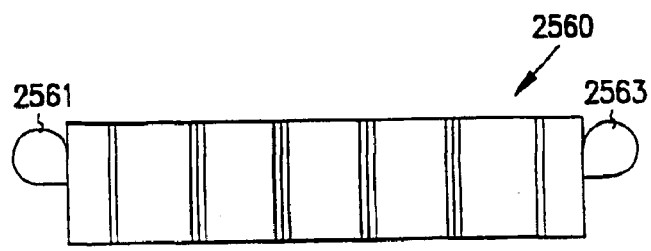
FIG. 25F
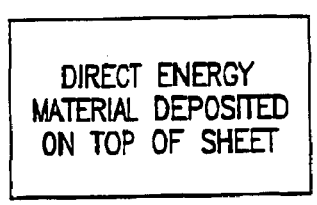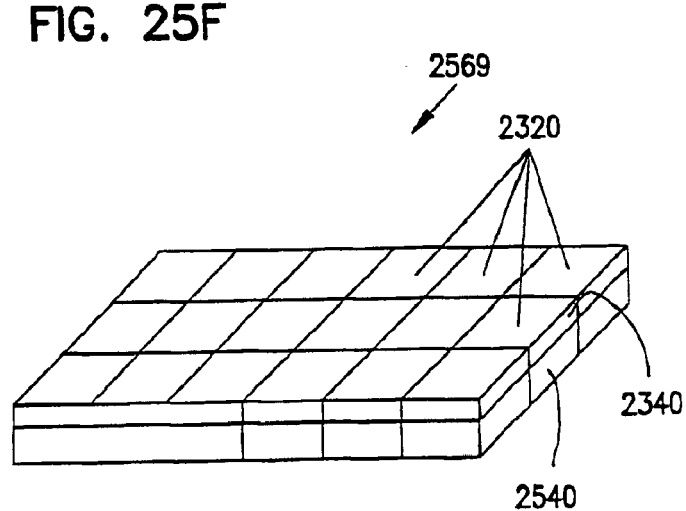
FIG. 25G

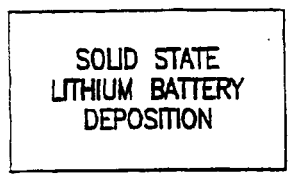
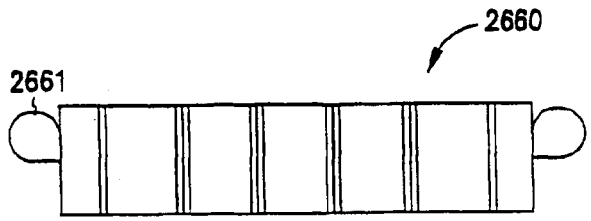
FIG. 26B
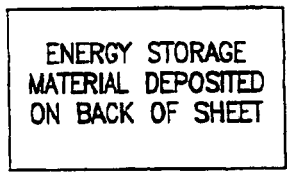
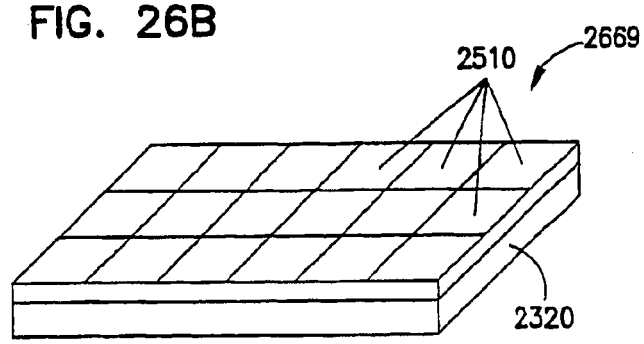
FIG. 26C
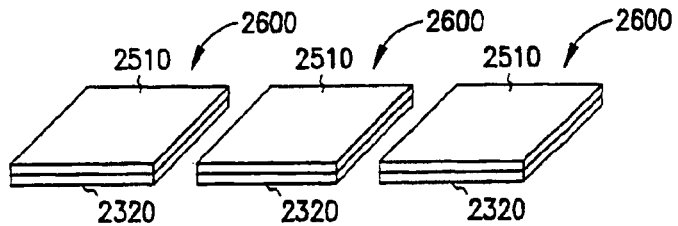
FIG. 26D
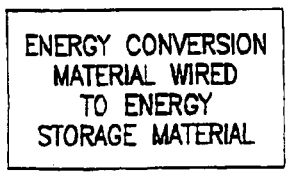
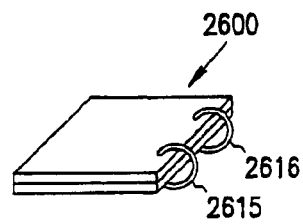
FIG. 26E
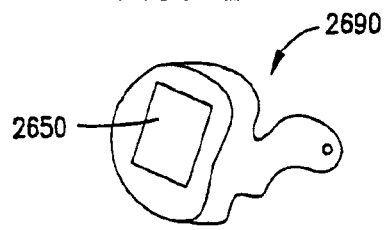
FIG. 26F

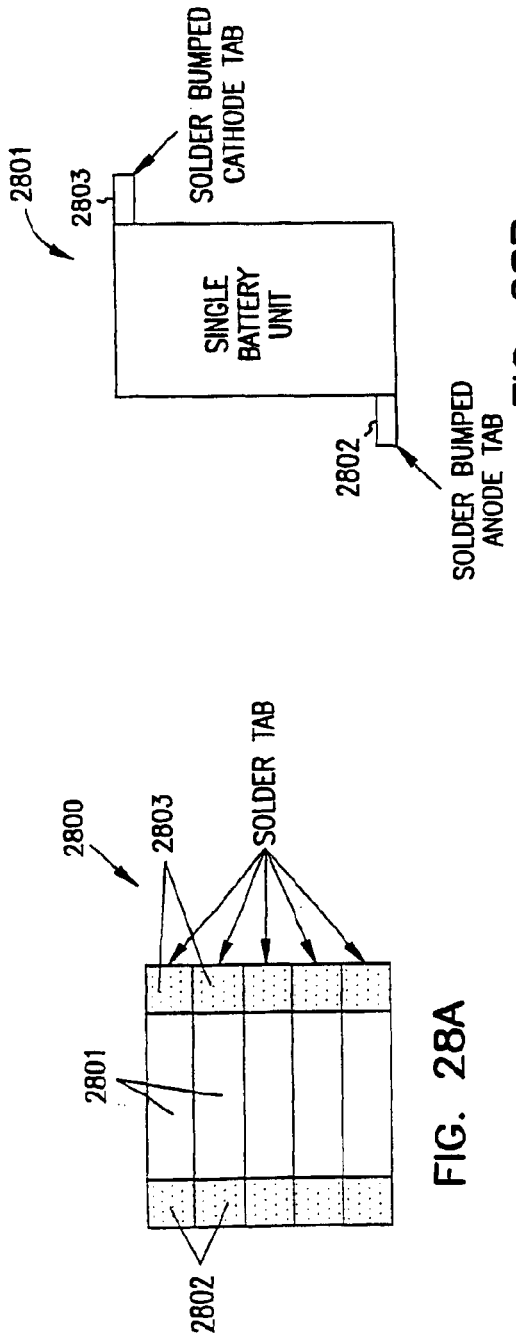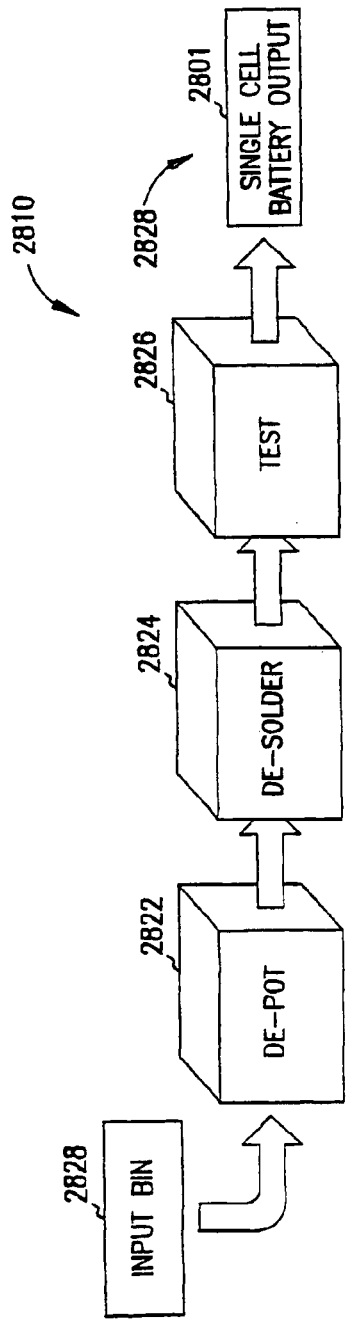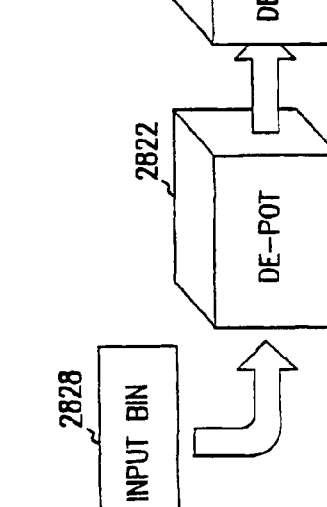

LOW-TEMPERATURE FABRICATION OF THIN-FILM ENERGY-STORAGE DEVICES

CROSS-REFERENCES TO RELATED INVENTIONS

This invention claims priority to the following three provisional U.S. patent applications: Ser. No. 60/191,774, filed: Mar. 24, 2000, titled "Comprehensive Patent for the Fabrication of a High Volume, Low Cost Energy Products Such as Solid State Lithium Ion Rechargeable Battery, Supercapacitors and Fuel Cells," Ser. No. 60/225,134, filed: Aug. 14, 2000, titled "Apparatus and Method for Rechargable Batteries and for Making and Using Batteries" and Ser. No. 60/238,673, filed: Oct. 6, 2000, Titled "Battery Having Ultrathin Electrolyte," each of which is incorporated by reference.

This invention also is related to patent applications for the following six attorney dockets each filed on even date herewith: Ser. No. 09/815,983 titled "Thin-Film Battery Having Ultra-Thin Electrolyte and Associated Method," Ser. No. 10/693,817 titled "Integrated Capacitor-Like Battery and Associated Method," Ser. No. 09/816,628 titled "Method and Apparatus for Integrated-Battery Devices," Ser. No. 09/816,603 titled "Continuous Processing of Thin-Film Batteries and Like Devices," Ser. No. 09/816,602 titled "Device Enclosures and Devices with Integrated Battery," and Ser. No. 09/815,884 titled "Battery-Operated Wireless-Communication Apparatus and Method," each of which is incorporated by reference.

FIELD OF THE INVENTION

The present invention relates to solid-state energy-storage devices. More particularly, this invention relates to methods and systems for fabricating solid-state energy-storage devices and the resulting devices such as batteries and supercapacitors. The present invention also relates to solid-state energy-conversion devices, such as photovoltaics and fuel cells, and associated methods.

BACKGROUND OF THE INVENTION

Electronics have been incorporated into many portable devices such as computers, mobile phones, tracking systems, scanners, etc. One drawback to portable devices is the need to include the power supply with the device. Portable devices typically use batteries as power supplies. Batteries must have sufficient capacity to power the device for at least the length of time the device is in use. Sufficient battery capacity can result in a power supply that is quite heavy or large compared to the rest of the device. Accordingly, smaller and lighter batteries (i.e., power supplies) with sufficient energy storage are desired. Other energy storage devices, such as supercapacitors, and energy conversion devices, such as photovoltaics and fuel cells, are alternatives to batteries for use as power supplies in portable electronics and non-portable electrical applications.

Another drawback of conventional batteries is the fact that some are fabricated from potentially toxic materials that may leak and be subject to governmental regulation. Accordingly, it is desired to provide an electrical power source that is safe, solid-state and rechargeable over many charge/discharge life cycles.

One type of an energy-storage device is a solid-state, thin-film battery. Examples of thin-film batteries are described in U.S. Pat. Nos. 5,314,765; 5,338,625; 5,445,126; 5,445,906; 5,512,147; 5,561,004; 5,567,210; 5,569,520; 5,597,660; 5,612,152; 5,654,084; and 5,705,293, each of which is herein incorporated by reference. U.S. Pat. No. 5,338,625 describes a thin-film battery, especially a thin-film microbattery, and a method for making same having application as a backup or first integrated power source for electronic devices. U.S. Pat. No. 5,445,906 describes a method and system for manufacturing a thin-film battery structure formed with the method that utilizes a plurality of deposition stations at which thin battery component films are built up in sequence upon a web-like substrate as the substrate is automatically moved through the stations.

FIG. 1A shows a prior art thin-film battery 20 formed on substrate 22. The battery includes a cathode current collector 32 and an anode current collector 34 formed on the substrate 22. A cathode layer 38 is formed on the cathode current collector 32. An electrolyte layer 42 is formed on the cathode layer 38. An anode layer 44 is formed on the electrolyte layer 42, the substrate 22 and the anode current collector 34. The current collectors 32 and 34 are connected to external circuitry to provide electrical power to the same. In a discharge operation, ions in the anode layer 44 travel through the electrolyte layer 42 and are stored in the cathode layer 38. Thereby, creating current flowing from the anode current collector 34 to the cathode current collector 32. In a charge operation, an external electrical charge is applied to the current collectors 32 and 34. Thereby, ions in the cathode layer 38 are forced to travel through the electrolyte layer 42 and are stored in the anode layer 44.

FIG. 2A shows a prior art method for fabricating the thin-film battery 20. First, the substrate is prepared for deposition of the thin-film battery (step 215). The cathode current collector is deposited on the substrate using DC-magnetron sputtering (step 217). The cathode is deposited on the cathode current collector by RF-magnetron sputtering (step 219). In this method, the magnetron source provides sputtered material having energy of about 1–3 eV, which is insufficient to crystallize the cathode material to form desirable crystal structures that encourage ion movement into and out of the cathode material. The cathode must be annealed to produce a crystalline lattice structure in the cathode, which is necessary to produce an energy-storage device that has the required electrical performance characteristics. In some embodiments, a desired electrical characteristic of a battery is a discharge curve that has a relatively constant voltage (small delta) over a range of capacity and then the voltage decreases rapidly as remaining capacity is exhausted (large delta). Accordingly, the stack of the substrate, cathode current collector and the cathode are annealed at a temperature of 700 degrees Celsius (step 221 of FIG. 2A). The anneal step 221 complicates and adds cost to the fabrication of this type of solid-state battery. Further, the anneal step 221 precludes the use of any material as the substrate or other part of the battery thus formed that is unable to withstand the high anneal temperature. The anode current collector is deposited on the substrate by DC-magnetron sputtering (step 223). The electrolyte layer is deposited by RF-magnetron sputtering (step 225). The anode is deposited by thermal evaporation (step 227).

Accordingly, there is a need for solid-state energy-storage devices, e.g., thin-film batteries and capacitors, that can be rapidly fabricated and that have acceptable electrical properties for use in a variety of electrical devices. More specifically, there is a need for a fabrication method and system that does not require a high-temperature anneal to form a solid-state energy-storage device.

SUMMARY OF THE INVENTION

A method and system is described for fabricating solid-state energy-storage devices. Some embodiments include fabricating films for an energy-storage device without an anneal step, especially without a cathode anneal. The present invention provides energy focused at the location where it is needed to form a film having certain structural characteristics. Accordingly, the total energy applied to the film and its support is less than if the energy was applied to the entire device, e.g., high temperature annealing the entire device. Thus, the present invention provides methods for applying energy to cure defects and/or create desired crystal structure at the time of depositing a film. In some embodiments, the energy is applied essentially at a few atomic layers at a time during deposition of a film.

In an embodiment as described herein, a film of an energy-storage device is fabricated by depositing a first material layer to a location on a substrate. Energized ions of a second material are directed to the first material to supply energy thereto, thereby assisting the growth of the crystalline structure of the first material. In some embodiments, the first material includes an intercalation material, which releasably stores ions therein. In one embodiment, the intercalation material is a lithium intercalation material. In energy-storage devices, and specifically in thin-film batteries, it is desirable to have large crystal size and a specific crystal orientation to improve electrical characteristics of the energy-storage device.

Another aspect of the invention includes fabricating a layer of an energy-storage device using a first source for supplying component material for the layer and a second source for supplying energy to a location on the substrate at which the layer is to be deposited. In one embodiment, the fabricated layer is the cathode for a thin-film battery. In another embodiment, the thin-film battery is a rechargeable, solid-state lithium-ion battery.

Another feature of the present invention is fabricating the electrolyte film by depositing a first material layer to a location on a substrate. Energized ions of a second material are directed to supply energy to the first material, thus assisting the growth of the crystalline structure of the first material. Another feature of the present invention includes fabricating the anode film by depositing a first intercalation material layer to a location on a substrate. Energized ions of a second material are directed to supply energy to the first material, thereby assisting the growth of the crystalline structure of the first material and controlling stoichiometry of the crystalline structure of the first material.

Another aspect of the present invention includes controlling the energy provided by the second source energized ions. The energized ions provide energy to the intercalation material of about 5 eV or greater.

It is yet another aspect of the present invention to provide a seed layer on which an intercalation film is grown. The seed layer assists the formation of desired crystal structures to improve energy-storage device performance.

Another feature of the present invention includes fabricating an energy-storage device on any one of a plurality of different substrates. Some of the substrates have thermal degradation temperatures that are less than temperatures used for processes conventionally used for making thin-film batteries. It is another feature to provide systems and fabrication techniques that do not cause temperature degradation of a substrate or other layers thereon.

It is an aspect of the present invention to fabricate energy-storage devices under economical manufacturing conditions.

BRIEF DESCRIPTION OF THE DRAWINGS

FIG. 15A is a plan view of a sheet including a plurality of battery cells.

FIG. 15B is a plan view of a diced battery cell before forming.

FIG. 15C is a perspective view of a battery cell after forming.

FIG. 15D is a perspective view of a battery cell after forming.

FIG. 15E is a perspective view of a battery cell after forming.

FIG. 15I is a plan view of a sheet including a plurality of battery cells.

FIG. 15J is a perspective view of a sheet including a plurality of battery cells formed on the sheet according to this invention.

FIG. 15K is a perspective view of a sheet including two battery cells formed into a case from the sheet shown in FIG. 15J according to this invention.

FIG. 15L is a side view of an electronic device enclosure formed from a sheet.

FIG. 22A shows a schematic circuit of an embodiment of an integrated battery and circuit sharing a common terminal.

FIG. 22B shows a block diagram perspective view of an integrated device implementing the circuit of FIG. 22A having the circuit built on the battery.

FIG. 22C shows a block diagram perspective view of an integrated device implementing the circuit of FIG. 22A having the battery built on the circuit.

FIG. 22D shows a schematic circuit of an embodiment 2202 of an integrated battery and circuit each having separate terminals.

FIG. 22E shows a block diagram perspective view of an integrated device implementing the circuit of FIG. 22D having the circuit built on the battery.

FIG. 22F shows a block diagram perspective view of an integrated device implementing the circuit of FIG. 22D having the battery built on the circuit.

FIG. 25F shows a block diagram of a layer-deposition system 2560.

FIG. 25G shows a perspective view of a processed sheet 2569.

FIG. 26B shows a block diagram of a layer-deposition system 2660.

FIG. 26C shows a perspective view of a processed sheet 2669.

FIG. 26D shows a perspective view of diced final devices 2600.

FIG. 26E shows a perspective view of wired diced final device 2600.

FIG. 26F shows a perspective view of a hearing aid 2690 incorporating a wired diced final device 2600.

FIG. 28A shows an elevation view of a battery 2800 having stacked cells.

FIG. 28B shows a plan view of a single battery cell after recycling.

FIG. 28C shows a process 2810 used for recycling.

In the drawings, like numerals describe substantially similar components throughout the several views. Signals and connections may be referred to by the same reference number, and the meaning will be clear from the context of the description.

DETAILED DESCRIPTION

In the following detailed description of the preferred embodiments, reference is made to the accompanying drawings that form a part hereof, and in which are shown, by way of illustration, specific embodiments in which the invention may be practiced. It is to be understood that other embodiments may be utilized and structural changes may be made without departing from the scope of the present invention.

It is to be understood that in different embodiments of the invention, each battery in the Figures or the description can be implemented using one or more cells, and if a plurality of cells is implemented, the cells can be wired in parallel or in series. Thus, where a battery or more than one cell is shown or described, other embodiments use a single cell, and where a single cell is shown or described, other embodiments use a battery or more than one cell. Further, the references to relative terms such as top, bottom, upper, lower, etc. refer to an example orientation such as used in the Figures, and not necessarily an orientation used during fabrication or use.

The terms wafer and substrate as used herein include any structure having an exposed surface onto which a film or layer is deposited, for example, to form an integrated circuit (IC) structure or an energy-storage device. The term substrate is understood to include semiconductor wafers, plastic film, metal foil, and other structures on which an energy-storage device may be fabricated according to the teachings of the present disclosure. The term substrate is also used to refer to structures during processing that include other layers that have been fabricated thereupon. Both wafer and substrate include doped and undoped semiconductors, epitaxial semiconductor layers supported by a base semiconductor or insulator, as well as other semiconductor structures well known to one skilled in the art. Substrate is also used herein as describing any starting material that is useable with the fabrication method as described herein.

The term battery used herein refers to one example of an energy-storage device. A battery may be formed of a single cell or a plurality of cells connected in series or in parallel. A cell is a galvanic unit that converts chemical energy, e.g., ionic energy, to electrical energy. The cell typically includes two electrodes of dissimilar material isolated from each other by an electrolyte through which ions can move.

The term adatom as used herein refers to a particle, molecule, or ion of material that has not yet been formed into a structure or film.

The term intercalation as used herein refers to a property of a material that allows ions to readily move in and out of the material without the material changing its phase. Accordingly, a solid-state intercalation film remains in a solid state during discharging and charging of an energy-storage device.

Figure 1A:
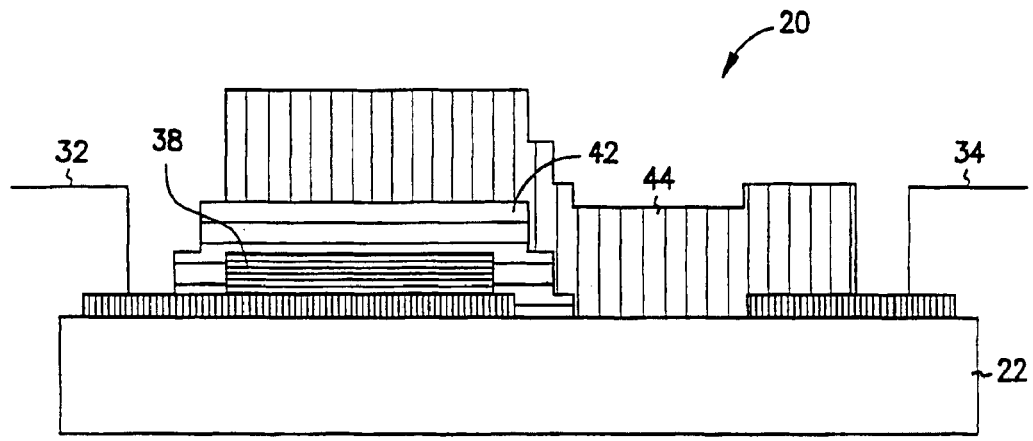
FIG. 1A is a cross-sectional view of a conventional lithium-ion battery.
Figure 1B:
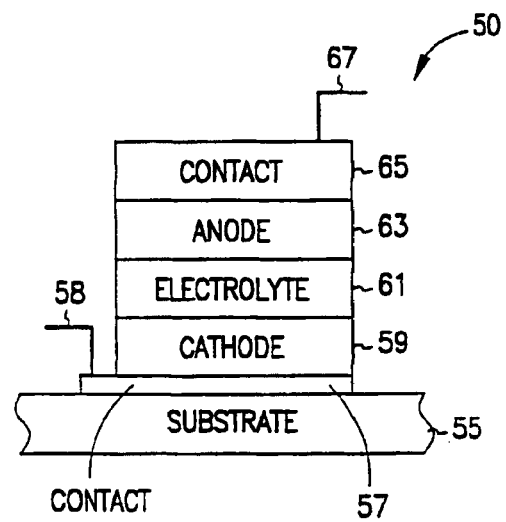
FIG. 1B is a cross-sectional view of an energy-storage device according to the present invention.

FIG. 1B shows an embodiment of an energy-storage device 50 according to the present invention. A substrate 55 is provided on which is formed a contact film 57. Contact film 57 acts as a current collector and is connected to a lead 58, which connects one pole of the energy storage device 50 to an external circuit. An electrode film 59 is formed on the contact film 57. In some embodiments, the electrode film 59 substantially covers a surface of the contact film 57 to as to minimize resistance by maximizing the area of the interface between the films. In some embodiments, the electrode film 59 is a cathode for a thin-film battery. In other embodiments, electrode film 59 is an electrode of a supercapacitor. An electrolyte film 61 is formed on the electrode film 59. An electrode film 63 is formed on the electrolyte film 61. The electrolyte film 61 isolates electrode film 59 from electrode film 63. A contact film 65 is formed on electrode film 63. Contact film 65 acts as a current collector and is connected to a lead 67, which connects one pole of the energy storage device 50 to an external circuit. In some embodiments, the contact film 65 substantially covers a surface of the electrode film 63 to as to minimize resistance by maximizing the area of the interface between these films. In some embodiments, the electrode film 63 is an anode for a thin-film battery. In other embodiments, electrode film 63 is an electrode of a supercapacitor.

Figure 1C:
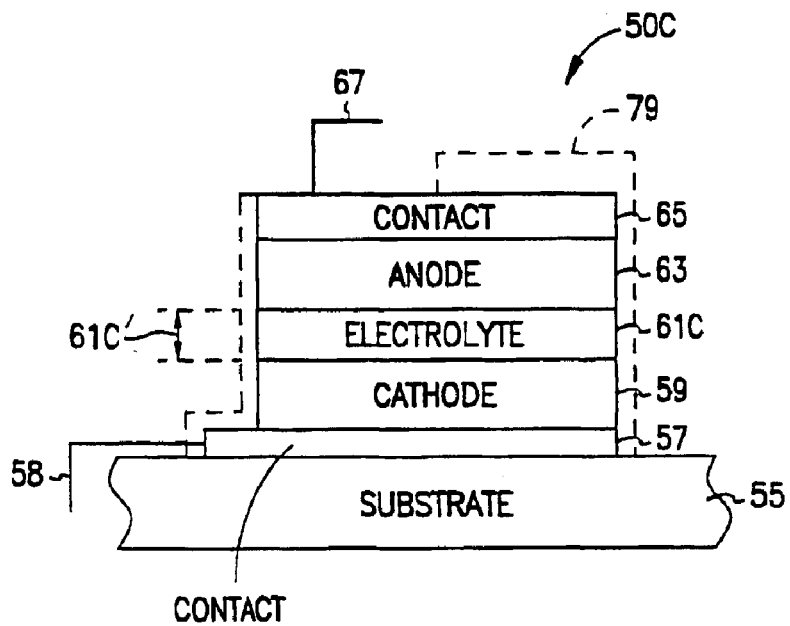
FIG. 1C is a cross-sectional view of an energy-storage device according to the present invention.

FIG. 1C shows a cross sectional view of an embodiment of an energy-storage device 50C. A substrate 55 is provided and, in some embodiments, includes additional layers and/or devices formed therewith. In some embodiments, the substrate 55 includes a substrate as described herein. Contact films 57 and 59 are formed on the substrate 55 according to the methods described herein. In some embodiments, contact films 57 and 59 are metal films deposited on the substrate according to other methods as known in the art. Contact films 57 and 59 act as contacts for connecting the energy-storage device 50C to other circuit elements (not shown).

An electrode first film 59 is formed on contact 57. Electrode first film 59 includes a metal or intercalation material in some embodiments, for example, thin-film battery embodiments in which the electrode first film 59 functions as a cathode. In some such embodiments, the electrode first film 59 includes lithium metal and/or a lithium-intercalation material. In other embodiments, such as supercapacitors, electrode first film 59 is a metal oxide. It is desirable to maximize the contact interface between the electrode first film 59 and contact film 57. Accordingly, in some embodiments, the electrode first film 59 substantially covers contact film 57 except for a portion reserved for connection to external circuits.

An electrolyte film 61C is formed on, or at least partially on, the electrode first film 59. The electrolyte film 61C, in some embodiments, completely encloses the electrode first film 59. The electrolyte film 61C is formed using the systems and methods described herein. In one embodiment, a first material of the electrolyte film 61C is deposited using a first source, which directs a first electrolyte material (adatoms) to the location on the substrate or, as shown in FIG. 1C, to a location on the electrode first film 59.

An electrode second film 59 is formed on electrolyte film 61C and contact film 59. Electrolyte film 61C completely separates the electrode first film 59 from the electrode second film 59. The electrode second film 63 includes a metal or intercalation material in some embodiments, for example, thin-film battery embodiments in which the electrode second film is an anode. In other embodiments, such as supercapacitor embodiments, electrode second film 63 is a metal oxide. Electrode second film 63, in some embodiments is deposited according to the methods described herein. In other embodiments, electrode second film 63 is formed according to methods known in the art.

The electrolyte film 61C as deposited includes the electrolyte material. A first source (e.g., sources 311, 511, 511A, and 711 as described herein) of the electrolyte material, in one embodiment, is a physical vapor deposition source. In another embodiment, the first source is a chemical vapor deposition source. A second source provides energized particles to the location. The energized particles impinge on the electrolyte material and assist in forming a desired structure of the electrolyte film 61C. In some embodiments, the second source provides energized particles simultaneously with the first source supplying the electrolyte material. The use of the energized particles conforms the electrolyte film 61C to electrode first film 59 such that the electrolyte film provides the necessary insulative property, namely preventing electrons from travelling directly between the electrode first film 59 and the electrode second film 63, i.e., shorting the electrodes. In some embodiments, the second source is an ion source as described herein, e.g., sources 313, 413, or 713. The second source provides energized ions that supply energy to the electrolyte material from the first source. The energy that is supplied by the ions assists in conforming the formed electrolyte film 61C to the electrode first layer 59. It is believed that the use of the energized particles in the energy range referenced herein provides the growing electrolyte material an extended period of mobility upon the previous film surface, and this extended period of mobility allows the electrolyte material to grow in a more defect-free manner.

In some embodiments, it is desired to form the electrolyte film 61C as thin as possible to lower its contribution to the internal resistance of the energy-storage device. It is also desired to maintain the electrolyte's property of blocking the flow of electrons (which would result in a short of the cathode to the anode) while permitting the flow of the ions that provide the battery function across the electrolyte. Using the methods and systems described herein, the electrolyte film 61C is formed to a thickness 61C' of less than about 5000 Angstroms. In some embodiments, the electrolyte film 61C has a thickness 61C' of less than about 2500 Angstroms. In some embodiments, the electrolyte film 61C has a thickness 61C' of less than about 1000 Angstroms. In some embodiments, the electrolyte film 61C has a thickness 61C' of less than about 500 Angstroms. In some embodiments, the electrolyte film 61C has a thickness 61C' of less than about 250 Angstroms. In some embodiments, the electrolyte film 61C has a thickness 61C' of less than about 100 Angstroms. In some embodiments, the electrolyte film 61C has a thickness 61C' in a range of about 10 Angstroms to about 200 Angstroms. In some embodiments, the electrolyte film 61C has a thickness 61C' in a range of about 10 Angstroms to about 100 Angstroms.

In one embodiment, the electrolyte film 61C includes LiPON and is formed using the first source 311 with the second source 313 or 413. As used herein, LiPON refers generally to lithium phosphorus oxynitride materials. One example is Li3PO4N. Other examples incorporate higher ratios of nitrogen in order to increase lithium ion mobility across the electrolyte. In some embodiments, the first source 311 provides Li3PO4 in a nitrogen atmosphere. In other embodiments, the first source 311 provides Li3PO4 in a vacuum environment wherein the background pressure is less than 1E-3 Torr. The second source 313 or 413 provides energized particles from a source gas. In some embodiments, the secondary source is an ion source supplying energetic ions from a source gas comprising oxygen (e.g., O2) or nitrogen (e.g., N2). The source gas, in other embodiments, comprises a noble gas, e.g., argon, xenon, helium, neon, and krypton. The energized particles and/or ions increase the energy of the material forming the electrolyte film 61C, thus enhancing layer-by-layer growth. Accordingly, the electrolyte film is of a higher quality than conventional electrolyte layers.

An embodiment for forming a LiPON electrolyte film 61C includes the first source providing Li3PO4 at or to the location where the LiPON electrolyte film is to be formed and second source providing energized nitrogen particles to or near the same location. The energized nitrogen particles react with Li3PO4 provided at the location for forming the electrolyte film. This increases the amount of nitrogen in the LiPON electrolyte film. Increasing the nitrogen content is desirable to increase lithium ion mobility across the electrolyte.

In a further embodiment, the chamber in which the substrate 55 is positioned has a nitrogen enhanced atmosphere. A LiPON electrolyte film 61C is formed by the Li3PO4 supplied by the first source reacting with the nitrogen in the chamber. The second source provides energized particles assisting in the formation of the electrolyte film. In another embodiment, the second source also provides nitrogen to the Li3PO4 at the location. Thus, the Li3PO4 reacts with both the nitrogen in the chamber and with energized, nitrogen containing particles supplied by the second source. This increases the nitrogen content of the electrolyte film 61C. In some embodiments, increasing the nitrogen content in the electrolyte film 61C is desirable since published data from the Department of Energy lab at Oak Ridge, Tenn. indicates an increase in nitrogen content increases the ion conductivity or mobility in the electrolyte film.

As will be understood by reading the present invention, the systems shown herein for depositing films are adaptable to form the electrolyte film 61C according to the present invention. Examples of some such systems are shown in FIGS. 3–7.

Figure 1D:
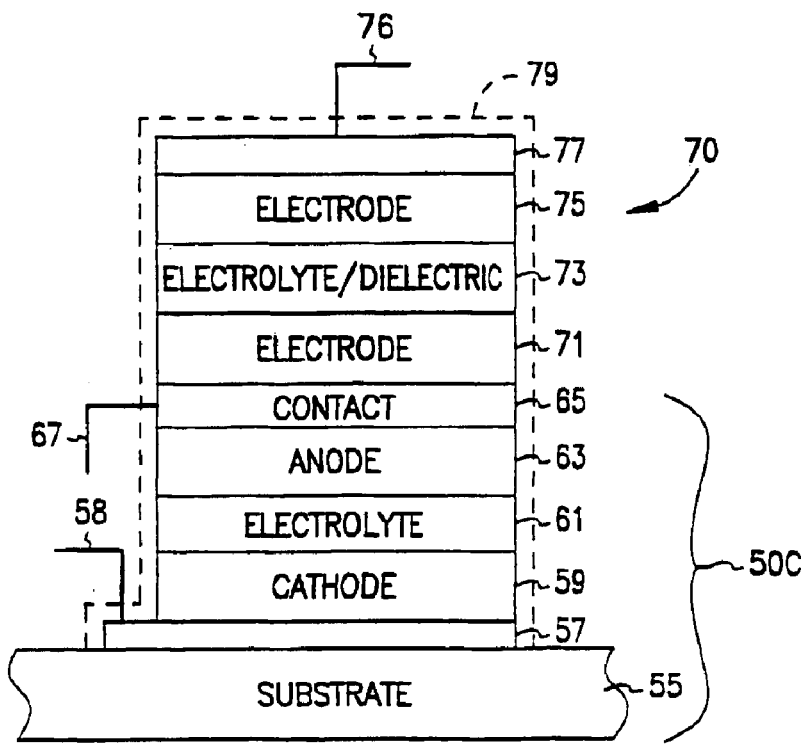
FIG. 1D is a cross-sectional view of an energy-storage device and a supercapacitor according to the present invention.

FIG. 1D shows another embodiment of an energy storage device according to the teachings of the present invention. A supercapacitor 70 is formed on the energy-storage device 50C having the ultra-thin electrolyte film 61. The energy-storage device 50C being formed on the substrate prior to forming the supercapacitor 70 represents an embodiment of layer/devices being formed on the substrate prior to applying the techniques described herein to form energy-storage and/or energy conversion devices. The supercapacitor 70 includes an intermediate film 73 formed in physical contact with electrode films 71 and 75. In some embodiments, the intermediate film 73 is an electrolyte for storing and discharging electrical charge by a faradaic process. In some embodiments, the intermediate film 73 includes a dielectric material. The contact film 65 is in physical and electrical contact with electrode 71. Thus, in this embodiment contact film 65 is a shared contact film for both the energy storage device 50C and supercapacitor 70. In other embodiments, energy storage device 50C and supercapacitor 70 have separate contact films. In some embodiments, the intermediate film 73 includes LiPON. In some embodiments, the electrolyte film 73 includes TaO. In some embodiments, the electrode films are RuO2. A contact film 77 is formed on the electrode film 75. A lead 76 extends from the contact film 77 to contact one plate of the supercapacitor to an external circuit.

Figure 2A:
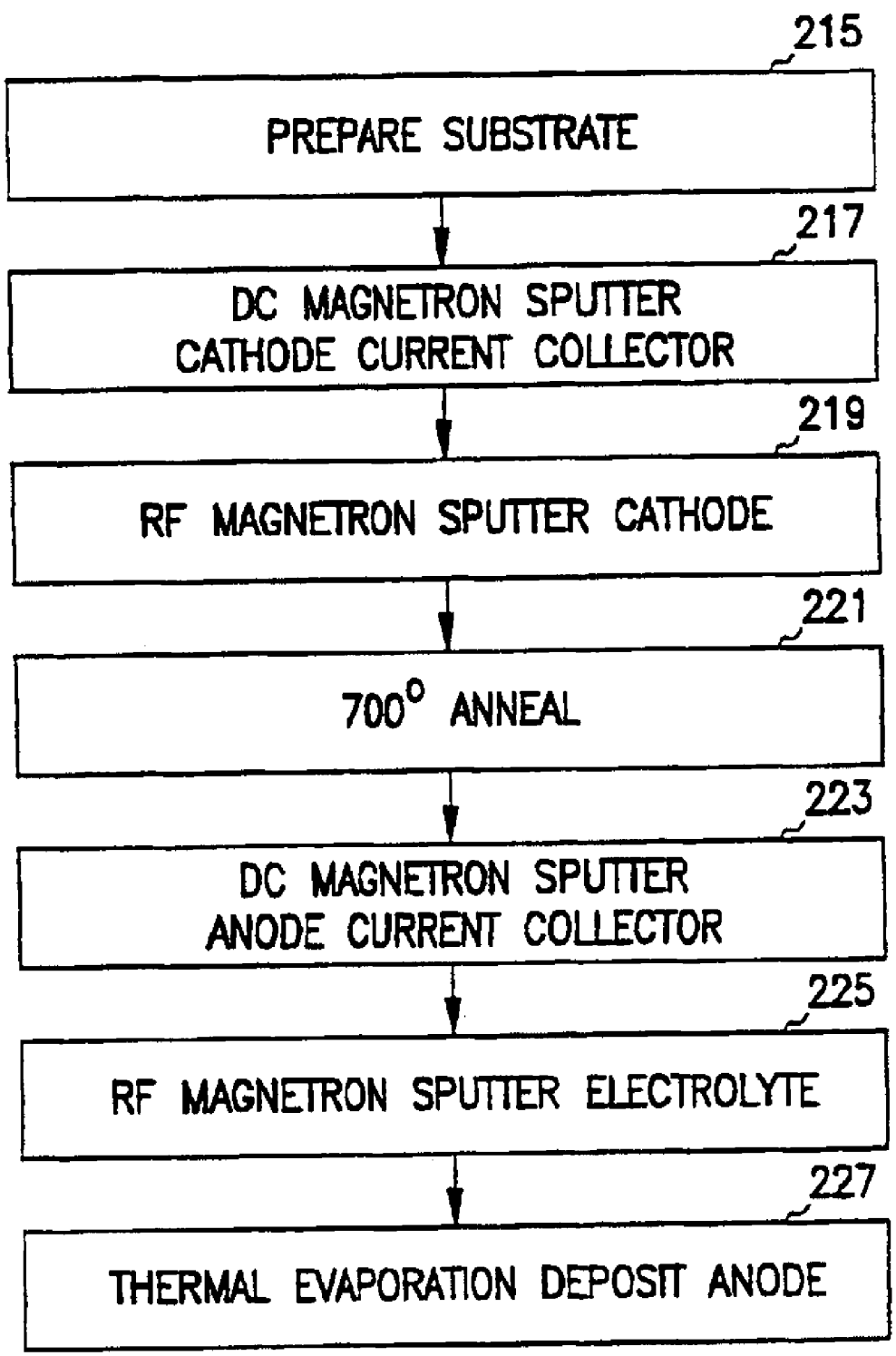
FIG. 2A is a flowchart of a conventional method for manufacturing the lithium-ion battery of FIG. 1A.
Figure 2B:
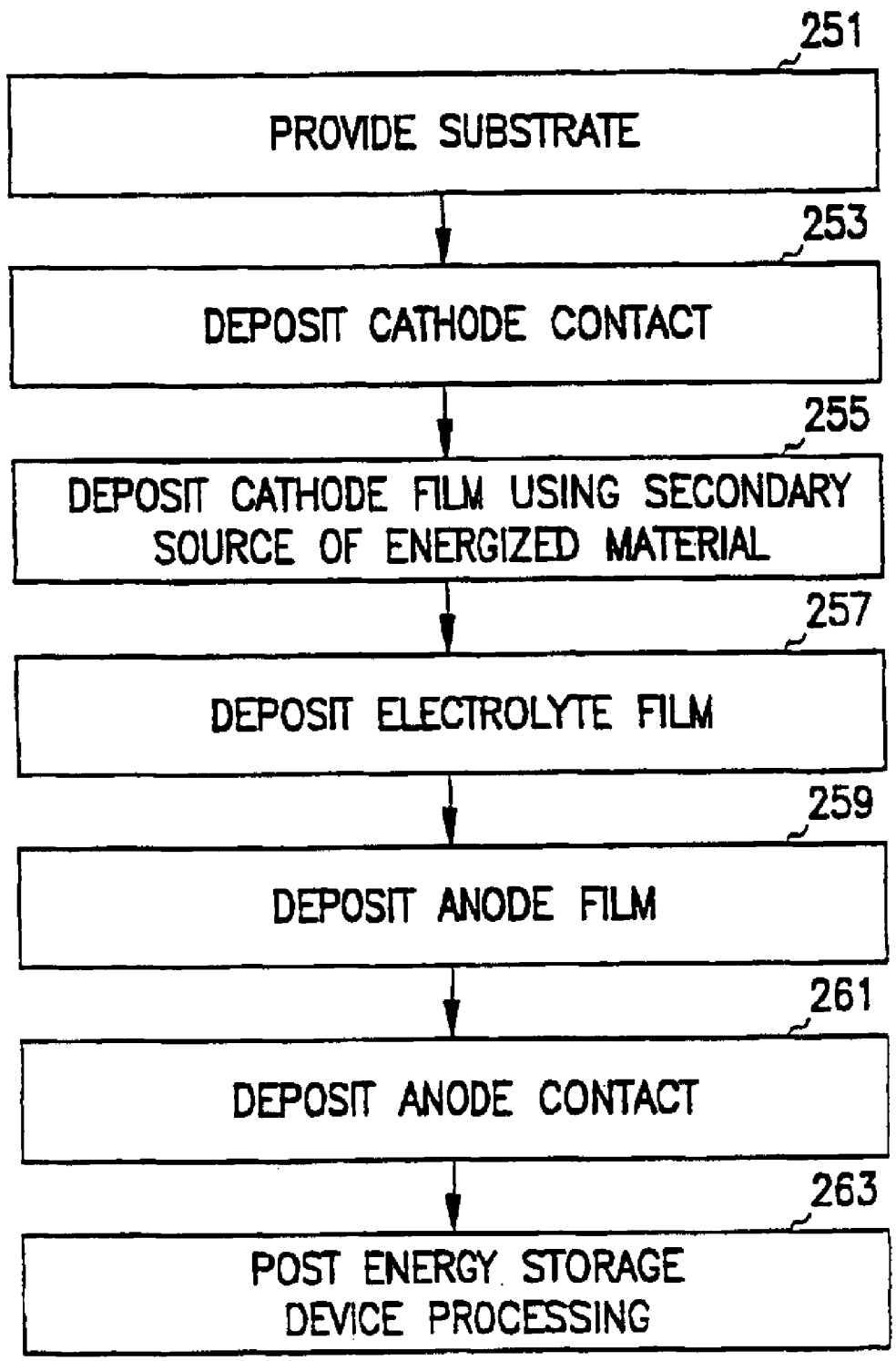
FIG. 2B is a flowchart of one embodiment of a fabrication process according to the teachings of the present invention.

A method for fabricating the solid-state energy-storage device 50 will now be described with reference to FIGS. 1B and 2B. The method includes providing a substrate 55 (step 251) and depositing a cathode contact film 57 on the substrate 55 (step 253). In some embodiments, step 251 includes providing a substrate having insulator layers or other layers/devices formed thereon. The method further includes a step 255 of depositing an electrode material to a location on the substrate, while simultaneously supplying energized particles to the electrode material at the substrate. In one embodiment, an assist source provides the energized particles. In some such embodiments, the energized particle beam is directed to the same location on the substrate as the electrode material. In an embodiment, the energized particles are energized ions. The energized ions, in an embodiment, include a material that is different than the electrode material. The energized particles or the ion beam assist in controlling growth of the structure of the electrode material at the location. In some embodiments, step 255 is used to form a cathode film or layer 59 for a solid-state, thin-film battery. The cathode film 59 is in electrical and physical contact with the cathode contact. An electrolyte film 61 is deposited, step 257, on the cathode film 59. An anode film 63 is deposited, step 259, on the electrolyte film. The electrolyte film 61 separates the cathode and anode films 59 and 61 to prevent shorting the energy-storage device 50, e.g., battery. An anode contact is formed, step 261, in electrical and physical contact with the anode film. The thin-film battery according to the present invention is now formed and is subjected to post energy-storage device fabrication steps 263.

The deposition of the cathode film includes directing a first material (e.g., adatoms) to a location on the substrate, while simultaneously supplying energized particles (e.g., ions) of a second material to the location on the substrate. In some embodiments, the second material is different from the first material. The energized particles supply energy to the first material to assist in the growth of a desirable crystal structure in the cathode film. Moreover, this controls the stoichiometry of the growing film at the location on the substrate. In one embodiment, the first material is a lithium-intercalation material used as a solid-state, thin-film battery cathode. The assist source provides ions that provide energy in a range of 5 eV to 3000 eV to the lithium-intercalation material. Control of the energy in the ions produced by the assist source provides in situ control for growing a lithium-intercalation film having a crystalline structure. The energy from the ions assists the formation of lithium-intercalation materials into a crystalline structure at the time of deposition. In one embodiment, the gas used to form the ions is used to control the stoichiometry of the growing, crystalline film. For example, an ionized, assist beam of O2 is used to control the growth and stoichiometry of a LiCoO2 intercalation material. In some such embodiments, the O2 in the ion assist beam combines with LiCo at the location to form the LiCoO2 intercalation material.

The crystalline structure of a thin film formed according to the teachings herein has a higher order than those achieved by conventional cathode film forming techniques. Conventional techniques rely on a high-temperature, post-cathode-deposition anneal to reorder and crystallize the structure of a conventional cathode film. Unfortunately, such conventional techniques anneal the entire structure to the same temperatures, which is undesirable in that the substrate must withstand such temperatures which eliminates many otherwise suitable substrate materials from consideration. Further, different layers cannot be provided with different anneals suited to their different requirements. A highly ordered crystalline cathode film is desirably achieved according to the teachings described herein by providing the required energy to form the desired, high-order and appropriately oriented crystal structure without subjecting the substrate, and other layers formed on the substrate including the cathode-contact film to a high-temperature anneal. Further, each layer can be annealed using a different anneal process (such as using ion assist beams having different energies for different layers, or depositing and annealing at different rates or for different durations). Further, by annealing the surface layer of the previous layer, a subsequent layer can be deposited onto a surface that has been ordered in a specific way (for example, to achieve a specific crystal orientation, or a specific ion-bonding surface) that enhances the quality of that subsequent layer.

Figure 2C:
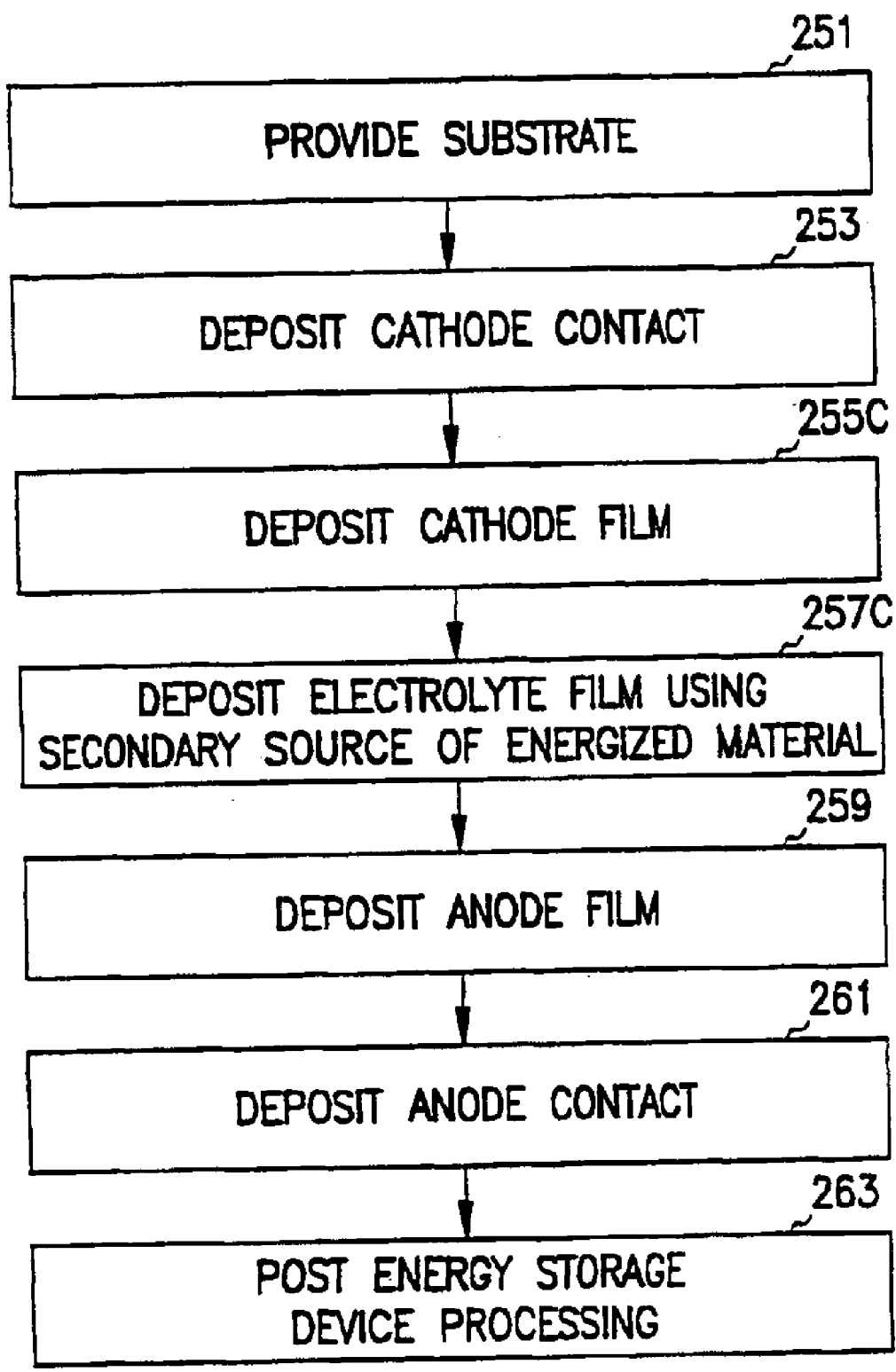
FIG. 2C is a flowchart of one embodiment of a fabrication process according to the teachings of the present invention.

FIG. 2C shows one embodiment of a method for fabricating an energy-storage device. Steps 251, 253, 259, 261, and 263 are the substantially similar to the steps described above with reference to FIG. 2B. Step 255C is a step for depositing a cathode film at least partially on the cathode contact film. In an embodiment, the cathode film is deposited as described above in step 255. In other embodiments, the cathode film is deposited according to other deposition processes known in the art. The electrolyte film is formed by depositing an electrolyte material to a location at least partially in contact with the cathode film (step 257C). In a preferred embodiment, the electrolyte material is in contact with a substantial portion of, if not all of, a surface of the cathode film. In some embodiments, an assist source simultaneously supplies energized particles to the electrolyte material as it forms the electrolyte film. In an embodiment, the assist source supplies a beam of energized ions of an assist material different than the electrolyte material. In one embodiment, the second material beam is directed to the same location on the substrate as the electrolyte material. The energized ion beam assists in controlling growth of the structure of the electrolyte film. The ion beam is unfocused in one embodiment. The ion beam is focused in another embodiment.

The deposition of the electrolyte film includes directing an electrolyte material to a location at least partially in contact with the cathode film, while simultaneously supplying energy to the electrolyte material. In one embodiment, the energy is supplied by energized particles. In some such embodiments, the energized particles are energized ions. In some such embodiments, the energized particles from the assist source are of a different material than the electrolyte material. The energized particles supply energy to the electrolyte first material to assist in the growth of a desirable, solid electrolyte-film structure. Moreover, this controls the stoichiometry of the growing electrolyte film.

In one example, the electrolyte material is a lithium phosphorus oxynitride. In some embodiments, the assist source provides ions that provide energy in a range of about 5 eV to about 5000 eV to the lithium phosphorus oxynitride ("LiPON"). Control of the energy in the ions produced by the assist source provides in situ control for growing a lithium phosphorus oxynitride structure at the location. The energy from the ions assists the formation of the lithium phosphorus oxynitride material into a desirable structure at the time of deposition. In one embodiment, the gas used to form the ions is used to control the stoichiometry of the growing electrolyte film. For example, an ionized assist beam of O2 is used to control the growth and stoichiometry of a lithium phosphorus oxynitride material. In another embodiment, an ionized assist beam of N2 is used. In this embodiment, the N2 not only controls growth and stoichiometry of the electrolyte film, but also injects additional nitrogen into the electrolyte film. This is desirable due to the ionic transportivity of a LiPON electrolyte film is dependant on the amount of nitrogen in the film.

Figure 2D:
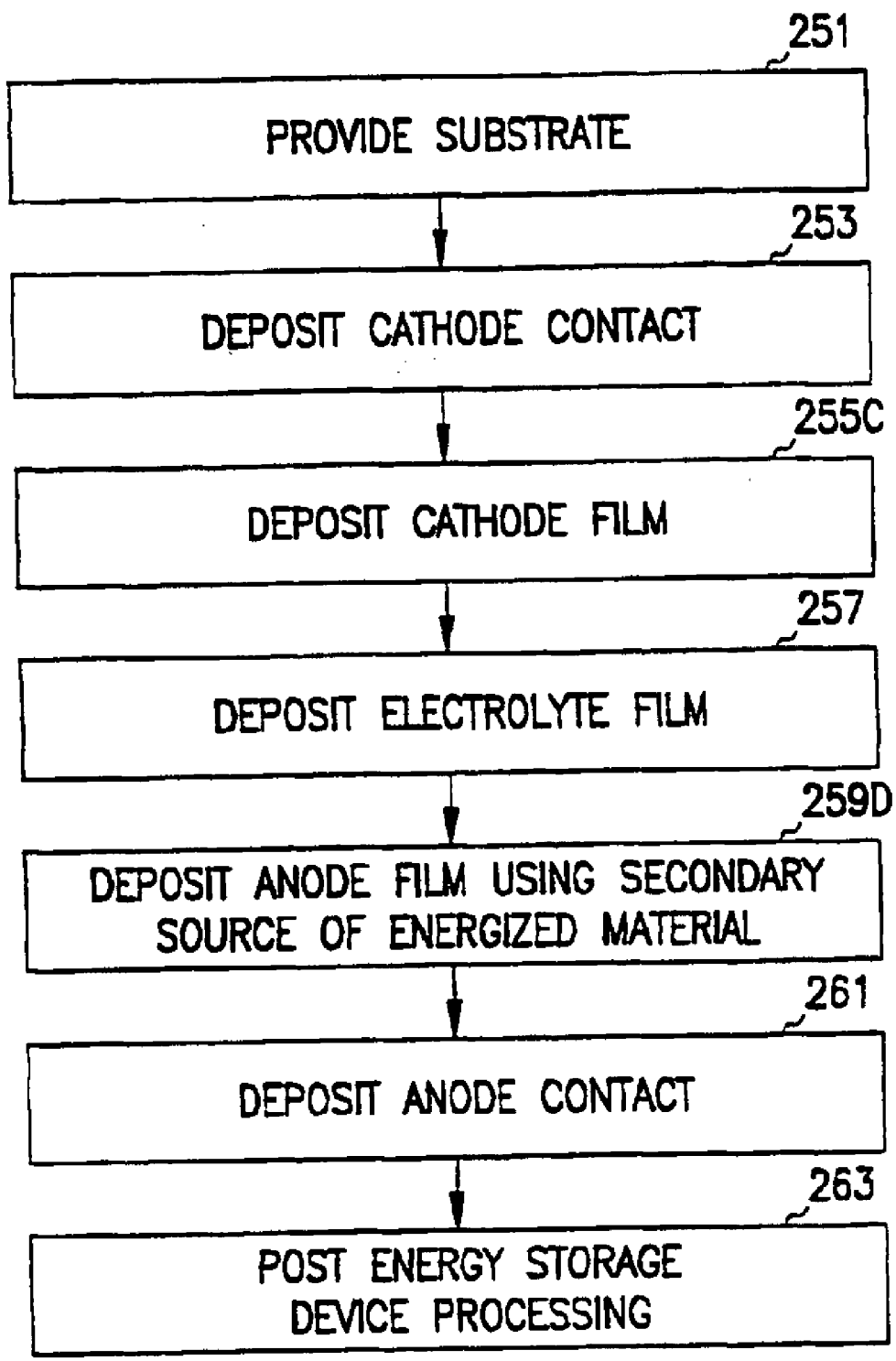
FIG. 2D is a flowchart of one embodiment of a fabrication process according to the teachings of the present invention.

FIG. 2D shows one embodiment of a method for fabricating an energy-storage device. Steps 251, 253, 257, 261, and 263 are substantially similar to the steps described above with reference to FIG. 2B. Step 255C is a step for depositing a cathode film at least partially on the cathode contact film. In an embodiment, the cathode film is deposited as described above with reference to FIG. 2B. In other embodiments, the cathode film is deposited according to other deposition processes known in the art. Step 259D is a step for depositing an electrode material to a location at least partially on the electrolyte film, while simultaneously supplying energized particles to the electrode material. In one embodiment, the energized particles are directed to the same location as the electrode material. In an embodiment, the energized particles are energized ions. The energized ions, in an embodiment, include a second material that is different than the first material. The energized particles or the ion beam assist in controlling growth of the structure of the electrode material. Step 259D, in some embodiments, is used to form an anode film for a solid-state thin-film battery. The anode film is in electrical and physical contact with the anode contact and electrolyte films.

The deposition of the anode film includes directing an electrode material to a location at least partially in contact with the electrolyte film, while simultaneously supplying energized particles of a second material. The energized particles supply energy to the electrode material to assist in the growth of a desirable crystal structure in the anode film. Moreover, this controls the stoichiometry of the growing film. In one embodiment, the electrode material includes a lithium-intercalation material used as a battery anode. In an embodiment, the anode includes is a lithium metal or a lithium alloy. In another embodiment, the anode includes a carbonaceous material, such as graphite or diamond-like carbon. In another embodiment, the anode includes a metal oxide, for example, RuO or VaO. In another embodiment, the anode includes a nitride material. A secondary source provides particles, which are ions in some embodiments, that provide energy in a range of about 5 eV to about 3000 eV to the lithium-intercalation material. Control of the energy in the ions produced by the secondary source provides in situ control for growing a lithium-intercalation crystalline structure at the location. The energy from the ions assists the formation of lithium-intercalation materials into a crystalline structure at the time of deposition. In one embodiment, the gas used to form the ions is used to control the stoichiometry of the growing, crystalline film.

The crystalline structure of an electrode thin film formed according to the teachings herein has a higher order than those achieved by conventional film forming techniques. Conventional techniques rely on a high-temperature, post-deposition anneal that affects the substrate and other layers as well as the film intended to reorder and crystallize the structure of that film. In contrast, the present invention provides a controlled energy source at the time of deposition or after the time of deposition that reorders the surface of the deposition film without substantially heating the underlying layers or substrate. In some embodiments, the energy is provided while depositing each atomic layer of a film such that each atomic layer is ordered as crystallizes into the film. Examples of such energy sources include an ion beam that either react with the adatoms being deposited and/or provide kinetic energy to assist in deposition of the film. Other examples of energy sources include high temperature, short duration heat sources, short duration plasma sources, lasers, other high intensity photo sources that reorder the crystal structure adjacent the surface of the film without effecting other layers or the substrate. A highly ordered crystalline cathode or anode is desirably achieved according to the teachings described herein.

While the above fabrication process describes forming cathode and anode films in a certain order, other embodiments reverse the order of the cathode film and anode film. Moreover, the fabrication process describes forming cathode and anode films, for example in a battery. In some embodiments, the cathode and anode films are electrodes of a battery. Other embodiments include films forming various layers of supercapacitors. Supercapacitors operate In these embodiments, at least one of the films forming the supercapacitor, e.g., electrode films 71, 75 and electrolyte and/or dielectric film 73, have improved crystalline structure, crystallite size, or fewer defects without resorting to a high temperature anneal of the entire structure to provide these properties. Accordingly, techniques and systems for fabricating thin films for use in an energy-storage device as described herein are applicable to both solid-state batteries and solid-state capacitors.

In another embodiment, the thin-film energy-storage device is formed on a substrate. A contact film, which is electrically conductive and does not react with a subsequently deposited, adjacent cathode film, is formed on the substrate. The contact film acts as a barrier between the substrate and the cathode film. The contact film further acts as a current collector and as a connection between the cathode film and circuits that are external to the energy-storage device. In an embodiment, the contact film has a thickness of greater than 0.3 microns.

Figure 3A:
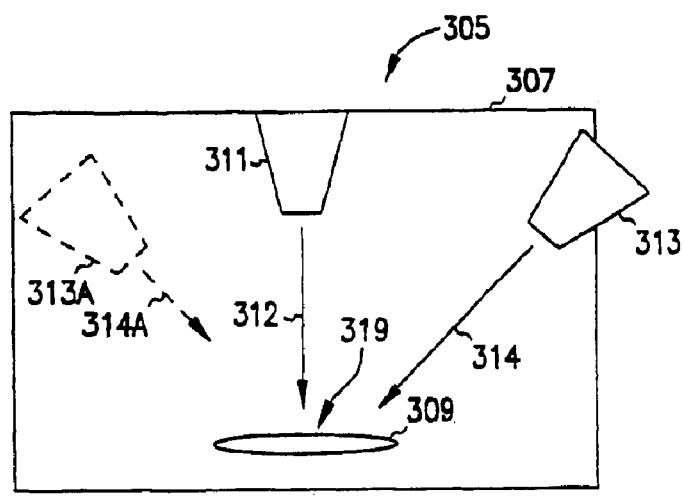
FIG. 3A is a diagram of a device for fabricating a thin-film battery according to the teachings of the present invention.

FIG. 3A shows a deposition apparatus 305 including a reaction chamber 307 in which is positioned a substrate 309 on which an energy-storage device is to be fabricated. Reaction chamber 307, in one embodiment, is a sealed chamber that holds gases for the reaction and that provides a sub-atmospheric pressure. In some embodiments, it is desirable to hold the pressure in the chamber less than about 1×10−3 Torr. A first material source 311 is provided in the chamber 307. The first source 311 produces a beam of adatoms 312 of a first material to be deposited on the substrate 309. In one embodiment, the first material source 311 is a physical vapor deposition source. In one such embodiment, the material source 311 is an e-beam source. In another such embodiment, the first source 311 is an arc source including, for example, a cathodic-arc source, an anodic-arc source, and a CAVAD arc source. Arc sources are particularly suited for use as a source as they effectively operate in a chamber that is operated at low temperatures. In another embodiment, the first source 311 is a physical deposition source including, for example, a sputtering source. In another embodiment, the source 311 is a chemical vapor deposition source including, for example, a direct ion source using a hydrocarbon precursor gas. Beam 312 is focused on a location 319 on the substrate 309 whereat the material of the beam 312 is deposited to form a film of an energy-storage device. An assist source 313 is provided in the chamber 307 and produces a beam of energized particles 314 directed at least adjacent to the location 319 on the substrate 309. In some embodiments, the assist source is an energized ion-producing source. In some embodiment, the assist source 313 is offset from the first source 311 such that the beams from these sources are not coincident. The energized particle beam 314 provides the energy that is required to control the growth and stoichiometry of the material in the first beam 312 into a crystalline structure on the substrate 309 as is explained in greater detail herein. In one embodiment, the energized particle beam 314 also provides elements that are required in the film being deposited. In another embodiment, beam 314 is directed at least near location 319 such that sufficient energy to form the desired crystal structure and stoichiometry of the film being deposited is supplied by beam 314 to the material in first beam 312. In some embodiments, the deposition system 305 includes at least one additional assist source 313A. In some embodiments, each of the sources 313A provides an additional assist beam 314A that provides energy to arriving adatoms at the substrate. Various embodiments of assist beams 314 are described below.

Figure 3B:
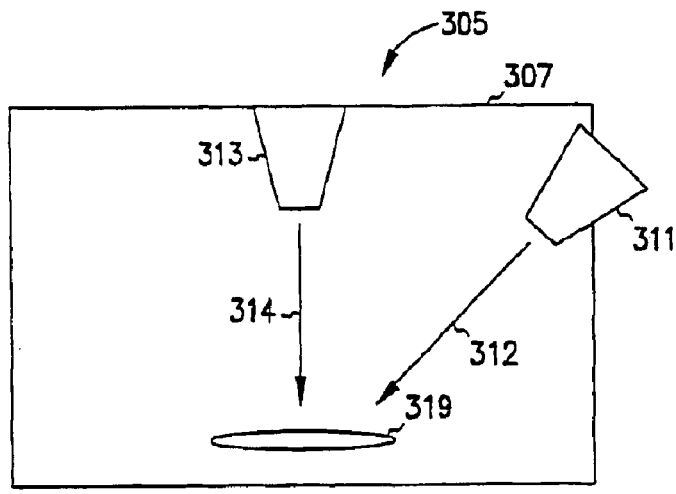
FIG. 3B is a diagram of a device for fabricating a thin-film battery according to the teachings of the present invention.

FIG. 3B shows another embodiment of a deposition apparatus 305. The assist source 313 produces an energy beam 314 that travels along a path that is essentially normal to the substrate 319. The source of material to be deposited 311 is offset from assist source 313. In some embodiments, source 311 produces a beam of adatoms 312 that travels along a path that is non-normal to the substrate 319. The energy beam supplies energy to the adatoms from beam 312 as described herein.

Figure 4:
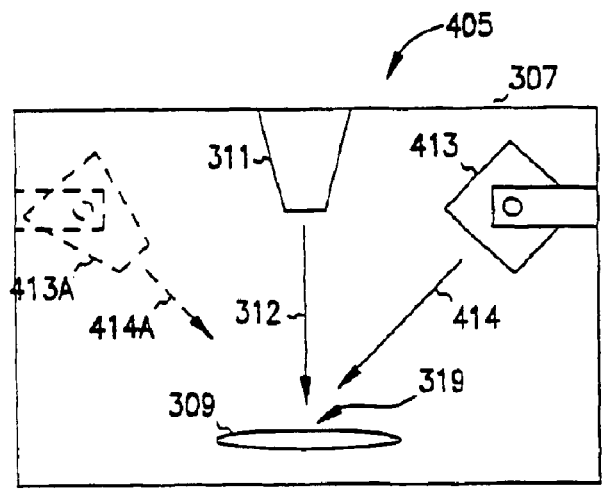
FIG. 4 is a diagram of another embodiment of a device for fabricating a thin-film battery according to the teachings of the present invention.

FIG. 4 is a view substantially similar to FIG. 3A, except that depositing apparatus 405 includes an assist source 413 for producing the energized beam that is pivotally mounted to a bracket fixed in the chamber 307. The assist source 413 pivots to direct the energized particle beam 414 at a desired impingement angle to the surface of the substrate 309. In an embodiment, the impingement angle is in the range of about 15 degrees to about 70 degrees from normal to the substrate. Accordingly, in some embodiments, the impingement angle is variable. In one embodiment, the impingement angle is about 45 degrees. In some embodiments, the deposition system 405 includes at least one additional assist source 413A. In some embodiments, each of the sources 413A provides an additional assist beam 414A that provides energy to arriving adatoms at the substrate. In some embodiments, the energy provided by assist beam 414 differs from the energy provided by at least one of assist beams 414A. In some embodiments, the assist beam 414 and 414A need not simultaneously transmit energy to the adatoms. In some embodiments, the means by which the beams 414 and 414A transmit energy are different. In some embodiments, the material in beams 414 and 414A are different.

Figure 5A:
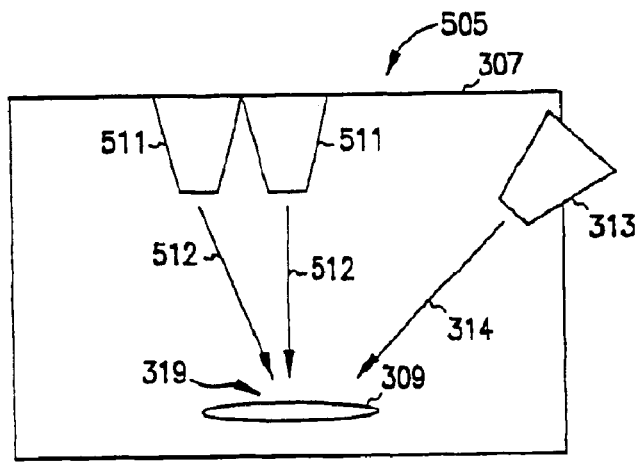
FIG. 5A is a diagram of another embodiment of a device for fabricating a thin-film battery according to the teachings of the present invention.

FIG. 5A is a view substantially similar to FIG. 3 except that depositing apparatus 505 includes a plurality of first deposition sources 511. In one embodiment, each one of the first deposition sources 511 directs its respective beam 512 to the location 319 on the substrate 309. In some embodiments, every one of the first sources 511 produces a beam 512 including the same material. In other embodiments, at least of the first sources 511 produces a beam 512 of a material that is different than that of another of the first sources 511. In some embodiments, the materials from the plurality of first beams 512 combine at the location 319 to form the desired film. In other embodiments, the materials in first beams 512 combine with material from assist beam 314 to form the desired film. In one embodiment, one of the first sources 511 directs its beam 512 to the substrate 319 but away from the location 319. In some embodiments, a plurality of assist sources 313 provide energy to the adatoms of beams 512.

Figure 5B:
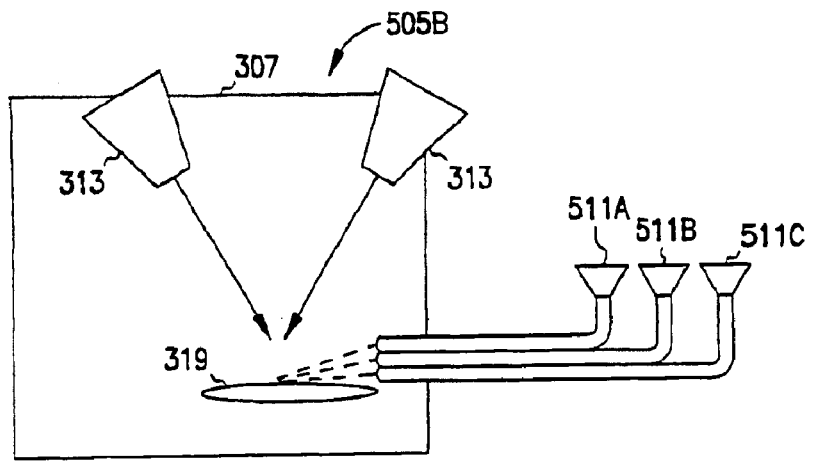
FIG. 5B is a diagram of another embodiment of a device for fabricating a thin-film battery according to the teachings of the present invention.

FIG. 5B shows another embodiment of a depositing apparatus 505B. A plurality of assist sources 313 is positioned to provide energy to a forming film at the substrate 319. A plurality of material sources 511A, 511B, and 511C supply material to the chamber 307 and adjacent the surface of the substrate 319. In some embodiments, each of the material sources 511A, 511B, and 511C provide a same material and, thus, have the ability to provide a greater quantity than one of the sources alone. In some embodiments, at least one of the material sources 511A, 511B, and 511C provides a material different than another of the material sources. In some embodiments, these different materials react at the in chamber 307 to create the adatom material that will form a film on the substrate 319. In some embodiments, at least one of the material sources 511A, 511B, and 511C provides a precursor material into chamber 307 and another of the material sources provides a reactant material into the chamber. The precursor and reactant material react together to create the material that will form the film. In some embodiments, at least one of the material sources 511A, 511B, and 511C includes a chemical reactor in which chemicals react. This source then injects the resultant material into the chamber. The resultant material is included in the film fabrication process.

Figure 6:
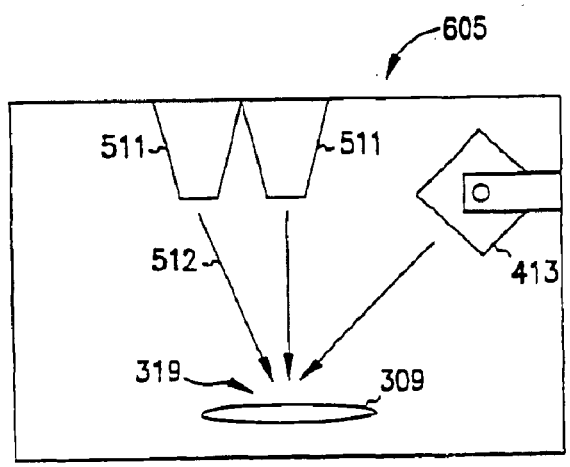
FIG. 6 is a diagram of another embodiment of a device for fabricating a thin-film battery according to the teachings of the present invention.

FIG. 6 is a view substantially similar to FIG. 5A except that depositing apparatus 605 includes a plurality of first deposition sources 511 and a pivotable assist source 413. In some embodiments, this provides more material to a given deposition location. In some embodiments, this provides deposition at multiple locations. In still other embodiments, this allows different materials from different sources to be combined.

Figure 7:
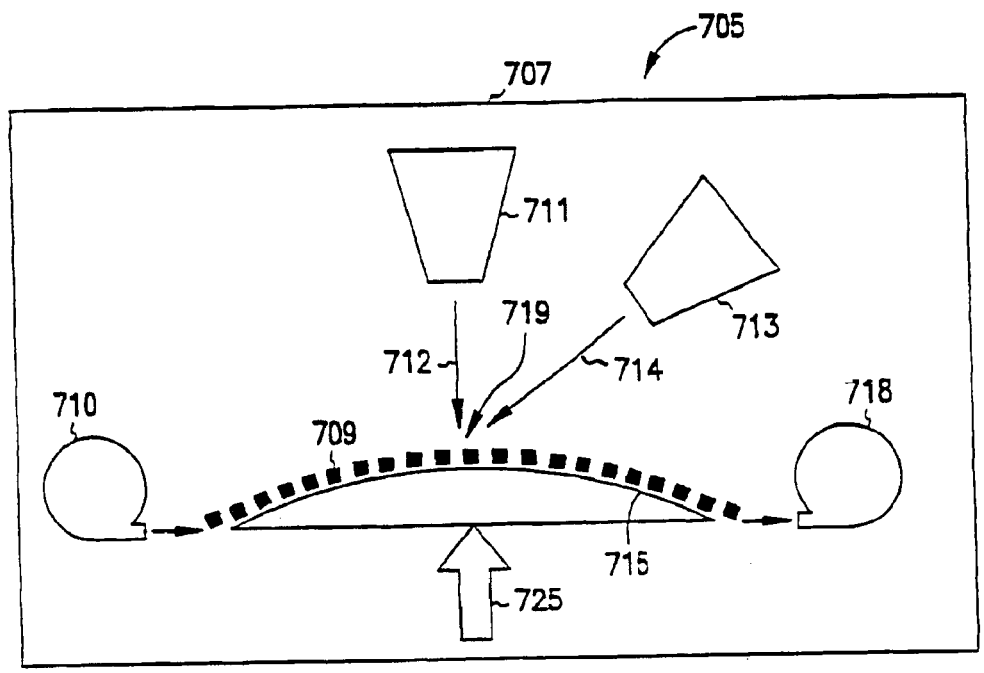
FIG. 7 is a diagram of another embodiment of a device for fabricating a thin-film battery according to the teachings of the present invention.

FIG. 7 shows another embodiment of a depositing apparatus 705 according to the teachings of the present invention. Depositing apparatus 705 includes a reaction chamber 707 in which is positioned an elongate, flexible substrate 709 on which an energy-storage device is to be fabricated. The substrate 709 is fed from a source roll 710 over an arched thermal control surface 715 and taken up by an end roll 718. A first material source 711 is provided in the chamber 707 and is a physical deposition source. First source 711 produces a beam of adatoms 712 of a material to be deposited on the substrate 709. In one embodiment, the first source 711 is an arc source including, for example, a cathodic arc source, an anodic arc source, and a CAVAD arc source. In another embodiment, the first source 711 is a physical vapor deposition source including, for example, a sputtering source. In another embodiment, source 711 is a chemical vapor deposition source. Moreover, source 711, in some embodiments, represents a plurality of different material sources. Beam 712 is focused on a location 719 on the substrate 709 whereat the adatoms in the beam are deposited to form a film layer of an energy-storage device. An assist source 713 is provided in the chamber 707 and produces a beam of energized particles 714 directed at the substrate 709. In an embodiment, the assist source 713 produces a beam of energized ions 714. The energized particle beam 714 provides the energy required to control growth and stoichiometry of the deposited material of the first beam 712. Thus, a crystalline structure is formed on the substrate 709 as is explained in greater detail herein. The substrate 709, in one embodiment, is an elastomer, polymer, or plastic web or sheet on which the energy-storage device is fabricated. Substrate 709, being elongates, allows a plurality of energy-storage devices to be deposited on successive locations of the substrate, thereby improving the rate of energy device production. Moreover, a plurality of deposition apparatuses 705 or sources 711, in some embodiments, are provided for simultaneously depositing a plurality of films at different locations on the substrate 709.

The thermal control surface 715 is connected to a thermal source 725, which controls the temperature of surface 715. The substrate 709 is in thermodynamic contact with surface 715 to thereby control the temperature of the substrate as needed for a particular deposition process on a particular substrate. In one embodiment, the thermal source is a coolant source, for example a cryogenic vacuum pump that releases compressed helium toward the surface 715 to cool it. The use of a thermally controlled surface 715 in direct contact with the substrate 709, especially when the direct contact is aligned or coincident with the location whereat a thin film is being formed, allows the use of substrates that have lower thermal degradation temperatures than are possible using conventional solid-state thin-film battery fabrication processes.

The above provides descriptions of various embodiments of systems in which the present invention is performed to produce energy-storage devices or energy-conversion devices. It is within the scope of the present invention to combine the elements of the systems in different ways than shown and described as long as the methods described herein are performable with such a system. For example, in some embodiments, the flexible substrate 709 and rolls 710, 718 can be combined with any of the embodiments shown in FIGS. 3A–6. In some embodiments, the thermal source 725 is also combinable with any of the embodiments of FIGS. 3A–6. In some embodiments, the pivotable assist sources 413 are combinable with any of the embodiments of FIGS. 3A, 3B, 5A, 5B, and 7. In some embodiments, the material sources 511A, 511B, and 511C are combinable with embodiments of FIGS. 3A–5A and 6–7.

In one embodiment, the electrode second film, e.g., films 59 or 71 is a lithium-intercalation material which overlays at least part of the first film, e.g., contact films 57 or 63, but does not extend beyond the boundary of the first film. Thus, the intercalation second film remains in a solid state during discharging and charging of the energy-storage device. In some embodiments, the second film is deposited using the first deposition source simultaneously with the secondary source supplying energetic ions to the growing second film. In some embodiments, the first deposition source is a physical vapor deposition source. In some embodiments, the secondary source is an ion source supplying energetic ions from a source gas comprising oxygen (e.g., $O_2$) or nitrogen (e.g., $N_2$). The source gas, in another embodiment, comprises a noble gas, e.g., argon, xenon, helium, neon, and krypton. The source gas, in yet another embodiment, comprises a hydrocarbon material such as a hydrocarbon precursor. Selection of the secondary source gas is based on the desired effect on the stoichiometry of the deposited film. The secondary source, in one embodiment, provides a focused beam of energized ions. The secondary source, in one embodiment, provides an unfocused beam of energized ions. The energized ions provide energy to the lithium-intercalation material in the range of about 5 eV to about 3,000 eV. In one embodiment, the energy range of is about 5 eV to about 1,000 eV. The energy range in a further embodiment is about 10 eV to about 500 eV. The energy range in a further embodiment is about 30 eV to about 300 eV. In another embodiment, the energy range is in the range of about 60 eV to 150 eV. In another embodiment, the energy range is about 140 eV. In an embodiment, the second film has a thickness of greater than 10 microns. In one embodiment, the second film has a thickness in the range of about 10 to 20 microns. In one embodiment, the second film has a thickness in the range of about 1 to 5 microns.

An electrolyte third film, e.g., films 61, 61C or 73, having ionic transport qualities but not being electrically conductive (an electrolyte) is deposited so as to completely overlay the second deposited film. In one embodiment, the third film is deposited using a first deposition source and a secondary source supplying energetic ions to the growing film. In some embodiments, the first deposition source is a physical vapor deposition source. In some embodiments, the secondary source is an ion source with the capability of supplying energetic ions having an energy greater than 5 eV. In another embodiment, the energy range is about 5 eV to about 3,000 eV. In one embodiment, the energy range of is about 5 eV to about 1,000 eV. The energy range in a further embodiment is about 10 eV to about 500 eV. The energy range in a further embodiment is about 30 eV to about 300 eV. In another embodiment, the energy range is in the range of about 60 eV to 150 eV. In another embodiment, the energy of the ions from the secondary source is about 140 eV. In some embodiments, the secondary source includes oxygen (e.g., $O_2$) or nitrogen (e.g., $N_2$) gas. The secondary source gas, in another embodiment, includes a noble gas, e.g., argon, xenon, helium, neon, and krypton. The secondary source gas, in another embodiment, includes a hydrocarbon material such as a hydrocarbon precursor. Selection of the secondary source gas is based on the desired effect on the stoichiometry of the deposited film. The secondary source, in one embodiment, provides a focused beam of energized ions. The secondary source, in one embodiment, provides a non-focused beam of energized ions. It is desirable to make the electrolyte, third layer as thin as possible and prevent the cathode and anode layers from shorting. In an embodiment, the third film has a thickness of less than 1 micron. In one embodiment, the third film has a thickness in of less than 5,000 Angstroms. In another embodiment, the third film has a thickness of less than 1,000 Angstroms. In another embodiment, the third film has a range of about 10 Angstroms to about 100 Angstroms.

In another embodiment, the third film is deposited using a first source supplying energetic ions (5 to 3000 eV) to a material source (target) at an impingement angle of 15 to 70 degrees and a second source supplying energetic ions to the growing film. The first deposition source includes a beam of focused energetic ions from a source gas. The source gas includes one of the sources gases described herein.

An anode, fourth film, e.g., film 65 or 75 includes from a lithium-intercalation material that is deposited on and overlays the third film but not contacting first film (barrier) or second film (cathode). In one embodiment, the fourth film is deposited using a first deposition source simultaneously with a secondary source supplying energetic ions to the growing fourth film. In some embodiments, first deposition source is a physical vapor deposition source. In some embodiments, the secondary source is an ion source supplying energetic ions from a source gas that includes oxygen (e.g., $O_2$) or nitrogen (e.g., $N_2$). The source gas, in another embodiment, includes a noble gas, e.g., argon, xenon, helium, neon, and krypton. The source gas, in another embodiment, includes a hydrocarbon material such as a hydrocarbon precursor. Selection of the secondary source gas is based on the desired effect on the stoichiometry of the deposited film. The secondary source, in one embodiment, provides a focused beam of energized ions. The secondary source, in another embodiment, provides an unfocused beam of energized ions. The energized ions provide energy to the lithium-intercalation material in the range of about 5 eV to about 3,000 eV. In one embodiment, the energy range of is about 5 eV to about 1,000 eV. The energy range in a further embodiment is about 10 eV to about 500 eV. The energy range in a further embodiment is about 30 eV to about 00 eV.

In another embodiment, the energy range is in the range of about 60 eV to 150 eV. In another embodiment, the energy range of the ions from the secondary source is about 140 eV. In an embodiment, the fourth film has a thickness of greater than 10 microns. In one embodiment, the fourth film has a thickness in the range of about 10 to 40 microns.

In another embodiment, the fourth film is deposited by plasma decomposition of hydrocarbon pre-cursor(s) at the surface of the substrate thereby forming a lithium-intercalation anode. In some embodiments, deposition is performed by plasma enhanced CVD using hydrocarbon precursors. In one embodiment, the deposition includes dopants such as N2. In one embodiment, a secondary source provides energized ions to assist in the deposition of the fourth film. The energized ions provide energy in the range as described herein. In some embodiments, the secondary source is the same as any described herein.

In another embodiment, the anode, fourth film is deposited by direct ion beam deposition of a lithium-intercalation material using hydrocarbon precursors. The first deposition source provides a beam of focused energetic ions (5 to 3000 eV) from a source gas hydrocarbon precursor directed at the target material. In one embodiment, a secondary source supplies energetic ions to assist in growing the fourth film and is a secondary source as described herein.

A contact, fifth film, e.g., film 65 or 77, which is electrically conductive and does not react with the fourth film is formed in contact with at least part of the fourth film. The fifth film does not contact the second film (cathode). In an embodiment, the fifth film has a thickness of greater than 0.5 microns. The fifth film acts as an anode current collector for contact to external circuitry.

In some embodiments, a passivation, sixth film 79, which is electrically non-conductive and chemically inert, essentially overlays the energy-storage device as formed thus far, i.e., all the second, third, and fourth films, so that same are packaged and free from environmental contaminants that may react with these films and degrade performance of the energy-storage device. Environmental contaminants may include further fabrication materials for devices with the energy-storage device integrated therewith. In some embodiments, the first and fifth contact films are partially exposed outside the sixth film for connection to circuitry outside the energy-storage device.

The substrate 55, 309 or 709, on which the films described herein are deposited, includes any material capable of supporting a thin film and being able to withstand the deposition process described herein. In one embodiment, the substrate is formed of a material having a temperature at which it will begin to degrade due to thermal effects of less than 700 degrees Celsius. A further embodiment includes a substrate having such a temperature at which it experiences thermal degradation of less than or equal to about 300 degrees Celsius. Thermal degradation of the substrate includes loss of shape of the substrate, loss of sufficient rigidity to support an energy-storage device, chemical breakdown of the substrate, cross-linking of materials on the substrate and/or films, melting, and combustion. Examples of substrates include silicon wafers and silicon on insulator structures. Other examples of substrate materials include metals on which an insulator layer is formed prior to formation of the energy-storage device as described herein. In another example, the metal may act as a contact for the energy-storage device with insulator layers electrically separating the electrolyte film, the anode film and the anode contact from the metal substrate. Examples of other materials that have a low thermal degradation temperature that are suitable for fabricating an energy-storage device as disclosed herein include paper, fabrics (natural and synthetic), polymers, plastics, glasses, and ceramics.

The substrate 55, 309, or 709 has a form that is applicable to the type of apparatus used to fabricate the energy-storage device according to the teachings herein. One example of the substrate shape is a semiconductor wafer. Other forms of the substrate include elongate webs, weaves, foils, and sheets. It is within the scope of the present invention to provide a substrate having sufficient size on which a plurality of energy-storage devices and/or a plurality of energy conversion devices are fabricated.

One embodiment of the substrate 55, 309, or 709 includes a substrate that retains its support characteristics during an in situ temperature treatment. In the in situ temperature treatment, the substrate is placed in intimate contact with a thermally controlled surface, e.g., surface 715. In one embodiment, the thermally controlled surface is a cooled surface such that heat associated with deposition of any of the films described herein are thermally balanced so as not to thermally degrade the substrate or any other structural element previously formed on the substrate. Thus, in some embodiments, substrates having low thermal degradation temperatures, such as low melting points or low combustion temperatures, are used as substrates in the present fabrication methods. For example, substrates include ceramics, glasses, polymers, plastics and paper based materials. In an embodiment according to the teachings herein, the substrate is a plastic or metal substrate on which a plurality of energy-storage devices is deposited. The substrate is then divided into separate dies having at least one energy-storage device thereon. The dies then can be worked, e.g., cold worked, into a desired shape as dictated by the energy-storage device application.

In another embodiment, the substrate is made of a flexible material, e.g., substrate 709. The flexible substrate is formed into an elongate roll that is caused to pass over a curved object, which forces the material into intimate contact with the surface of the curved object. The curved object is a thermally controlled device (e.g., device 725 as shown in FIG. 7) to control the temperature of the substrate and balance the effect of heat generated on the substrate and films thereon during deposition. For example, the object is hollow and sealed from the environment of the deposition vessel. In some embodiments, the hollow space is filled with a coolant, e.g., cryogenic gas such as gas obtained from LN2 or liquid helium, with the coolant being constantly replenished. An area of intimate contact between the substrate and object is coincident and opposite the location of material impingement on the substrate from the deposition source. In another embodiment, the coolant is chilled water that is constantly being replenished. In another embodiment, the curved object is thermally controlled by an electro-thermal cooling apparatus. In another embodiment, the curved object is a drum, which is either stationary or rotatable about its axis in the direction of substrate movement.

In another embodiment, the substrate 55 or 309 is formed of a strip of rigid material. The rigid substrate is made to pass over a cooled, thermally controlled surface. Examples of the cooled surface are described herein. One such example is a cooled surface that is cooled by the release of cryogenic fluid such as liquid N2 or liquid helium into passages within the body of object having the surface but sealed from the environment of the deposition chamber. Other coolant sources include chilled water, cryogenic gas, and electro-thermal devices.

Figure 8:
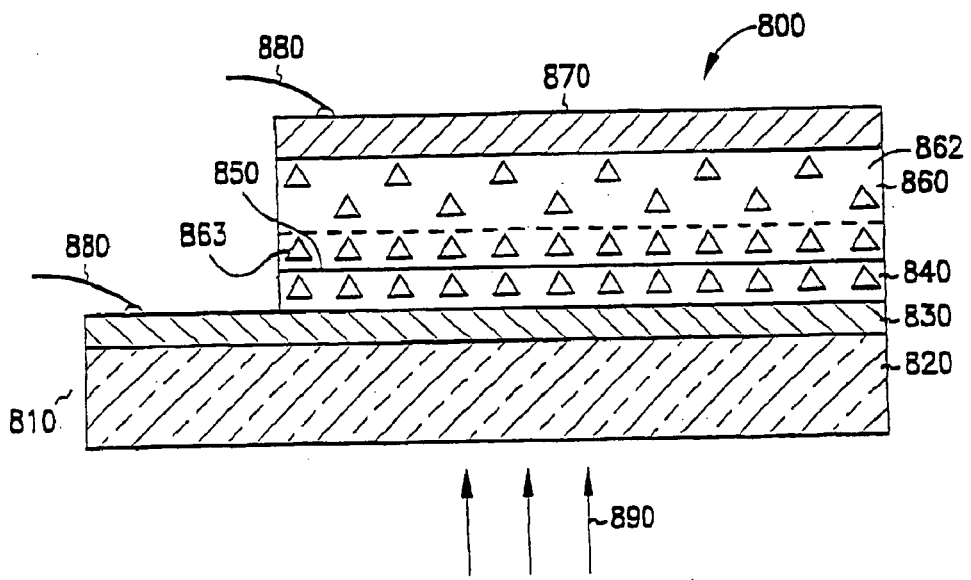
FIG. 8 is a cross-sectional view of a photovoltaic cell according to the teachings of the present invention.

FIG. 8 shows a photovoltaic cell 800, e.g., solar cell, that includes a transparent electrode 810. Transparent electrode 810 includes a transparent supporting film 820 and a transparent, electrically conductive film 830 formed on film 820. Examples of supporting film 820 include glass and transparent plastics. In some embodiments, conductive film 830 includes indium tin oxide or tin oxide. In use, light 890, enters solar cell 800 through the transparent electrode 810. In some uses of embodiments, light 890 is solar light. A first semiconductor film 840 is positioned in contact with the transparent electrode 810. A second semiconductor film 860 is positioned in contact with the first semiconductor film 840, thereby, forming a semiconductor junction 850. In some embodiments, second semiconductor film 860 includes a bulk, highly doped region 862 and a high quality region 863 adjacent the first semiconductor film 840. In this embodiment, the junction is formed by the first semiconductor film 840 and region 863. An electrical contact film 870 contacts the second semiconductor film 860. First and second conductive leads 880 respectively contact the transparent, electrically conductive film 830 and the electrical contact film 870 to carry power away from the cell.

In some embodiments, the materials and compositions of photovoltaic cell 800 are conventional CdS/CdTe materials such as is described in U.S. Pat. No. 4,207,119, which is incorporated by reference; with the additional processing according to the present invention to anneal or treat the surface (e.g., by ion-assist beam) of the films as they are deposited. In other embodiments, the compositions used are as described in the following publications, each of which is incorporated by reference: R. W. Birkmire et al, "Polycrystalline Thin Film Solar Cells: Present Status and Future Potential," Annu. Rev. Mater. Sci. 1997.27:625–653 (1997); T. L. Chu et al, "13.4% Efficient thin-film CdS/CdTe Solar Cells," J. Appl. Phys. 70 (12) (15 Dec. 1991); T. Yoshida, "Photovoltaic Properties of Screen-Printed CdTe/CdS Solar Cells on Indium-Tin-Oxide Coated Glass Substrates," J. Electrochem. Soc., Vol. 142, No. 9, (September 1995); T. Aramoto et al., "16% Efficient Thin-Film CdS/CdTe Solar Cells," Jpn. J. Appl. Phys. Vol. 36 pp 6304–6305 (October 1997); R. B. King, ed. "Encyclopedia of Inorganic Chemistry" Vol 3., pp 1556–1602, John Wiley & Sons Ltd., (1994).

The brief description of the operation of a heterojunction, photovoltaic solar cell that follows is to illustrate how the methodology of the present invention is applied to the fabrication of heterojunction, photovoltaic solar cells. It is believed that the present invention provides means and methods for fabricating photovoltaic cells having superior efficiency.

In a heterojunction photovoltaic cell, the semiconductor films are formed of different materials. For a rectifying junction, the semiconductor films must also be of different type, that is p or n type. The junction between the two semiconductor films is both a pn junction and a heterojunction. The first semiconductor film on which solar light is incident has a band gap higher than that of the second semiconductor film. The band gap of a semiconductor is the energy separation between the semiconductor valance band and the conduction band. The band gap of this first semiconductor film is chosen so that it corresponds to light in the short wavelength region of the solar spectrum. Photons of light having energy equal to or greater than the band gap of the first semiconductor film are strongly absorbed, but photons of light of energy less than the band gap of the first semiconductor pass through the first semiconductor and enter the second semiconductor film. Examples of materials used for the first semiconductor film include CdS, ZnS, CdZnS, CdO, ZnO, CdZnO, or other wide band gap semiconductors like SiC, GaN, InGaN, and AlGaN. The second semiconductor film is chosen from materials that have band gaps that correspond well to the long wavelength onset of solar radiation. Materials such as CdTe, CuInSe$_2$, InP, GaAs, InGaAs, InGaP, and Si are examples of materials for the second semiconductor film.

A "built in" electric field exists at the junction between the two semiconductor films due to the migration of majority carriers from one semiconductor type into the other. That is, electrons from the n-type semiconductor migrate into the p-type semiconductor leaving a net positive charge on the n-semiconductor side of the junction. The converse happens to the p-type semiconductor. Holes from the p-type semiconductor migrate into n-type semiconductor leaving a net negative charge on the p-semiconductor side of the junction. Absorption of a photon in one of the semiconductor films 840, 860 results in the creation of an electron and a hole. When the photon is absorbed in the vicinity of the pn junction, the built in electric field separates the two carriers in opposite directions, electrons are driven to the n-type material and holes are driven to the p-type film. The separated charges result in a potential difference between the two semiconductor films 840, 860. This potential difference is used to drive a current through an external circuit thereby converting solar energy (photons) into electrical energy.

One embodiment of a heterojunction, photovoltaic solar cell is an n-type, polycrystalline CdS film as the first semiconductor film 840 and a p-type, polycrystalline CdTe film as the second semiconductor film 860. CdS has a band gap of 2.43 eV that corresponds to 510 nm. CdTe has a band gap of 1.44 eV that corresponds to 860 nm. Solar radiation shorter than 860 nm and longer than 510 nm is absorbed in the p-type CdTe semiconductor film 860. Each absorbed photon creates an electron hole pair. If the minority carrier, the electron in p-type CdTe, has a lifetime sufficiently long so that it can drift to the pn junction and be swept across the junction to the n-type CdS film, the absorbed photon contributes to solar cell photocurrent. Minority carrier lifetimes in p-type CdTe are long, which results in high quantum efficiencies (number of electrons created per number of photons absorbed at a particular wavelength) of ~90% between 860 nm and 510 nm. Most photons absorbed in the CdTe film contribute to the solar cell photocurrent.

Solar light at wavelengths shorter than 510 nm is absorbed in the n-type CdS film and creates an electron-hole pair. Minority carriers in n-type CdS, holes, have short lifetimes. Most photogenerated holes recombine with electrons in the n-type CdS film before they can be swept across the junction to the p-type CdTe film. Recombined electron-hole pairs do not contribute to the solar cell photocurrent. Creation of electron-hole pairs by absorption of solar radiation in the CdS film is detrimental to the overall efficiency of the solar cell. High-efficiency solar cells make the CdS film as thin as possible, ~50 nm, so that some fraction of solar radiation shorter than 510 nm can pass through the CdS film and be absorbed in the CdTe film where the photogenerated electron-hole pairs can be efficiently collected. A problem with this procedure is that, in some embodiments, thinning the n-type CdS film increases the series resistance of the cell, which also decreases the efficiency. Additionally, the CdS film must have some reasonable thickness, ~50 nm, to form a stable pn junction.

The deposition methods according to the present invention are used to enhance the performance of heterojunction solar cells by creating higher quality semiconductor films 840, 860. In some embodiments, semiconductor films 840, 860 have structures that provide sufficiently long minority-carrier lifetimes to allow the minority carriers to be swept across the junction and contribute to the solar cell photocurrent. In some embodiments, higher quality films 840, 860 are produced by providing energy focused at the surface where a film is being formed. In some embodiments, the energy is supplied simultaneously with the material to be deposited on a substrate. In some embodiments, higher quality films are created by depositing the primary material, for example, CdS in the film 840, using a physical vapor deposition technique while impinging energized particles from a second source on the film surface during the deposition. In some embodiments, the second source includes an ion source. In some embodiments, the ion source provides a beam of ions. In some embodiments, the beam of ions includes argon or xenon. In some embodiments, the beam of ions includes sulfur for depositing sulfide materials. In some embodiments, the beam of ions includes oxygen for depositing oxide materials. The effect of supplying focused energy is to increase the extent of crystallinity of the material being deposited. Another effect of supplying focused energy is to decrease defects that provide sites for electron-hole recombination. A further enhancement of the solar cell efficiency is achieved by using the focused energy to control the quality of the physical interface between the first semiconductor film 840 and the second semiconductor film 860.

In an embodiment, the first film 840 is fabricated by providing energy to the material being deposited so that the material has fewer defects. With fewer defects the minority carriers will have longer lifetimes in film 840 as the will be fewer recombination sites. In some embodiments, first film 840 includes an n-type CdS material. In some embodiments, the first film 840 is formed in a range of about 40 nanometers to about 100 nanometers. In some embodiments, the first film 840 has a thickness of about 50 nanometers. In some embodiments, the first film 840 is formed in a range of about 40 nanometers to about 100 nanometers.

In some embodiments, the second film 860 includes two regions 862, 863. Region 863 is a high-quality region formed according to the teachings of the present invention. In some embodiments, region 862 is grown in a faster manner using conventional methods. In other embodiments, film 862 is merely a further growth of film 863 using the teachings of the present invention. High quality includes, among other things, fewer defects, larger crystal size, or certain structures being formed. Specifically, energy is supplied to the material of region 863 as the material is formed on the first film 840. The energy is supplied according to the teachings herein, for example, by an ion-assist beam. In some embodiments, the energy is supplied by energized particles. In some embodiments, the energy is supplied by energized ions. In some embodiments, the energy is supplied by light or heat, e.g., a brief laser sweep of the surface. Due to the application of energy while the region 863 is being formed, a post-deposition high-temperature anneal is not required.

In some embodiments, the high quality region 863 has fewer defects than p-type regions of other photovoltaics. In some embodiments, region 863 has a thickness of at least about 50 nanometers. In some embodiments, region 863 has a thickness in a range of about 50 nanometers to about 100 nanometers.

In some embodiments, region 862 is larger than region 863. In some embodiments, region 862 has a thickness of greater than 500 nanometers. In some embodiments, region 862 has a thickness in a range of 1 micron to 5 microns. In some embodiments, region 862 has a thickness of greater than 3 microns. In addition, region 862 is a highly doped p-type material.

In some embodiments, a chamber in which the films 840, 860 are being deposited is held at a temperature of less than 650 degrees Celsius. In some embodiments, the temperature of the chamber is less than about 300 degrees Celsius. In some embodiments, the temperature is between about 30 degrees Celsius and about 275 degrees Celsius. In some embodiments, the temperature is between about 100 degrees Celsius and about 200 degrees Celsius. In an embodiment, the substrate, e.g., glass layer 820 and conductor layer 830 for depositing film 840; glass layer 820, conductor layer 830, and film 840 for depositing region 863; and glass layer 820, conductor layer 830, film 840, and region 863 for depositing region 862, is not externally heated. Thus, the temperature of the substrate is generally equal to the temperature of the chamber plus minor heating effects of depositing the film. In contrast to prior methods for fabricating layers having sufficient quality such that the cell approaches about 10 percent efficiency, an embodiment of the present invention does not heat the substrate. Accordingly, manufacturing efficiencies are achieved while maintaining sufficient efficiency.

It is believed that some embodiments of the present invention will have conversion efficiencies of greater than about 5 percent. It is believed that some embodiments of the present invention will have conversion efficiencies of greater than about 6 percent. It is believed that some embodiments of the present invention will have conversion efficiencies of greater than about 7 percent. It is believed that some embodiments of the present invention will have conversion efficiencies of greater than about 8 percent. It is believed that some embodiments of the present invention will have conversion efficiencies of greater than about 9 percent. It is believed that some embodiments of the present invention will have conversion efficiencies of greater than about 10 percent. It is believed that some embodiments of the present invention will have conversion efficiencies of greater than about 11 percent.

Other embodiments for fabricating energy conversion devices, such as a photovoltaic cell 800, are fabricated according to many of the embodiments described herein with reference to energy storage devices. The thin films of the energy conversion devices are improved in a similar manner as described herein for the thin films of energy storage devices.

In contrast to some conventional methods for improving performance of a photovoltaic cell, the present methods can produce photovoltaic cells having an enhanced conversion efficiency without heat treating during deposition, e.g., heating the substrate, or a post-deposition high temperature anneal.

Figure 9A:
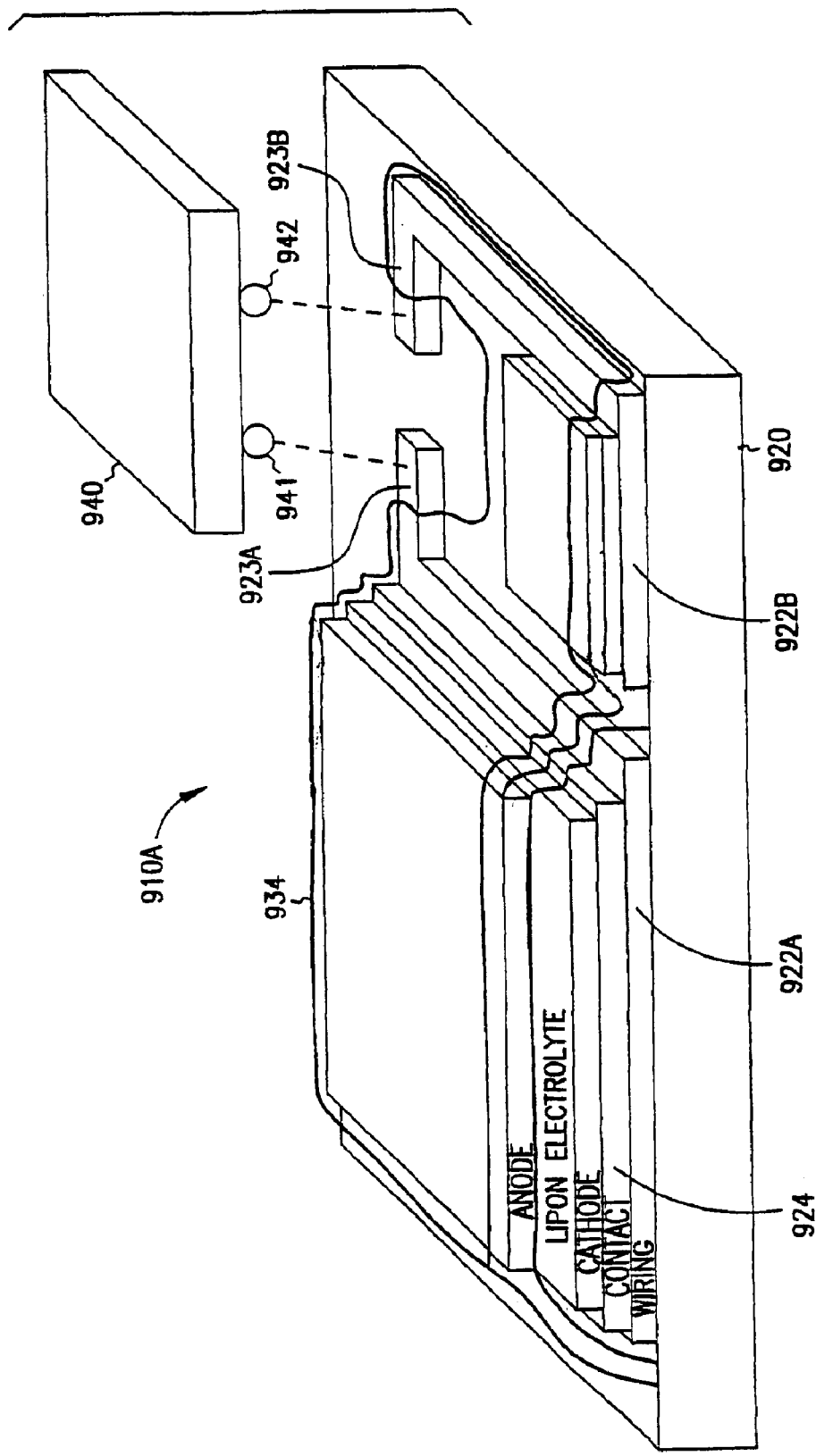
FIG. 9A is a perspective view of a thin-film energy-storage device according to the teachings of the present invention.

FIG. 9A shows a thin-film energy-storage device 910A according to the teachings of the present disclosure and an integrated circuit 940, here shown as a "flip chip". Energy-storage device 910A includes substrate 920 on which is formed a patterned wiring layer 922. The wiring layer 922 is an electrically conductive layer for connecting energy-storage device 920 to the integrated circuit 940. In some embodiments, layer 922 is formed of a metal. In one embodiment, the wiring layer 922 is patterned copper. In another embodiment, the wiring layer is formed of nickel. In other embodiments, the wiring layer is formed of a noble metal. Wiring layer 922 includes a cathode wiring pattern 922A and an anode wiring pattern 922B, which are separate from each other and form opposite polarity connectors 923A and 923B to external circuitry, such as integrated circuit 940. Device 910A further includes a cathode contact film 924 formed on at least a portion of cathode wiring pattern 922A and an anode contact film 926 formed on at least a portion of the anode wiring pattern 922B. A cathode film 927 is formed on the cathode contact film 924 according to the teachings herein. An electrolyte film 928 is formed over the cathode film 926, cathode contact film 924 and a portion of the cathode-wiring pattern 922A. Electrolyte film 928 separates the cathode films 922A, 924 and 927 from respective anode films 922B, 926 and 932. Anode film 932 is formed on the electrolyte film and in contact with the anode contact film 926 according to the teachings herein. It will be appreciated that, in one embodiment, cathode contact film 924 and cathode wiring pattern 922A are formed as a single layer. It will be further appreciated that, in one embodiment, anode contact film 926 and anode wiring pattern 922B are formed as a single layer. A passivation layer 934 is formed over all of the films except portions 923A and 923B of the wiring patterns 922A and 923B, which portions are left exposed. Passivation layer 934 protects the films from contact to other layers, which may be formed on substrate 920, and the environment, which may include elements that may react with and damage the films of the energy-storage device 910A.

In some embodiments, the cathode materials and other materials used in the batteries above include materials discussed more in N. J. Dudney et al, "Nanocrystaline $Li_xMn_{1-y}O_4$ Cathodes for Solid-State Thin-Film Rechargable Lithium Batteries," Journal of the Electrochemical Society, 146(7) 2455–2464 (1999) which is incorporated by reference.

The integrated circuit 940 includes a first ball contact 941 and a second ball contact 942 both extending outside a package. The first ball contact 941 aligns with the exposed portion 923A of the cathode wiring pattern 922A. The second ball contact 942 aligns with the exposed portion 923B of the anode wiring pattern 922B. Integrated circuit 940 is positioned so that the ball contacts 941 and 942 physically and electrically contact the wiring contacts 923A and 923B, respectively. Integrated circuit 940 is fixed in position relative to the device 910A such that device 910A provides electrical energy to circuit 940. In some embodiments, circuit 940 is provided with circuitry for recharging energy-storage device 910A. It will be recognized that the present invention is not limited to only integrated circuit 940 being connected to wiring contacts 923A and 923B. Other circuits, including integrated circuits fabricated on substrate 920 and circuits with leads connected to wiring contacts 923A and 923B, are within the scope of the present invention.

Figure 9B:
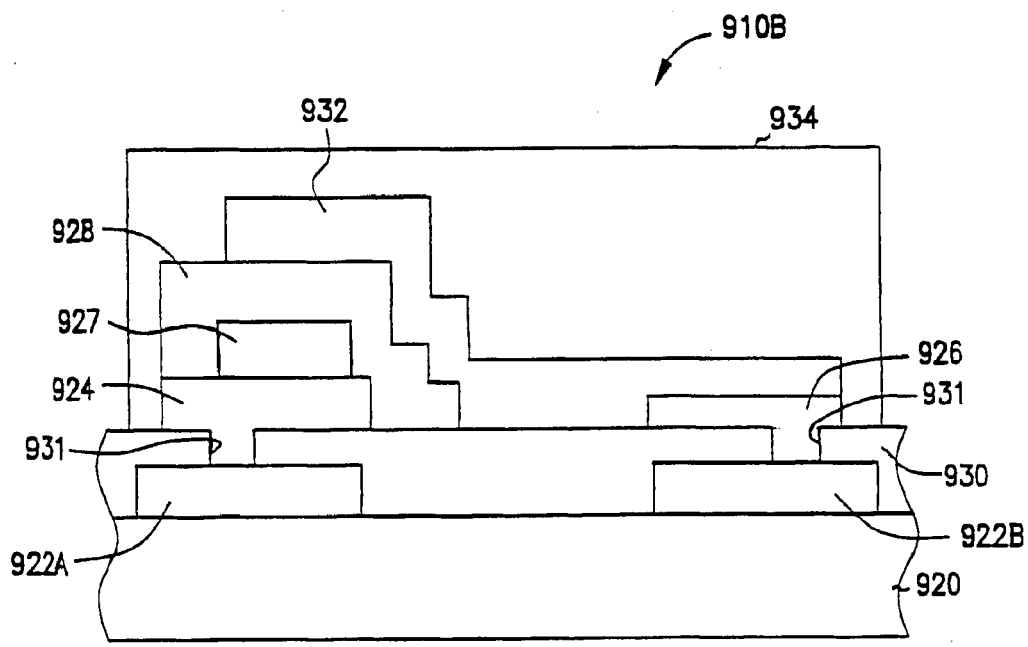
FIG. 9B is a view of another embodiment of a thin-film energy-storage device according to the teachings of the present invention.

FIG. 9B shows another embodiment of the thin-film energy-storage device 910B, substantially similar elements to those described above are designated by the same reference numerals. After forming wiring patterns 922A, 922B, an insulator layer 930 is formed on the substrate 920. Insulator layer separates the thin-film energy-storage device 910 from other layers that may be included with substrate 920. Insulator layer 930 includes vias 931 through which cathode contact film 924 and anode contact film 926 extend downward to connect to cathode contact wiring pattern 922A and anode wiring pattern 922B, respectively.

In one example of an energy-storage device 910 according to the present invention, the cathode film 927 is a LiCoO2 deposited using a first source of LiCoO with a secondary source of oxygen. The electrolyte film 928 is LiPON deposited using a first source of LiPO (such as Li3PO4) and an assist of nitrogen. The anode film 932 is a metal, e.g., copper, and is deposited by a first source of copper and a secondary source of an inert material, e.g., xenon. In another embodiment, the anode film includes carbon. In yet another embodiment, the anode is formed of pure lithium. In some embodiments, the anode is a lithium alloy. In some embodiments, the anode includes an oxide.

Figure 9C:
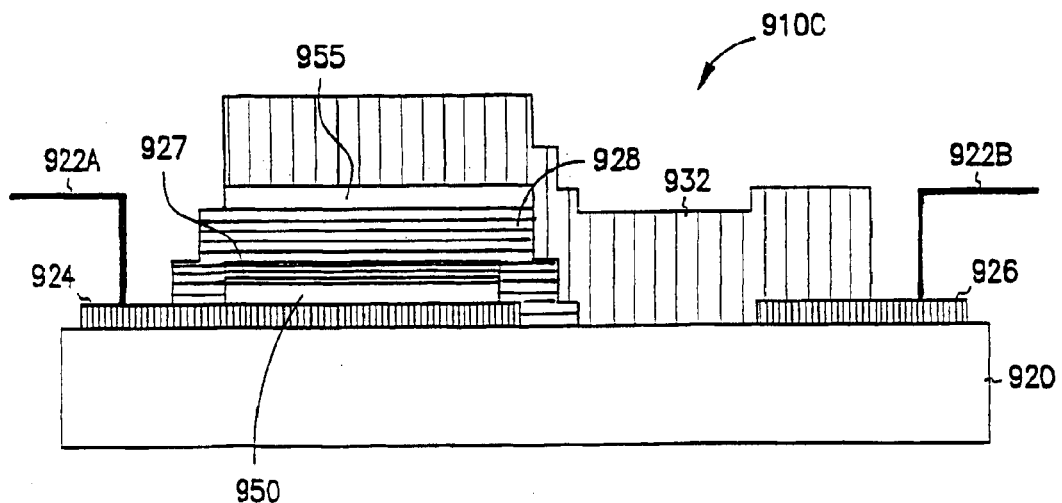
FIG. 9C is a view of another embodiment of a thin-film energy-storage device according to the teachings of the present invention

FIG. 9C shows a further embodiment of a thin-film energy-storage device 910C. This device 910C includes a seed layer 950 formed on the cathode contact 924. Seed layer 950 is formed on the cathode contact 924 prior to forming the cathode film 927, as described herein, on the seed layer 950 and substrate 920. Seed layer 950 is formed using deposition techniques as described herein, e.g., physical vapor deposition such as arc source deposition. Seed layer 950 is a very thin, electrically conductive layer and has a small crystal size. The seed layer 950 also has a high sheet resistance and is non-reactive with the materials of adjacent films. In an embodiment, seed layer 950 has a thickness that is substantially thinner than the adjacent electrode film 927. The material of the seed layer 950 is chosen such that the arriving adatoms of the subsequent material (e.g., in some embodiments, the material from the first source 311, 511 or 711) would have sufficient mobility to allow a period of activity once the adatom contacts the seed layer surface. This improves nucleation of the first few molecular layers of arriving material, minimizes strain associated with lattice mismatch and assists the arriving material to grow in a manner consistent with the desired crystal structure for cathode film 927.

In some embodiments, a seed layer 955 is formed on the electrolyte layer 928 prior to forming anode film 932, as described herein, on the seed layer 955. Seed layer 955 improves nucleation of the first few molecular layers of arriving material, minimizes strain associated with lattice mismatch and assists the arriving material to grow in a manner consistent with the desired crystal structure for anode film 932.

The ion transport properties of the materials used in the fabrication of energy-storage devices 910C, e.g., rechargeable batteries, greatly influence the operation and quality of the device. For example, the total energy-storage capability of solid-state, lithium-ion batteries of a given area is limited by a depletion region that forms at or near the cathode/electrolyte interface. The depletion of this region and the inability for additional lithium ions to be transported out of the bulk of the cathode film 927 results in limited capacity and, thus, more frequent recharges. Additionally, the efficiency of the lithium ion transport through the electrolyte film 928 controls and dictates the maximum discharge rate that can be achieved for a given structure. The seed layer 950 improves the crystalline structure of the materials subsequently deposited, i.e., a cathode film 927 or an anode film. The growth of the first few atomic layers of a material significantly impacts its overall structure even when the final film is very thick relative to the initial few atomic layers. If the "seed" material is chosen such that the surface energy kinetics are conducive to pseudo-epitaxial growth of the subsequent material, high quality cathode and anode (electrode) films 927 and 932 are achieved. Examples of materials for seed layer 950 include chromium, chromium nitride, tantalum, tantalum nitride, tungsten, tungsten nitride, ruthenium and ruthenium nitride.

The thin-film energy-storage device fabricated according to the present teachings stores electrical energy by introducing ions into a storage layer and removing the ions from the storage layer to create an electrical potential at the contacts. In one embodiment, lithium ions are stored in an anode formed of a lithium-intercalation material with the battery in a charged state. In some embodiments, the anode is formed of a metal or a carbonaceous material. The lithium ions travel from the anode through the electrolyte layer to a cathode, which is also formed of a lithium-intercalation material, to discharge electrical energy from the battery. In order to achieve sufficient energy density to operate external circuitry, the lithium-intercalation material cathode and anode must intercalate (i.e., add) and de-intercalate (i.e., remove) of a substantial mole fraction of lithium ions. It has been found that the choice of intercalation material and fabrication techniques for the cathode determine many operating parameters of a solid-state, thin-film battery. The operating parameters include, but are not limited to, operating voltage range, capacity, specific power, and specific energy. One method of measuring the transport properties of ions in a battery is diffusivity, which is measured by a diffusion coefficient. The diffusion coefficient is a measure of how well a particular material allows ions to diffuse into and out of the material.

Figure 10:
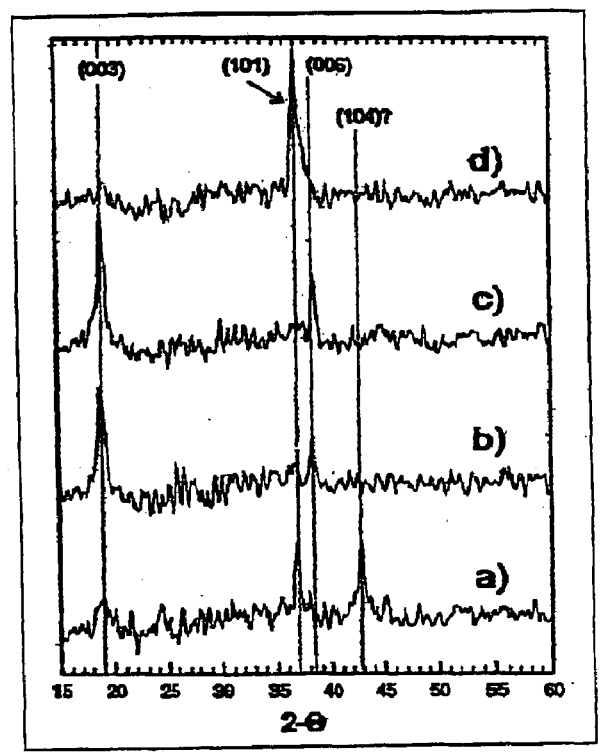
FIG. 10 shows X-ray diffraction spectra of cathode films for thin-film batteries.

FIG. 10 shows comparative data for LiCoO2 cathode films in the form of X-ray diffraction spectra. The LiCoO2 cathode films were created according to the teachings herein and according to a control process that did not include a secondary source assist. A first source supplied a LiCoO2 material using an electron-beam evaporation process. An assist, second source provided energy in the form of oxygen ions impinging at the location on the substrate whereat it is desired to grow a thin electrode (cathode) film from the LiCoO2 first material. The beam of oxygen ions from the second source is not co-incident with the LiCoO2 material from the first source. Four samples of LiCoO2 thin films were grown according to the data in Table I.

TABLE I

| Deposition Parameters | Film a | Film b | Film c | Film d |
| --- | --- | --- | --- | --- |
| Electron beam power* (W) | 500 | 500 | 500 | 500 |
| Total gas flow, $O_2$ + Ar, (sccm) | 0 | 10.8 | 10.8 | 10.8 |
| $O_2$ gas ratio, $O_2/(O_2$ + Ar), (%) | NA | 0.48 | 0.48 | 0.48 |
| Chamber pressure (Torr) | $9.2 \times 10^{-7}$ | $2.6 \times 10^{-6}$ | $3.7 \times 10^{-6}$ | $5.0 \times 10^{-6}$ |
| Ion source power (W) | 0 | 123 | 128 | 135 |
| Ion source acceleration voltage (V) | 0 | 41 | 64 | 135 |

The electron beam voltage for each first source used in forming films a-d is 5 kV with an emission current of 100 mA.

FIG. 10 shows that the $LiCoO_2$ films deposited with lower energy oxygen ions from the second source, samples "b" and "c", enhanced the formation of the desirable crystallite structure of the grown film relative to the non-assisted sample "a". Specifically, a more distinct (003) orientation of the crystal structure is found in ion-assisted samples "b" and "c" than in non-assisted sample "a". A strong (003) X-ray diffraction peak indicates one desired crystal orientation of the $LiCoO_2$ thin film. The (003) X-ray diffraction peak indicates that the film has lattice planes parallel to the substrate, e.g., layer on which the film was deposited. The (003) peak width, full width at half maximum ("FWHM") decreases and the X-ray peak increases in this series of samples as the energy of the oxygen ions impinging the deposited material increases. These examples indicate an increasing crystallite grain size and a larger fraction of ordered grains for sample films "b" and "c" than are found in sample film "a". The (003) orientation of samples "b" and "c" is preferable over an essentially non-ordered, non-crystallized structure of sample "a".

FIG. 10 further shows a sample "d" that was deposited using the highest energy secondary source of this example. Sample "d" was deposited using a secondary source energy of 135 eV. X-ray diffraction of sample "d" shows it has the most distinct (101) orientation of all the samples described herein. The desired (101) orientation has lattice planes, which contain lithium ions in a LiCoO electrode material, nearly perpendicular to the substrate. In this orientation, the lattice planes are essentially parallel to the direction of travel of the ions and in the direction nearly perpendicular to the substrate. As this is the direction lithium ions must travel in a lithium battery fabricated according to the embodiments described herein, the preferential (101) orientation leads to superior charging and discharging characteristics. As lithium transport through the $LiCoO_2$ film in the (101) preferential orientation does not rely on diffusion along grain boundaries, which can trap lithium ions and prevent their utilization, the preferential (101) orientation also leads to greater capacity and cycle lifetime. Consequently, this preferred orientation of the $LiCoO_2$ thin film is produced without additional anneal fabrication steps and the internal resistance is lower with lower capacity loss at high discharge rates.

Figure 11:
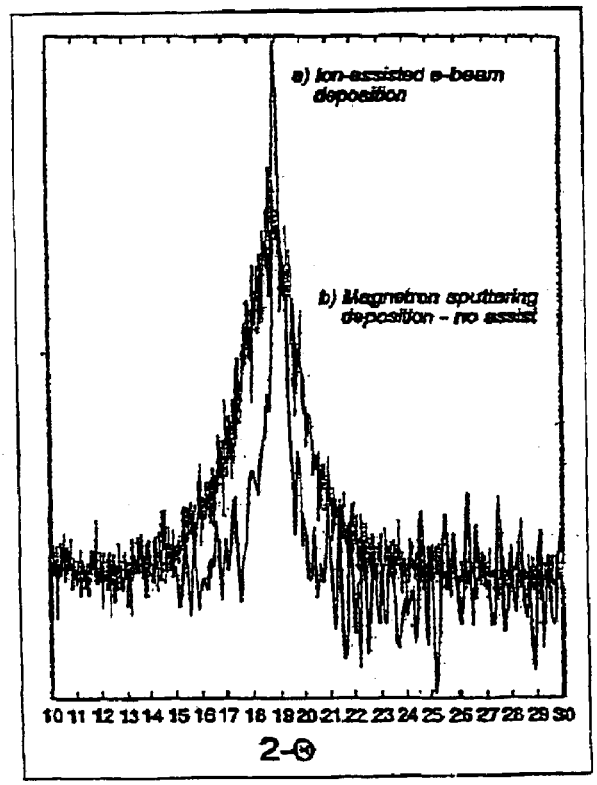
FIG. 11 shows X-ray diffraction spectra of both a conventional cathode layer and a cathode film according to the teachings of the present invention.

FIG. 11 shows a comparison of the (003) x-ray diffraction peak of an ion assisted $LiCoO_2$ film fabricated according to the teachings of the present invention and a conventionally magnetron sputtered $LiCoO_2$ film. Both spectra are for as-deposited films. The ion assisted $LiCoO_2$ film in this spectrum is the same as the "c" sample shown in FIG. 10. The sputtered $LiCoO_2$ film was fabricated in an MRC 8667 using 1200 watts RF power, 10% $O_2$ in Argon, 80 sccm total gas flow (8 sccm $O_2$ and 72 sccm Ar), 20 mTorr pressure, with the substrate table grounded. Film thickness of the sputtered $LiCoO_2$ film is 5460 Angstroms. The significantly sharper peak for the ion-assisted film indicates the higher degree of long range order in this film. The peak width for this film is approaching that obtained by high temperature annealing of a similar conventionally magnetron sputtered film and exceeds that achieved for 300 degree Celsius annealed films of $LiMn_2O_4$. Accordingly, the $LiCoO_2$ film fabricated according to the teachings of the present invention provides a higher degree of order than conventional $LiCoO_2$ films without resorting to a post deposition anneal step to provide the desired crystal structure in the film. This results in significant manufacturing efficiencies.

Figure 12A:
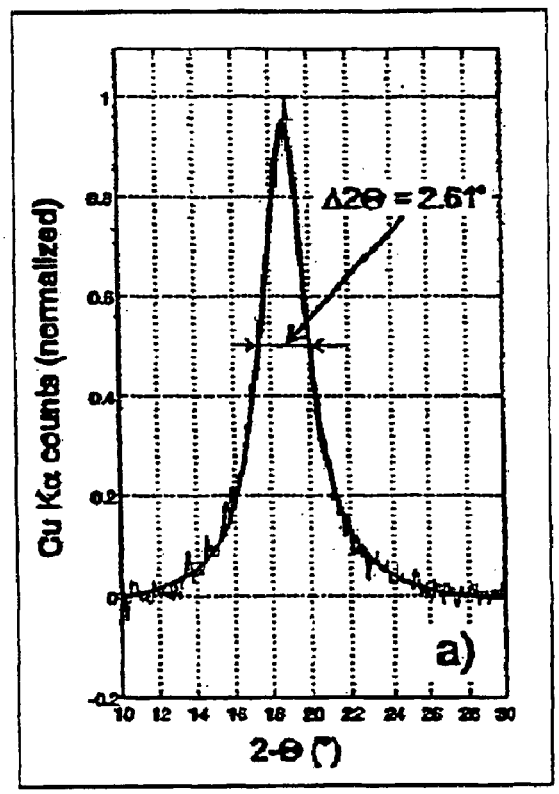
FIG. 12A shows X-ray diffraction spectra for a conventional magnetron sputtered cathode layer.

FIG. 12A shows a X-ray diffraction spectra of a $LiCoO_2$ layer fabricated according to a conventional method of magnetron sputtering without the subsequent anneal step. The magnetron sputter was performed in MRC 8667 sputter, with 1200 W of RF power, in an environment of argon with 10% oxygen and 80 sccm total gas flow, at a pressure of 20 mTorr. The resulting film thickness is 5460 Angstroms. The x-ray peak full width at half maximum ("half height width") of the peak at 19 degrees of this conventional sample is 2.61 degrees. The half height width is a measure of the crystallite size, which can be calculated from this data as according to known formulas. The crystallite size for this conventionally magnetron sputtered film is 34 Angstroms. This conventional film must be annealed at high temperature to achieve sufficient crystallite size to have adequate electrical properties such that the film is part of a functional and practical battery.

In other conventional film materials, like $LiMn_2O_4$, nanocrystalline structures have been sputtered into films and prior to their anneal they have a crystallite size of about 40 Angstroms to about 50 Angstroms. Annealing this film at a temperature of about 300 degrees Celsius produces a crystallite size of about 130 Angstroms to about 160 Angstroms. In some embodiments of the present invention, these crystallite sizes are achieved at the time of deposition. Moreover, in some embodiments, superior crystallite sizes are achieved at the time of deposition.

Figure 12B:
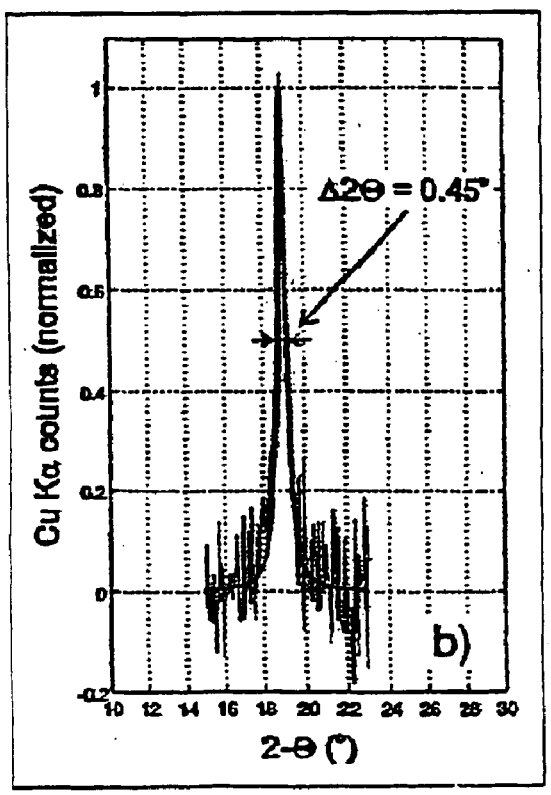
FIG. 12B shows X-ray diffraction spectra for a thin film for an energy-storage device according to the present disclosure.

FIG. 12B shows an X-ray diffraction spectrum for a $LiCoO_2$ film fabricated according to the teachings of the present disclosure. Specifically, this film was deposited using a first source and a secondary source of energized ions as discussed above with respect to samples "b" and "c" of FIG. 11. The peak for the ion assisted deposition film is significantly higher than the non-assisted spectra of FIG. 12A. This indicates a higher degree of long range order in the ion assisted deposition film. The half height width of the peak of the ion-assisted film at 19 degrees is 0.45 degrees. The crystallite size is 242 Angstroms. Accordingly, the present fabrication techniques yield an as deposited film having a crystallite size of greater than seven times that of the conventional deposition methods without post-deposition anneal. Moreover, the present fabrication techniques yield a superior crystallite size even when compared to the conventional film after it has been annealed. The present fabrication technique yields a factor of crystallite size improvement of about a 1.8 to about a 2.6 over the conventional technique. Consequently, the present fabrication method can thus achieve superior crystallite size in the film as they are deposited resulting in faster, more efficient fabrication of thin-film batteries. Such an improved crystallite structure is highly desirable in the cathode film due to the limitations imposed on energy storage in thin-film batteries due to cathode film performance.

Another aspect of the present fabrication method is the ability to fabricate thin films at essentially room temperature with a crystalline orientation that is essentially perpendicular to a boundary with adjacent films and crystallite size. Ions must travel through these boundaries to charge and discharge the battery. The boundaries include a first boundary that is between the cathode film and the electrolyte film and a second boundary that is between the electrolyte film and the anode film. The crystallite orientation is preferably perpendicular to the boundary planes. That is, the lithium ion lattice planes are parallel to the lithium ion direction of travel during charging and discharging the thin-film battery. This orientation lowers the internal battery resistance and lowers capacity loss at high discharge rates. The crystallite size is preferably large, e.g., over 100 Å, and more preferably over 200 Å. The larger the crystallite size improves electrical properties. Crystallite size is strongly correlated to the ion diffusion coefficient, a measure of how freely lithium ions can be added to, or extracted from the intercalation material.

While the above-described embodiments focus on lithium-intercalation materials and, more specifically, $LiCoO_2$, it will be recognized that the some embodiments are adaptable to other intercalation materials for producing energy-storage devices. Other types of intercalation material include $LiMn_2O_4$, $V_2O_5$, and carbonaceous materials, lithium, lithium alloys, oxides, and nitrides.

Using the fundamental teachings herein, i.e., the in situ assist of the growing film with appropriate energy and/or species of ionized gasses, processes involving the manufacture of photovoltaic panels, supercapacitors/ultracapacitors, and fuel cells could be made more robust and efficient. A corresponding cost, fabrication efficiency, and performance advantage can be gained.

For example, Solid Oxide Fuel Cells (SOFC) require the manufacturer to deposit a ceramic material on a support structure. See U.S. Pat. No. 6,007,683, incorporated herein by reference. This ceramic is then coated with a conductive material such as platinum, which is the catalyst for the fuel cell. The cost of these materials and the efficiency with which they conduct the appropriate ions from one side of the cell to the other determines, in large measure, the cost of manufacture and operation of the fuel cell. The application of the techniques described herein to a fuel cell manufacturing process would yield substantially higher quality catalyst with higher ionic transport capability. Moreover, the present techniques further provide the ability to produce a thinner catalyst by virtue of the structural properties of materials deposited via the methods described herein. This allows lower temperature operation of the fuel cell, thus, widening product latitude.

Supercapacitor/ultracapacitor performance is also enhanced by the application of the present techniques. See e.g., U.S. Pat. No. 5,426,561, incorporated herein by reference. High energy density and high power density ultracapacitors and supercapacitors are improved by reduction in crystalline defects and improvement in the growth mechanism such that the electrolyte layer could be significantly thinned. This thinning improves the volumetric energy density of the device. The improved crystal structure enhances the voltage stability of the electrolyte.

While some of the above embodiments include an ion source for providing the focused energy to arriving adatoms at a surface of a substrate to form films having fewer defects and/or certain crystal properties, other source of the focused energy are within the scope of some embodiments of the present invention. Examples of such other sources include high intensity photo sources, lasers, short duration, high intensity (flash) heat sources, short duration plasma sources. Each of these sources provides the required energy to a film and does not harm previously deposited layers, previously connected devices, or the substrate. In some embodiments, these sources provide the energy to the adatoms as they arrive at the surface on which the adatoms will form a film.

By way of introduction, one aspect of the invention deals with the field of batteries and, more specifically, to the use of a thin film battery for enclosures for devices and also for devices which include an integrated battery.

Figure 13:
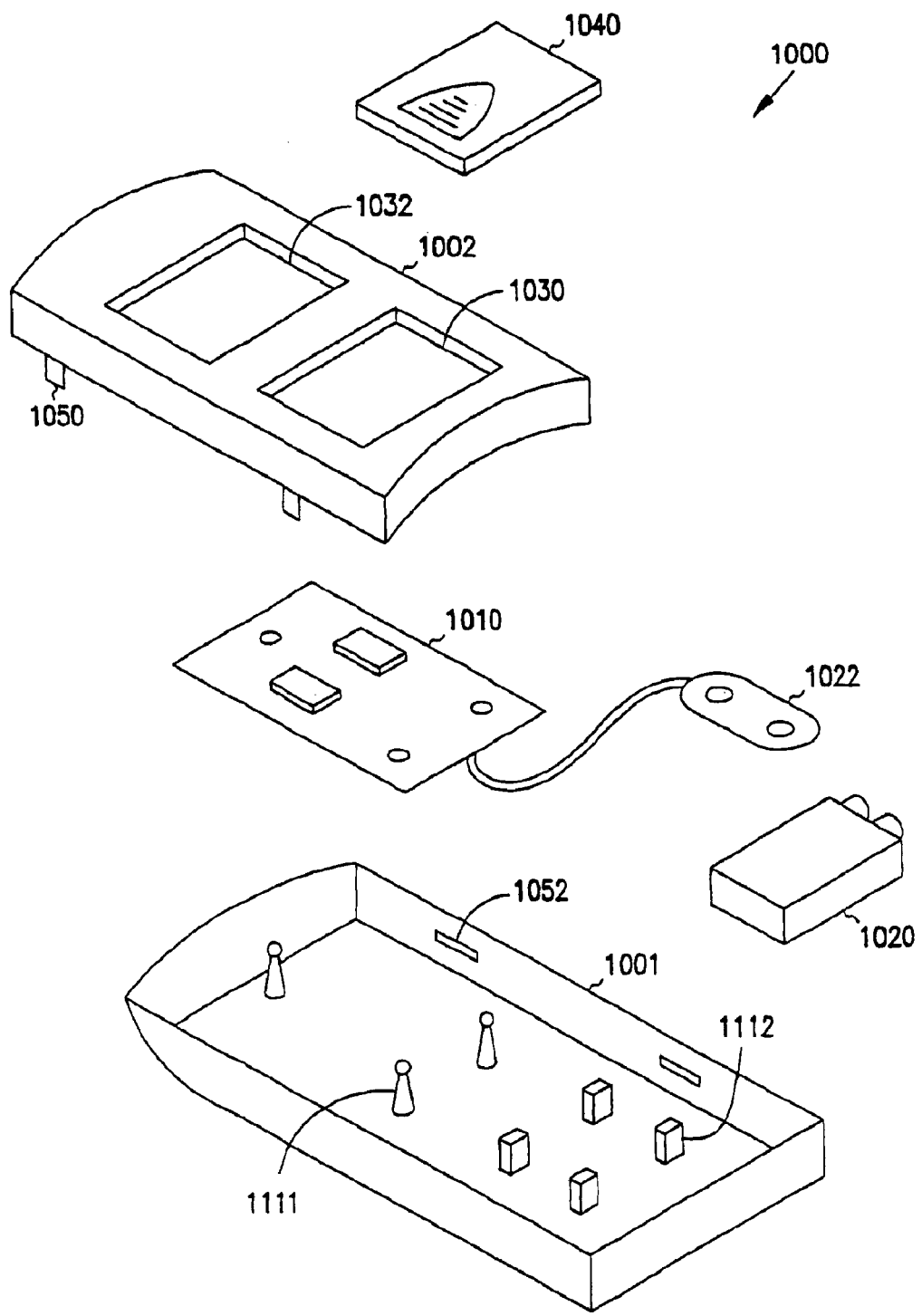
FIG. 13 is an exploded perspective view of an electronic device with a separate printed circuit board and battery.

FIG. 13 is an exploded perspective view of an electronic device 1000 having a separate printed circuit board 1010 and a separate battery 1020. The enclosure 1000 typically includes a first portion 1001 and a second portion 1002. The first portion 1001 may also be termed as a bottom portion and typically may include pegs 1011 upon which the printed circuit card 1010 rests. The pegs 1111 are also used to position the printed circuit card 1010 with respect to the bottom portion 1001 of the enclosure 1000. In addition, there are typically several other sets of stops 1112, which are used to position the battery 1020 with respect to the bottom portion 1001 of the enclosure 1000. The second portion 1002 will include openings 1030 and 1032. The opening 1032 may be for a display such as an LCD or liquid crystal display (not shown in FIG. 13). The opening 1030 is typically for an access panel 1040, which fits within the opening 1030. The access panel 1040 provides access to the battery 1020. The printed circuit board 1010 includes a battery connector 1022, which fits over the terminals of the battery 1020. The battery connector 1022 provides an appropriate amount of current to the electrical components on the printed circuit board 1010. The second portion 1002 of the enclosure 1000 includes several plastic hooks, which are used to mate the second portion 1002 with the first portion 1001 to form the enclosure 1000. The prongs or hooks 1050 fit within corresponding slots 1052 on the first portion 1001 of the enclosure 1000.

These enclosures are typically made of plastic, and housed within the enclosure 1000 is a separate battery 1020 and a separate printed circuit board 1010. These particular types of devices have several problems. First of all, the whole housing or enclosure, or at least a portion of it, has to be removed in order to replace a battery or in order to recharge a battery. The batteries 1020 typically include a gel-type electrolyte which can be very toxic and dangerous and, for that reason, difficult to dispose. From a manufacturing standpoint, there is a need to assemble many parts, including the separate circuit board 1010 and a battery 1020 and an LCD (not shown). These also must be accurately placed within the first portion 1001 to produce a quality-looking enclosure 1000 for the entire electrical device. Each time a separate component must be placed together or into one portion or a first portion of the device requires an additional process step. In addition, mating the second portion 1002 of the enclosure 1000 with the first portion 1001 is still a further process device. From a manufacturing point, it would be advantageous if there were less process steps involved in manufacturing an electronic device such as the one shown. With less manufacturing steps, the device can be made more simply and more cost effective.

Still a further disadvantage is that the separate components, such as the separate printed circuit card 1010 and the separate battery 1020, require a lot of space in terms of the enclosure. The tendency these days is to form electronic products or electronic devices that save on space. In most instances, a smaller electronic device is better than a larger electronic device. Therefore, there is a need for a process that can reduce the number of process steps and save on space and yet produce a reliable battery and circuit for an enclosure.

The above-described method (see FIGS. 1–12) for placing a battery onto a substrate can be used in many different ways in devices to produce a more compact and reliable electronic package having a battery which is capable of being recharged a very large number of times. The batteries and electronics could be placed directly onto an enclosure portion therefore saving space. As a result, the design of the various electronic devices could be smaller than corresponding devices that are currently used.

Figure 14A:
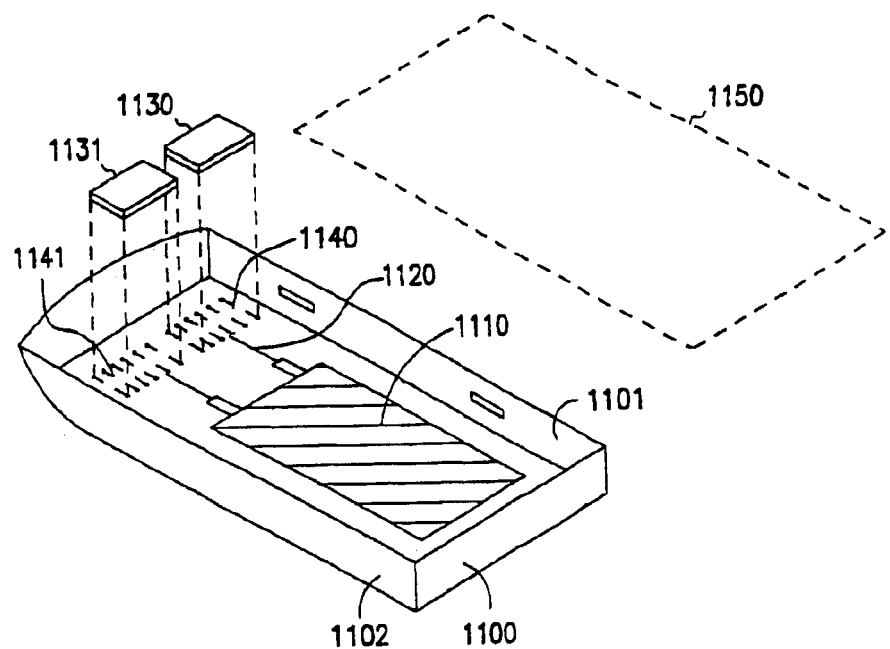
FIG. 14A is an exploded perspective view of a portion of an enclosure for an electronic device according to one embodiment of this invention.

FIG. 14A is an exploded perspective view of a portion of an enclosure that includes both a battery 1110, which is deposited directly onto the enclosure portion 1100. The enclosure portion 1100 includes an interior surface 1101 and an exterior surface 1102. In this particular embodiment, the battery 1110 is deposited onto the interior surface 1101 of the enclosure portion 1100. It should be noted that the enclosure portion 1100 resembles the first portion 1101 or the bottom portion, as shown in FIG. 13. The interior 1101 of the enclosure portion 1100 also includes a plurality of traces 1120 for electrically coupling the battery 1110 to various electronic components 1130, 1131, which are attached to sites 1140 and 1141. The sites 1140 and 1141 include the electrical contact pads for electrically connecting the electrical components 1130 and 1131 to the sites 1140 and 1141. The pads associated with the sites 1140, 1141 are also directly deposited onto the interior surface 1101 of the enclosure portion 1100. Advantageously, the battery 1110 can be deposited onto the interior portion 1101 of the enclosure portion 1100 as well as the traces 1120 and the pads associated with the sites 1140 and 1141. Advantageously, in order to complete an electronic circuit, the only process steps that need to be accomplished are to add the electronic components 1130 and 1131. In some instances it also may be possible to produce some of the electronic components during the manufacturing steps required to place the thin film battery 1110 onto the interior portion 1101 of the enclosure 1100. Optionally, a protective layer 1150 may be placed over the battery 1110 or other select portions deposited on the interior surface 1101 of the device enclosure 1100. The optional protective layer is shown in phantom and is referenced by reference numeral 1150.

Figure 14B:
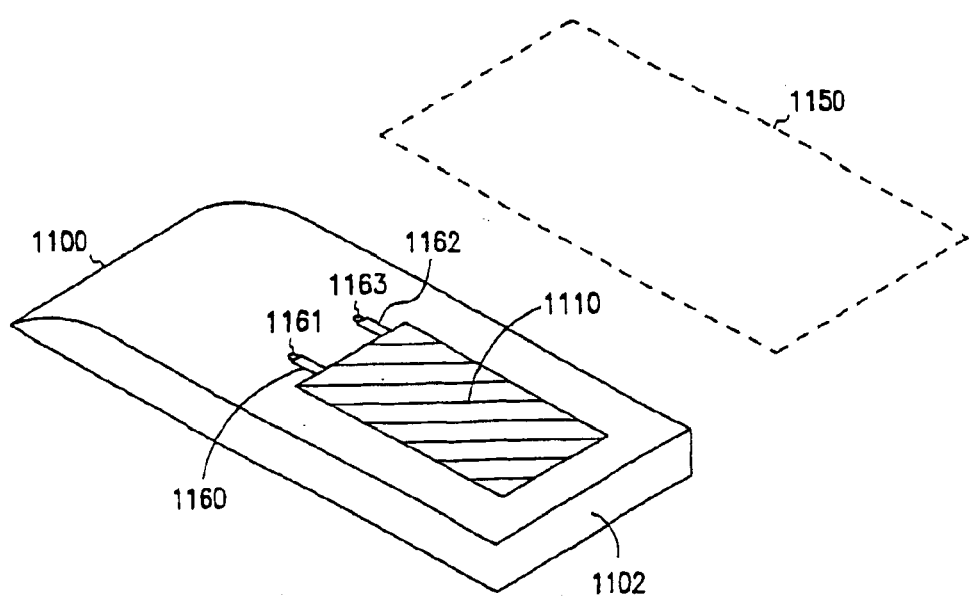
FIG. 14B is an exploded perspective view of a portion of an enclosure for an electronic device according to another embodiment of this invention.

FIG. 14B is an exploded perspective view of a portion 1100 of an enclosure for an electronic device according to another embodiment of this invention. The enclosure portion 1100 includes an interior and an exterior surface 1102. In this particular embodiment, the battery 1110 is deposited on the exterior surface 1102 of the enclosure portion 1100. The battery 1110 includes a post 1160 for the cathode and another post 1162 for the anode. The posts 1160 and 1162 terminate or attach to through holes 1161 and 1163. The through holes 1161 and 1163 provide electrical communication to various components located inside the enclosure portion 1100. In essence, the chief difference between the embodiment shown in FIG. 14A and the embodiment shown in this FIG. 14B is that the battery portion 1110 is deposited on the exterior surface 1102 of the enclosure portion 1100. A protective coating 1150 may be placed over the battery portion 1110 and, more specifically, over the battery portion 1110 and the electrical posts 1160 and 1162 and the through holes 1161 and 1163. The protective layer 1150 may be translucent or may be colored to match the exterior surface 1102 of the enclosure portion 1100.

Figure 14C:
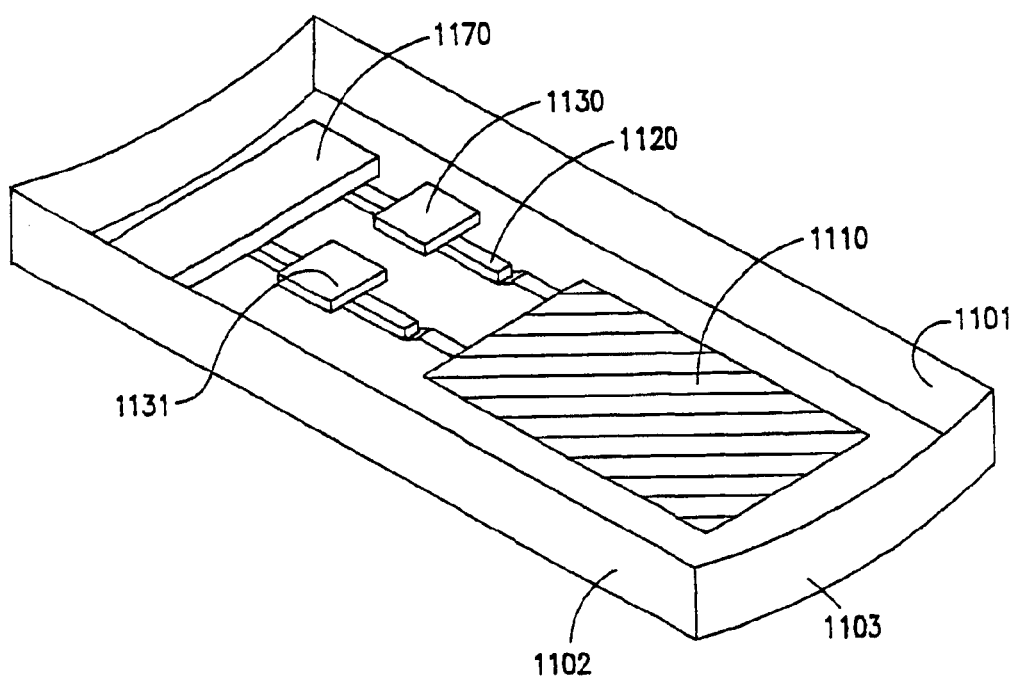
FIG. 14C is an exploded perspective view of a portion of an enclosure for an electronic device according to yet another embodiment of this invention.

FIG. 14C is an exploded perspective view of a portion of enclosure 1103 for an electronic device according to yet another embodiment of this invention. The enclosure portion 1103 includes a battery 1110 that is deposited on the interior surface of the enclosure portion 1103. The enclosure portion 1103 includes an interior portion 1101 and an exterior portion 1102. The enclosure portion 1103 corresponds to a top portion including a display that can be viewed by the consumer during use. The battery 1110 is deposited on the interior surface 1101 of the enclosure portion 1103. Also included are traces 1120 as well as electronic components 1130 and 1131. Completing the circuit is an LCD or liquid crystal display 1170. The LCD is positioned near or at an opening in the enclosure device 1103 so that the readable portion of the LCD 1170 can be viewed from the exterior surface 1102 of the enclosure portion 1103. Enclosure portion 1103 roughly corresponds to the second enclosure portion 1102 or on top of the electronic device shown in FIG. 13.

An addition to depositing a device or a battery device or energy device 1110 onto the surface of an enclosure, another embodiment of this invention is to produce a sheet including multiple cells or batteries 1110. The batteries 1110 are formed on a sheet of flexible or plastic material 1300. It should be noted that the size of the cells 1110 and the placement of the cells or individual batteries 1110 can be varied for producing various different sizes and styles of formed batteries.

FIGS. 15A through 15E disclose a method whereby the battery is formed into a conformed or conformable sheet having roughly the same shape as either the interior or exterior surface of an electronic device. The conformed sheet can then be placed or adhered directly to the interior surface or exterior surface of an electronic device. The sheet is produced with a number or plurality of cells 1110, as will be discussed later in this application. Once the sheet is formed as described later in this application, the sheet 1300 is diced into individual cells or individual battery portions 1310. In other words, a battery 1110 will be formed on a dice sheet 1310 from the main sheet 1300. The individually diced battery portion 1310 can then be formed into a variety of shapes, as shown by FIGS. 15C, 15D and 15E. These shapes can be any desired shapes. In some embodiments or in most embodiments, the shape of the sheet will conform or will be able to be placed on the interior or exterior surface of an electronic device. FIG. 15C, for example, shows a roughly square battery that has folded up sides or vacuum formed sides 1320. This particular device could be placed on the interior surface of an electronic device such as a garage door opener or any other like device.

FIG. 15D shows a more rectangular portion or diced sheet which resulted from a more rectangular battery laid down upon a sheet and diced into an individual battery portion 1310. This more rectangular formation may be glued or adhered to the inner surface of an electronic enclosure for a personal data assistant. In the alternative, the form shown in FIG. 15D may also be suitable for placement on the exterior surface of an electronic device, such as a portable data assistant.

FIG. 15E shows a more formed device that might be found on a cell phone or similar device. FIG. 15E may be formed to fit on the interior surface of a cell phone or the exterior surface of a cell phone or calculator. In other words, a diced sheet 1310 is used as a starting point for vacuum forming or for otherwise forming a battery that can be attached either to the interior or exterior surface of an electronic device. An electronic device to which it is attached can be anything including hearing aides, calculators, personal data assistants, smart cards or other credit card, watches, laser pens, power tools, surgical devices or even catheters. The list above is not exhaustive but is merely set forth as examples of the type of the devices that may include a battery shown and formed in FIGS. 15A through 15E.

In some instances, it may be advantageous to include a battery having multiple cells 1110, 1110' and 1110". In this particular instance, a dice is made 1320 that includes cells 1110, 1110' and 1110". The sheet can also be formed with fold lines 1321 and 1322, as shown in FIG. 15G.

Figure 15H:
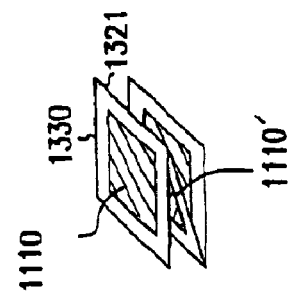
FIG. 15H is a perspective view of a fan folded plurality of diced battery cells before forming.
Figure 15G:
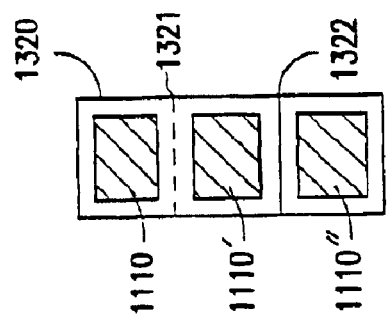
FIG. 15G is a plan view of a plurality of diced battery cells before forming.
Figure 15F:
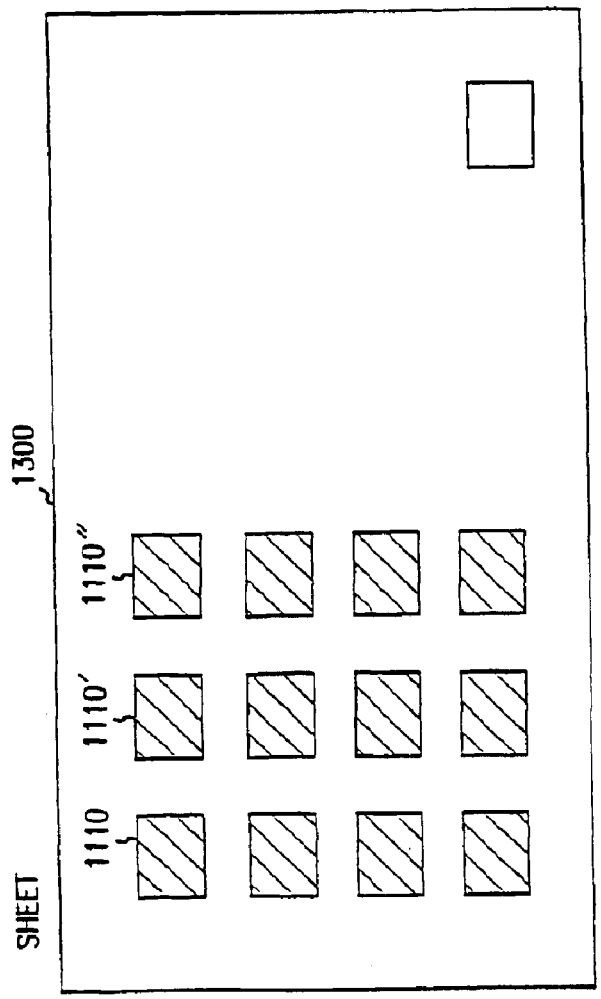
FIG. 15F is a plan view of a sheet including a plurality of battery cells.

FIG. 15H shows that the batteries have been folded along the fold lines to form a stack of three batteries 1110, 1110' and 1110". The folds shown in FIG. 15H are a fan fold. Once the fan fold is formed, as shown in FIG. 15H, the fan folded battery, including three cells 1330, can be formed in any desired shape, such as square-sided shape 1503 of FIG. 15C, angle-sided shape 1504 of 15D and curve-sided shape 1505 of 15E. The three-celled or multi-celled unit 1330 can be adhered to the interior or exterior surface of any electronic device, as discussed above. It should be noted that the fan fold can include more than three batteries or less than three batteries. The inventive aspect is that it includes a plurality of batteries. The cells 1110, 1110' and 1110" can be attached to one another so that the cells are in series after they are diced. Another possibility is that the electrical contacts for each of these could be put in contact with one another as a result of fan folding the multi-celled unit 1330.

FIGS. 15I, 15J and 15K show yet another embodiment of the invention. In this particular embodiment of the invention, the sheet of electrical cells 1300 includes a plurality of cells including 1110 and 1110'. The entire sheet 1300 is then vacuum formed to form more or less an egg carton 1350 with individual battery cells 1110 and 1110' being formed within well 1360 and 1362 in the sheet 1300. Between the wells 1360 and 1362 is a living hinge 1370. The batteries 1110 and 1110' are at the bottom of each well 1360 and 1362, as shown in FIG. 15K. The living hinge 1370 is positioned between the two wells 1360 and 1362. The first cell 1360 can be folded on top of the second well 1362 to form an electronic device enclosure 1380, as shown in FIG. 15L. It should be noted that the size of the battery portions 1110 and 1110' can be limited or placed so that other traces and room for other electronic devices can be added so that a total circuit can be formed within a disc enclosure. This provides for an advantage that wherein the electronic component could be directly placed into the wells 1160 and 1162 at sites formed at the same time as the batteries were deposited onto the sheet 1300. After placing all the various electronics, the electronic device can be formed merely by dicing two of the wells 1360 and 1362 so that they form a top and bottom of the device enclosure 1380. All sorts of electronic devices could be included, including an LCD or other display device. The LCD may be readable directly through a sheet if it is transparent or the sheet, or one of the wells 1360 and 1362, may be provided with an opening that would correspond to an opening or face of the display of an LCD or other display device. Thus, the sheet and the deposited battery thereon can ultimately become the exterior surface or the enclosure for the device formed on the sheet. This has a great advantage in that the process steps necessary to form a device are or can be quite easily and efficiently done in a continuous process. This would lead to very efficient manufacturing of electronic devices.

Figure 16A:
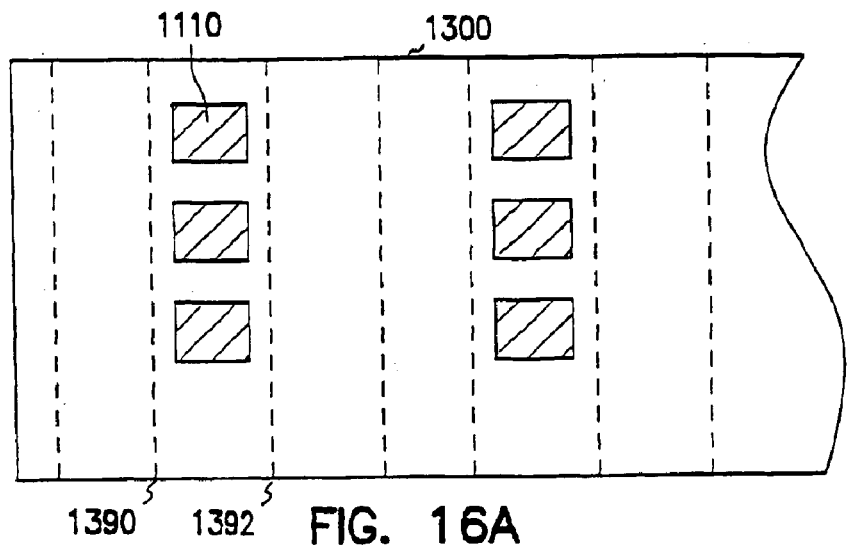
FIG. 16A is a plan view of a sheet including a plurality of battery cells.
Figure 16B:
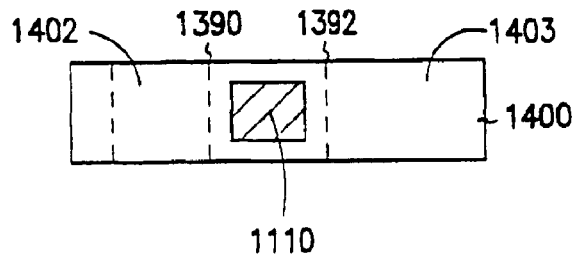
FIG. 16B is a plan view of a diced battery cell before forming.
Figure 16C:
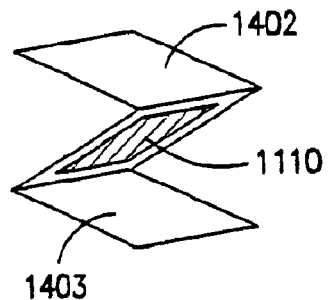
FIG. 16C is a perspective view of a fan folded diced battery cell before forming.
Figure 16D:
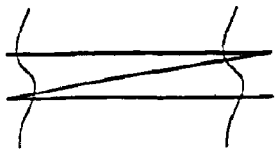
FIG. 16D shows a fan folded cord being truncated.
Figure 16E:
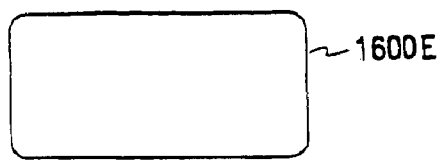
FIG. 16E shows a finished cord.

FIG. 16A is a plan view of a sheet including a plurality of cells 1110 according to this invention. FIG. 16A, 16B and 16C show a way to form a laminated battery cell and possibly laminated battery cell and electronics for a smart card or other invention that includes a battery and electronics within a card. The sheet 1300 shown in FIG. 1 6A includes cells 1110. The sheet also includes fold lines 1390 and 1392. The sheet 1300 is diced into individual sections, which include fold lines 1390 and 1392, as well as a battery cell site 1110. The battery cell site might also include electronics that are also deposited with the battery or energy source onto the sheet 1300. The diced portion 1400 includes one portion including the cell 1100 and two blank portions 1402 and 1403. The diced portion 1400 is then fan folded, as shown in FIG. 16C. Once a fan fold has been formed, the cell portion 1110 is captured between the two unpopulated sheet portions 1402 and 1403 and will provide an extra protective layer. The excess portions of the sheet 1300 can be trimmed, as shown in FIG. 16D to produce a smart card or card including both a battery 1110 and electronic, as shown as item 1600E in FIG. 16E.

Figure 17:
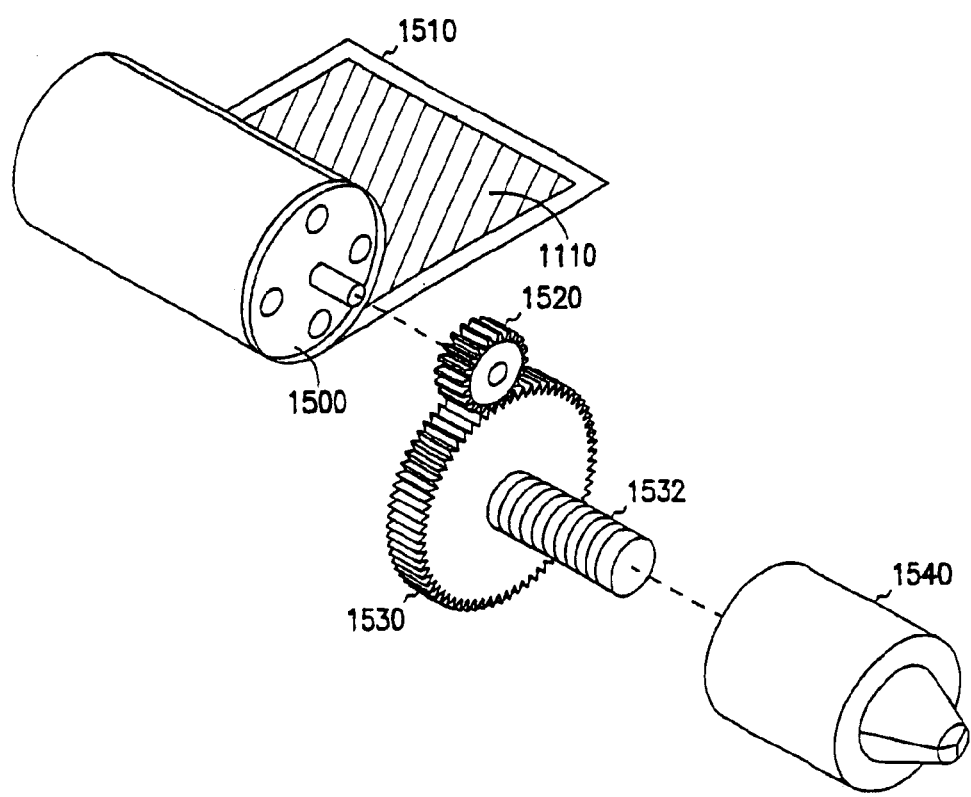
FIG. 17 is an exploded perspective view of a sheet including at least one battery cell rolled around an electrical motor in accordance with this invention.

FIG. 17 is an exploded perspective view of a diced portion of a sheet 1300 which includes one battery cell 1110 rolled around an electrical motor 1500. In this case, the diced portion, which includes a cell 1110, is an elongated strip 1510 from the original sheet 1300. The elongated strip 1510 may include several batteries placed in series or one elongated battery that is laid down as a strip on the sheet 1300. The electrical motor is electrically connected to the anode and cathode of the battery and then rolled on to the electrical motor 1500. In this case, the strip 1510, on which the battery has been deposited, becomes the case for the electrical motor or also can be viewed as being a part of the case of the electrical motor. The electrical motor can be provided with a sprocket 1520 that is used to drive another gear 1530 having a shaft 1532 attached thereto. As shown in FIG. 17, a chuck 1540 is placed upon the shaft 1532 to form a drill or other power tool. Advantageously, the power tool could be light and compact, as well as being capable of being recharged a multiplicity of times. The power tool could be a hand held drill for homeowner use or a smaller device, such as a Dremel-brand rotary hand tool.

FIGS. 18A, 18B, 18C and 18D show several other embodiments of an LED light device in which the diced portion of a sheet 1300 becomes the outside case for the penlight or light device.

Figure 18A:
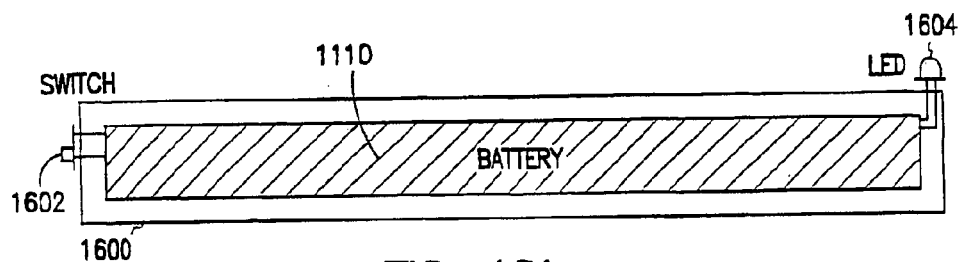
FIG. 18A is a plan view of a diced battery cell and LED before forming.

FIG. 18A is a planned view of a diced battery cell 1600 which includes a battery or energy device 1110 and a switch 1602 and an LED 1604. The switch 1602, battery 1110 and the LED 1604 form a flashlight or LED lighting device. The sheet, including the diced battery cell and LED, is rolled across its shorter distance starting at the end including the LED 1604. The LED is merely rolled into the battery and the battery is formed around the first roll to form a spiral, as shown in FIG. 18B.

Figure 18B:
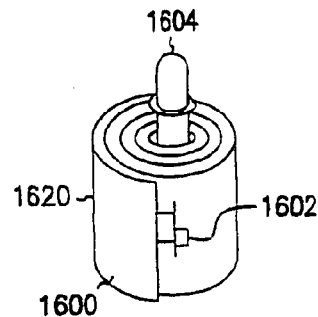
FIG. 18B is a perspective view of a diced battery cell and LED after forming.

FIG. 18B is a perspective view of the diced battery cell and LED after it has been formed into a lighting device in which the sheet 1600 in which the battery is deposited becomes an outer case. The LED can be activated by enabling the switch 1604. By enabling the switch 1604, the LED can be turned on. The sheet 1600 acts as an outer case of the lighting device formed 1620.

Figure 18C:
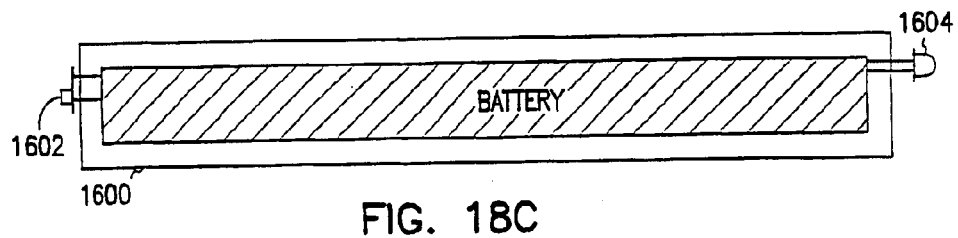
FIG. 18C is a plan view of a diced battery cell and LED before forming.
Figure 18D:
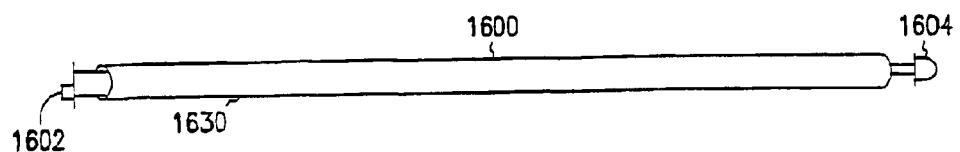
FIG. 18D is a perspective view of a diced battery cell and LED after forming.

FIGS. 18C and 18D show another embodiment of the invention for a lighting device. In this particular embodiment, again a strip 1600 is provided with a switch 1602 and an LED 1604. In this particular embodiment, the LED is positioned so that it extends beyond the length of the sheet 1600. In this particular embodiment, the sheet 1600 is rolled along its longer dimension around the LED 1604 to form an elongated case having the LED 1604 at one end of the case and a switch 1602 at the other end of the case. This forms a light emitting diode light 1630 in which the sheet 1600 is part of the case.

Figure 19A:
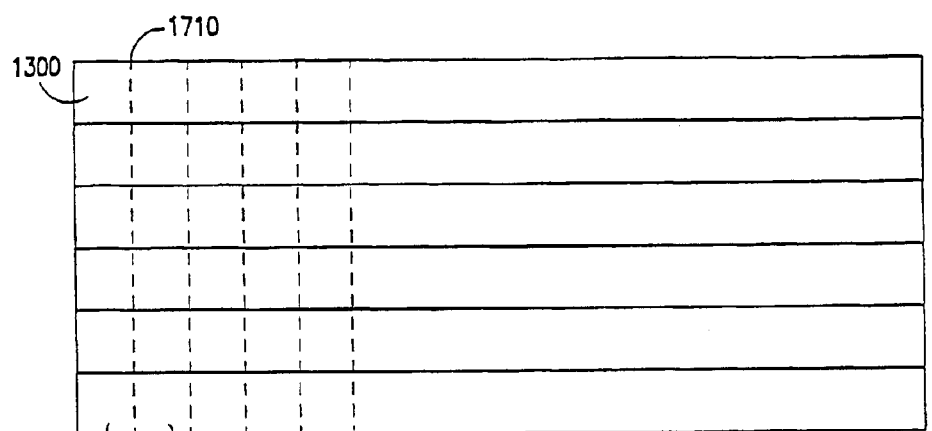
FIG. 19A is a plan view of a sheet including a plurality of battery cells according to another embodiment of this invention.
Figure 19B:
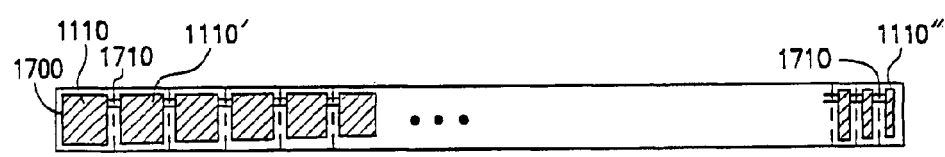
FIG. 19B is a plan view of a plurality of diced battery cells before forming.
Figure 19C:
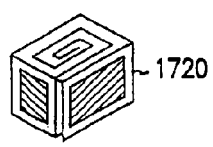
FIG. 19C is a perspective view of a formed battery including a plurality of cells.

FIGS. 19A, 19B and 19C, in some instances, is necessary to keep the battery portions 1110 and 1110' of a power source or energy source flat and not curved when it is formed.

FIG. 19A shows a sheet 1300 which includes a plurality of individual cells such as 1110 and 1110' which are an elongated strips and include fold lines, such as 1710. FIG. 19B is a plan view of a diced strip 1700 including a plurality of battery cells 1110, 1110' and 1110". It should be noted that the battery cells 1110", which are located near one end of the strip 1700, are smaller than the battery cells formed at the other end of the strip 1700. For example, battery cell 1110" has a very thin width while the battery cell 1110 is roughly more rectangularly shaped. The strip 1700 is folded successively along fold lines 1710 to form a box of cells, as shown in FIG. 19C. The smaller cells 1110" are in the inside or inner core of the box while the larger cells 1110 form the outer sides of the box. Each of the cells 1110, 1110' and 1110" and the cells in between those particular cells are placed in series with one another. The end result is a cubically formed battery cell 1720, as shown in FIG. 19C.

Figure 20:
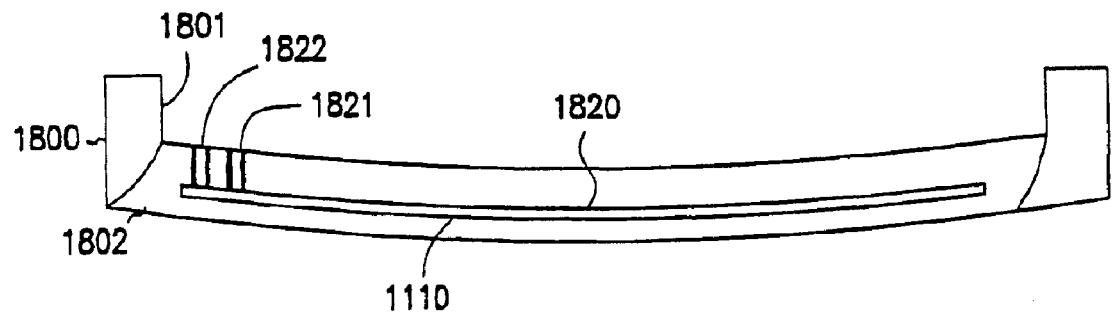
FIG. 20 is a cutaway side view of a sheet including a plurality of battery cells, which are embedded in an enclosure portion.

FIG. 20 is a cutaway side view of an enclosure portion that includes a sheet having a plurality of battery cells. It should be noted that we have discussed thus far that a sheet of battery cells, such as the one shown in FIG. 15H, can either be placed on the outside surface of an enclosure or on the inside surface of an enclosure or it can be formed or deposited upon an inside or outside surface of the enclosure. FIG. 20 shows that an enclosure portion 1800 having an interior surface 1801 and an exterior surface 1802 can be injection molded around a battery formed on a sheet. The battery could be a single battery, as is shown in FIG. 15B, or it could be a multi-celled battery, as shown in FIG. 15H. In other words, a sheet 1820 including one or more, or at least one battery cell 1110 formed by the above methods, could be held within a mold and a suitable plastic could be injection molded about or around the battery cell 1820. The mold could also include pins that electrically connect the battery 1820 to the interior surface 1801 of the enclosure portion 1800. The pins are shown by reference numerals 1821 and 1822.

Figure 21A:
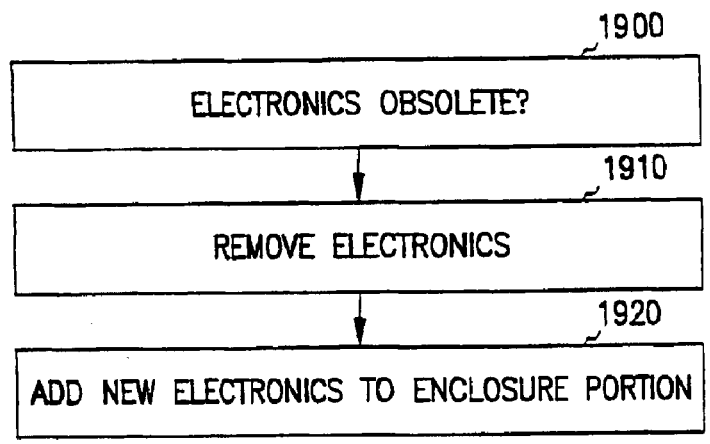
FIG. 21A is a flow chart for a first recycling method using the inventive battery and enclosure.

FIG. 21A is a flow chart that depicts a process for recycling device enclosure portions or for recycling batteries 1110 or battery cells 1110. Because the battery cell 1110 and batteries made from a number of these battery cells 1110 can be recharged many, many times, it is contemplated that any electronics associated with this circuit may become obsolete over time and, therefore, a method of recycling the batteries is also part of this invention.

The first step, depicted by reference numeral 1900, is to determine if the electronics within a circuit are obsolete. Electronics are typically obsolete due to technology advances in the electronics, which may occur over a number of years. If the electronics are obsolete, then the battery 1110 or series of cells 1110 may be removed from a device cover or enclosure portion, as depicted by reference numeral 1910. The next step is to replace the old electrical components with new electrical components, as depicted by reference numeral 1920. This first process is useful for enclosure portions where the battery or number of cells 1110 cannot be easily removed from the enclosure portion.

Figure 21B:
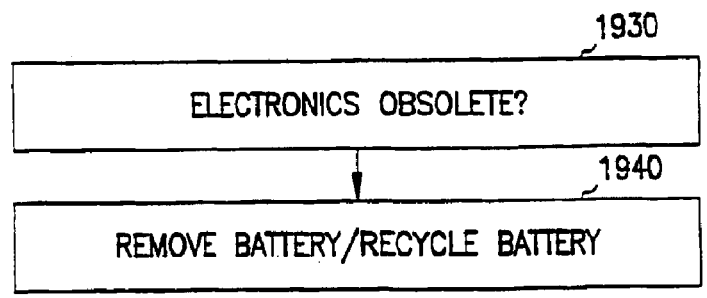
FIG. 21B is a flow chart for a first recycling method using the inventive battery and enclosure.

A second process is shown in FIG. 21B. The second process shown in FIG. 21B is useful for devices in which the battery 1110 may be removed easily from the enclosure portion. As before, the first step, depicted by reference numeral 1930, is to determine if the electronics are obsolete. If they are, the battery 1110 is merely removed from the case for the enclosure portion and recycled for use in another enclosure portion having a similar contour, as depicted by reference numeral 1950.

In some embodiments, multiple cells are stacked in the original device, the manufacture method would include connection tabs that are coupled together to form the appropriate cell capacity and voltage for some particular electronic device. Upon reaching the end of the device's life, such battery stacks could have the tabs clipped or otherwise disconnected from each other so that the battery stack could be disassembled and re-assembled in a different capacity/voltage configuration.

Design and Fabrication of Solid-state Power Sources Cofabricated with Solid-state Integrated Circuitry FIG. 22A shows a schematic circuit of an embodiment of a device 2200 having an integrated battery 2320 and circuit 2330 sharing a common terminal 2318. In other embodiments, more than one terminal is common between battery 2320 and circuit 2330, for example, when battery 2320 includes a stack having plurality of series-connected cells, and circuit 2330 connects to two or more different taps in the cell stack (e.g., if each cell of a two-cell stack provided an open-circuit potential of 3.6 volts, circuit 2330 could connect to the top of the cell stack for a portion of its circuitry needing 7.2 volts, and also to a center tap of the cell stack for a portion of its circuitry needing 3.6 volts, or a split voltage battery supply could be wired to provide a ground connection at the center tap and plus and minus 3.6 volts at the top and bottom of the stack). Common terminal 2318 connects battery 2320 to circuit 2330, and optionally can be brought out as a connection to other components. In some embodiments, common terminal connects the cathode of battery 2320 to circuit 2330; in other embodiments, terminal 2318 connects the anode of battery 2320 to circuit 2320 as shown in FIG. 22A. In some embodiments, circuit 2330 includes one or more conductors 2317 that are used to connect to other components and/or to the other connections to battery 2320. In some embodiments, battery 2320 includes one or more conductors 2319 that are used to connect to other components and/or to the other connections to circuit 2330. In other embodiments, terminal 2317 of circuit 2330 is connected directly to terminal 2319 of battery 2320 to form a complete device, and no connection is made to other external devices using terminals 2317, 2318, or 2319. Note that circuit 2330 can include any type of circuitry, for example, as shown in FIGS. 23–26, wiring traces 2332–2337, one or more active or passive devices such as integrated circuit 2340, switches, light sources, LCD displays, photovoltaic cells, etc.

Figure 22H:
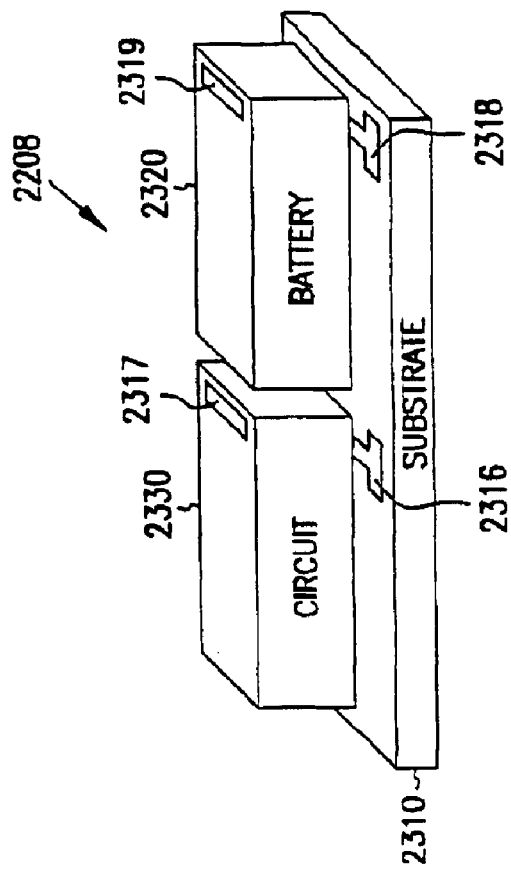
FIG. 22H shows a block diagram perspective view of an integrated device implementing the circuit of FIG. 22D having the battery and the circuit built side-by-side on a substrate.
Figure 23:
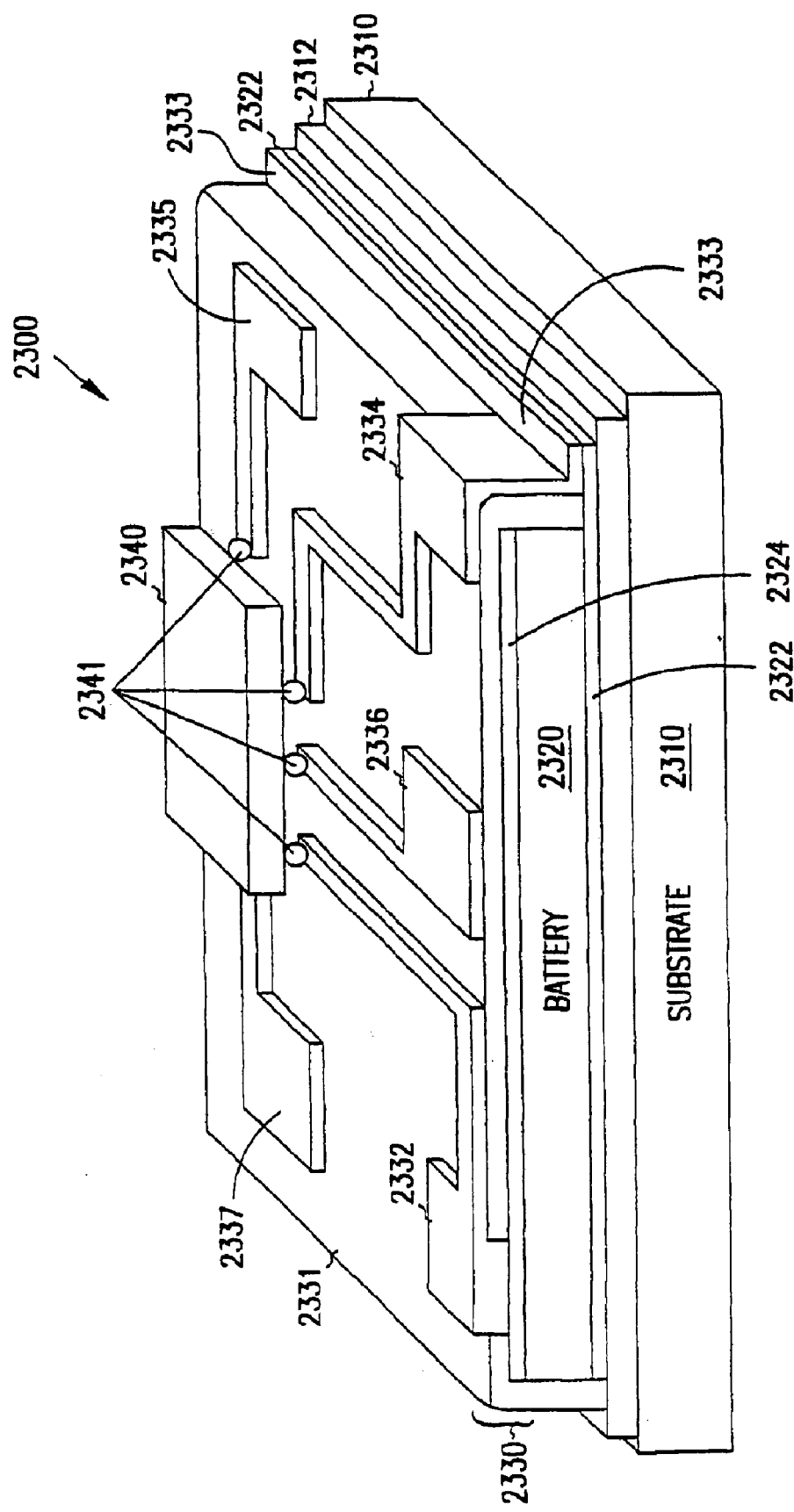
FIG. 23 shows a perspective view of an embodiment 2300 of the present invention having a battery overlaid with circuitry.
Figure 24A:
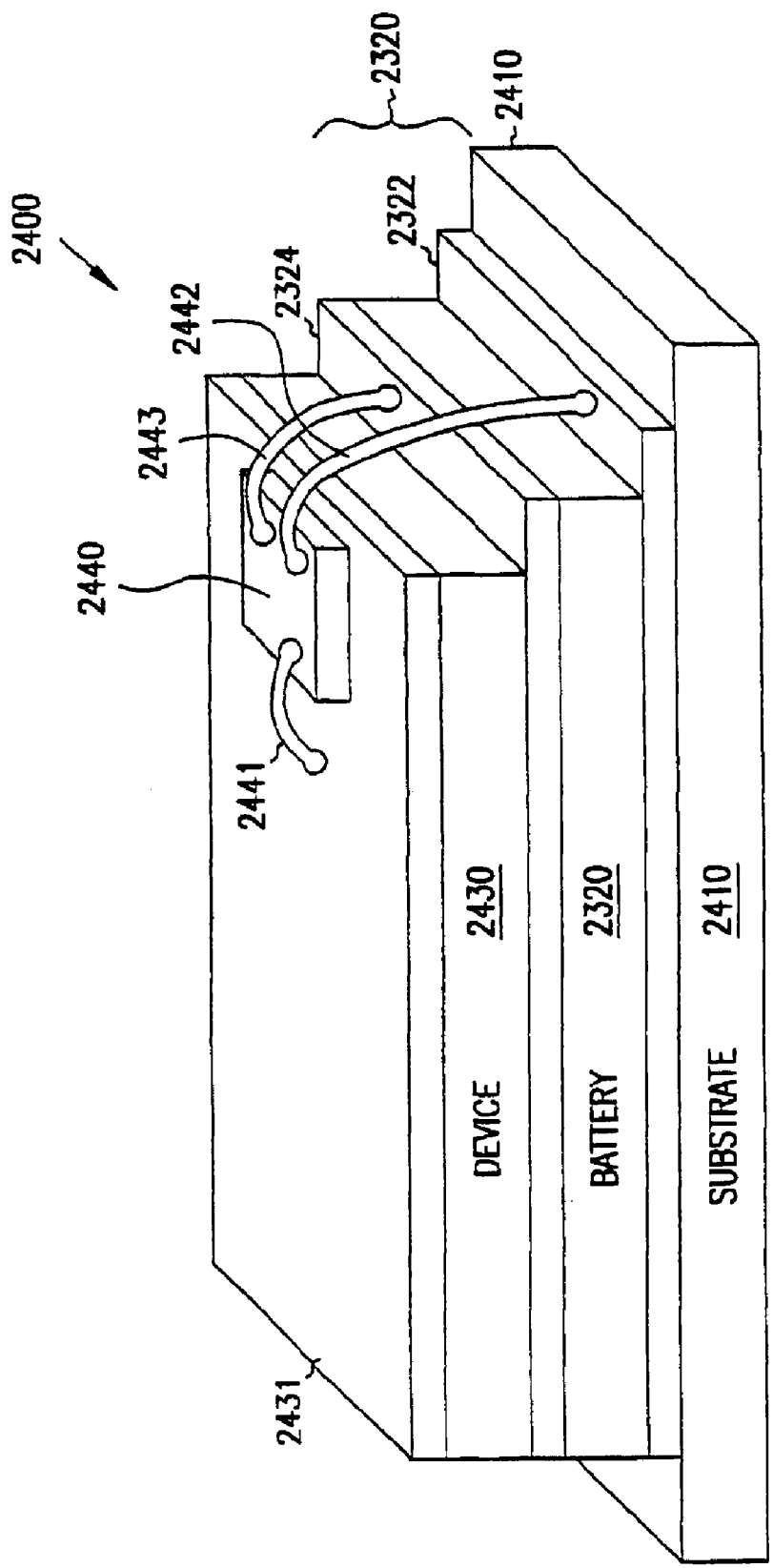
FIG. 24A shows a perspective view of an embodiment 2400 of the present invention having a battery overlaid with an integrated device.

FIG. 22B shows a block diagram perspective view of an integrated device 2201 implementing circuit 2200 of FIG. 22A having the circuit 2330 built on the battery 2320. According to the present invention, in some embodiments such as shown in FIG. 22B, battery 2320 is deposited or fabricated first (for example, onto a polymer substrate), and later circuit 2330 is deposited or fabricated to a surface of battery 2320. In some embodiments as shown in FIG. 22B, a top surface of the device implementing circuit 2330 includes one or more conductors 2317 that are used to connect to other components and/or to the other connections to battery 2320. In some embodiments, a bottom surface of battery 2320 includes one or more conductors 2319 that are used to connect to other components and/or to the other connections to circuit 2330. In some embodiments, a top surface of battery 2320 (the surface fabricated adjacently to circuit 2330) is partially exposed and includes one or more conductors 2318 that are used to connect to other components and/or to the other connections to circuit 2330. FIG. 23 and FIG. 24A show some examples of devices 2300 and 2400 that are exemplary embodiments of device 2201 of FIG. 22B.

FIG. 22C shows a block diagram perspective view of an integrated device 2202 implementing circuit 2200 of FIG. 22A having the battery 2320. built on the circuit 2330. According to the present invention, in some embodiments such as shown in FIG. 22C, circuit 2330 is deposited or fabricated first (for example, an integrated circuit chip built onto a silicon substrate), and later battery 2320 is deposited or fabricated to a surface of battery 2320. In some embodiments as shown in FIG. 22B, a top surface of the device implementing circuit 2330 is left partially exposed and includes one or more conductors 2317 that are used to connect to other components and/or to the other connections to battery 2320. In some embodiments, a top surface of battery 2320 includes one or more conductors 2319 that are used to connect to other components and/or to the other connections to circuit 2330. In some embodiments, a top surface of circuit 2330 (the surface fabricated adjacently to circuit 2330) is partially exposed and includes one or more conductors 2318 that are used to connect to other components and/or to the other connections to circuit 2330. FIG.

Figure 26A:
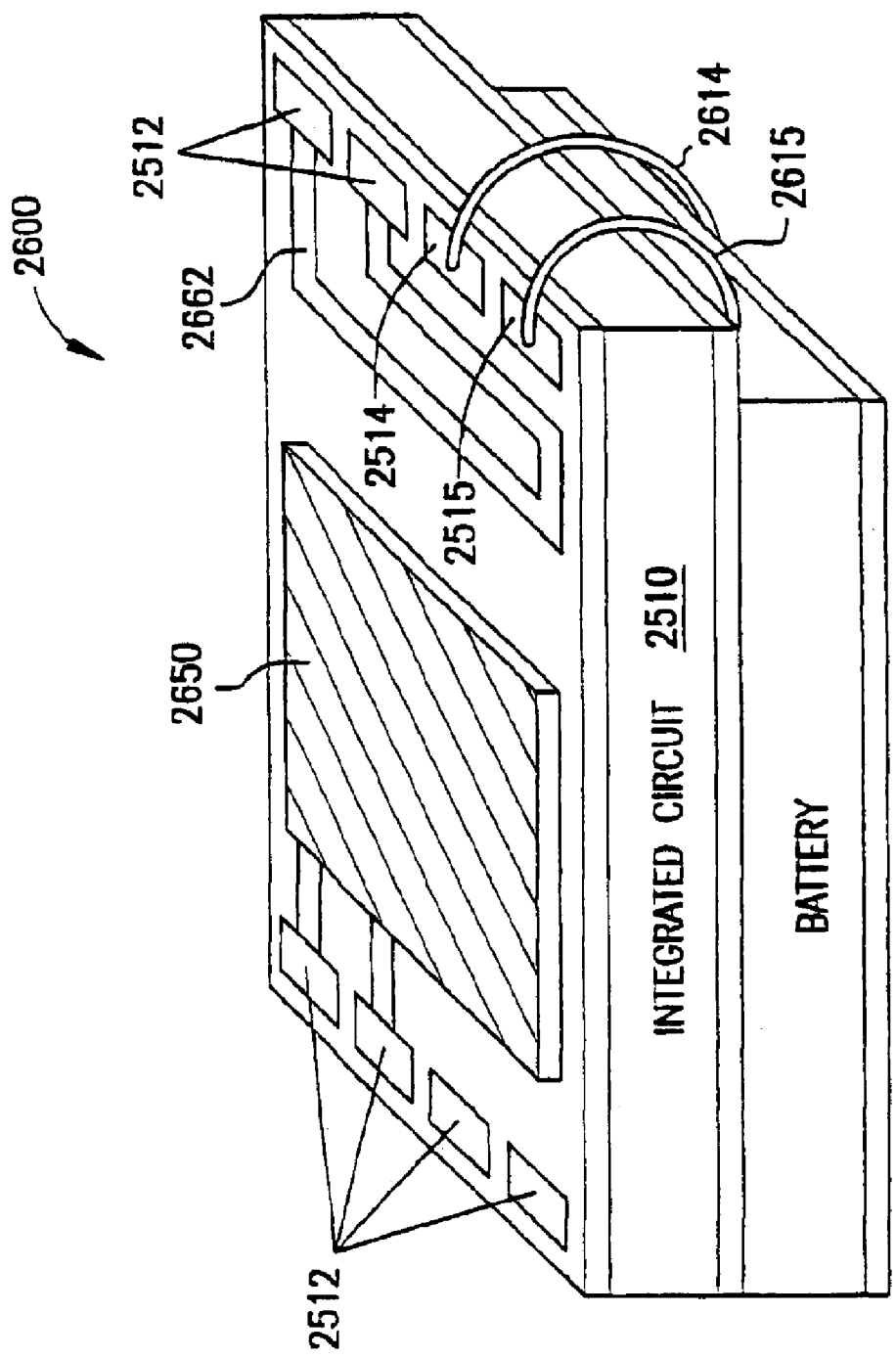
FIG. 26A shows a perspective view of an embodiment 2600 of the present invention having an integrated circuit overlaid on its back with a battery.

25A and FIG. 26A show some examples of devices 2500 and 2600 that are exemplary embodiments of device 2202 of FIG. 22C.

FIG. 22D shows a schematic circuit 2205 of an embodiment of an integrated battery 2320 and circuit 2330 each having separate, electrically isolated terminals. Such embodiments are substantially identical to the embodiments of FIGS. 22A, 22B, and 22C, except that an insulator between terminal 2318 of the battery 2320 and terminal 2316 of the circuit 2330 keeps these electrically separate.

FIG. 22E shows a block diagram perspective view of an integrated device 2206 implementing circuit 2205 of FIG. 22D having the circuit built on the battery. Such embodiments are substantially identical to the embodiments of FIG. 22B except that an insulator 2331 is deposited on battery 2320 before the rest of circuit 2330 is deposited or fabricated. In some embodiments, a portion of the top surface of battery 2320 is left partially exposed and includes one or more conductors 2318 that are used to connect to other components and/or to the other connections to circuit 2330. In some embodiments, a portion of the top surface of insulator layer 2331 is coated with a conductor and is left partially exposed and includes one or more conductors 2316 from circuit 2330 that are used to connect to other components and/or to the other connections to battery 2320.

FIG. 22F shows a block diagram perspective view of an integrated device 2207 implementing circuit 2205 of FIG. 22D having the battery 2320 built on but insulated from the circuit 2330. Such embodiments are substantially identical to the embodiments of FIG. 22C except that an insulator 2331 is deposited on circuit 2330 before the rest of battery 2320 is deposited or fabricated. In some embodiments, a portion of the top surface of circuit 2330 is left partially exposed and includes two or more conductors 2316 and 2317 that are used to connect to other components and/or to the other connections to battery 2320. In some embodiments, a portion of the top surface of insulator layer 2331 is coated with a conductor and is left partially exposed and includes one or more conductors 2318 from battery 2320 that are used to connect to other components and/or to the other connections to circuit 2330.

Figure 22G:
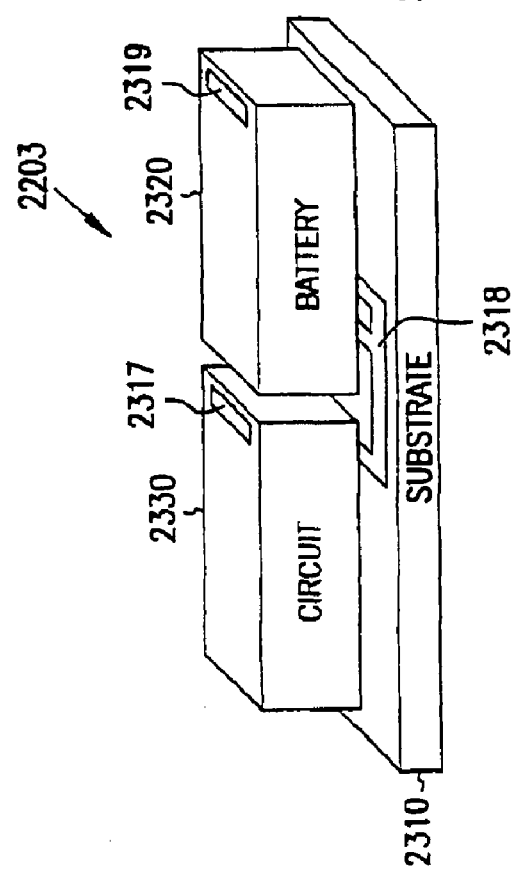
FIG. 22G shows a block diagram perspective view of an integrated device implementing the circuit of FIG. 22A having the battery and the circuit built side-by-side on a substrate.

FIG. 22G shows a block diagram perspective view of an integrated device 2203 implementing circuit 2200 of FIG. 22A having the battery 2320 and the circuit 2330 built side-by-side on a substrate 2310. In some embodiments, a pattern of conductive areas or traces is deposited on substrate 2310, and the successive layer(s) of battery 2320 and circuit 2330 are then deposited. In some embodiments, circuit 2330 consists only of these conductive traces. In other embodiments, one or more of the process steps or deposited layers of battery 2320 and circuit 2330 are common, and thus performed at substantially the same time for both circuit 2330 and battery 2320, thus increasing the reliability, speed and yield of fabrication and lowering the cost of fabrication. In the embodiment shown, trace 2318 is deposited on substrate 2310 and forms a common bottom electrical connection for both circuit 2330 and battery 2320. Other aspects of FIG. 22G can be understood by reference to FIGS. 22A–22C.

FIG. 22H shows a block diagram perspective view of an integrated device 2208 implementing circuit 2205 of FIG. 22D having the battery 2320 and the circuit 2330 built side-by-side on a substrate 2310. This embodiment is substantially identical to that of FIG. 22G, except that separate traces are provided for signals 2316 and 2318.

FIG. 23 shows a perspective view of an embodiment 2300 of the present invention having a battery 2320 overlaid with circuitry. In some embodiments, substrate 2310 is a conductor such as a thin sheet of metal, and is overlaid with an insulator layer 2312, and then the bottom conductor layer 2322 of battery 2320. In other embodiments, insulator layer 2312 and bottom conductor layer 2322 are omitted, and a conductive substrate 2310 itself forms the bottom conductive layer for battery 2320. In some embodiments, battery 2320 is a thin-film battery deposited by a process, and having a structure, as described in FIGS. 1B to 8 herein. In the embodiment shown, battery 2320 includes a bottom conductive layer/electrical contact 2322 and a top conductive layer/electrical contact 2324, and is covered by a protective/electrically insulating layer 2331 having one or more openings or vias for electrical connections, for example, a via through which pad/trace 2332 connects to battery 2320. In some embodiments, the top conductor 2324 of battery 2320 is the anode connection. In the embodiment shown, the connection to the lower conductive layer/electrical contact 2322 from pad/trace 2334 is a conductive trace deposited over the side of battery 2320 to extended contact area 2333. In some embodiments, additional connection pads/traces 2335, 2336, and 2337 are deposited, for example, using a shadow mask that defines where the traces will go, and a metal-evaporation source, PVD source, CVD source, sputter source or other source to supply the conductor being laid down. In other embodiments, a conductive layer for circuit 2330 is deposited over an entire upper surface, and the unneeded portions are removed, for example, using photolithography and etching techniques. In some embodiments, multiple layers are successively deposited, wherein these layers include conductors, insulators, semiconductors (e.g., polysilicon or polymer semiconductors), electrolytes, passivation layers, mechanical-protection layers, sealants, reactants (such as sensor materials that react with, e.g., smoke, carbon dioxide, antibodies, DNA, etc.) and/or decorative pattern, topography, design or color layers.

Some embodiments further include a separately fabricated circuit 2340 that is bonded (e.g., by adhesive or solder) to the rest of the deposited circuitry 2330, for example, a flip-chip integrated circuit 2340 having bump, ball or ball-grid array connections 2341 as shown in FIG. 23. In other embodiments, packaged chips are used, e.g., J-leaded, gull-wing leaded, in-line-pin, or other plastic- or ceramic-encapsulated chip packages.

FIG. 24A shows a perspective view of an embodiment 2400 of the present invention having a battery 2320 overlaid with an integrated device 2430. In some embodiments, integrated device 2430 is a so-called supercapacitor relying on either charge accumulation on opposing sides on an insulator (as in a capacitor) or ion transport across an electrolyte (as in a battery), or both charge accumulation and ion transport to store electrical energy. In some embodiments, integrated device 2430 includes a photovoltaic cell of conventional construction deposited directly on battery 2320.

Some embodiments further include a separately fabricated circuit device such as an integrated circuit chip 2440 that is wire-lead bonded to device 2430 using wire 2441, to device-battery common terminal 2324 using wire 2443, and to bottom battery contact 2322 using wire 2442. For example, in one embodiment having a supercapacitor device 2430, integrated circuit 2440 includes a wireless communication circuit that uses the battery for overall power needs and uses supercapacitor device 2430 for quick-burst power needs such as for transmitting short burst of data to an antenna. Other embodiments include other fabricated circuit devices such as switches, LEDs or other light sources, LCD displays, antennas, sensors, capacitors, resistors, etc., wired to device 2400.

In one embodiment, battery 2320 includes a bottom conductor layer of platinum (e.g., 0.5 micrometers thick), a cathode of lithium cobalt oxide covered by a LiPON electrolyte and a carbon anode, and a top electrode of platinum. On top of these depositions, device 2430 includes a layer of ruthenium oxide, an electrolyte of LiPON, another layer of ruthenium oxide and a top layer of platinum. Such a device 2430 would store energy by transporting lithium ions derived from the LiPON electrolyte from one to another of the top and bottom surface of the electrolyte, as well as perhaps moving charge (electrons) to an opposing surface. Such a device exhibits a higher-current discharge rate than a comparable battery, and a higher energy storage than a comparable capacitor. The present invention including ion-assist deposition provides for higher quality cathode films (better crystal orientation) and better electrolyte films (more complete isolation and fewer pinhole defects for any given thickness, thus allowing thinner electrolyte films that increase ion transport rates), and better capacitor dielectric films (more complete isolation and fewer pinhole defects for any given thickness, thus allowing thinner dielectric films that increase dielectric isolation, capacitance, and charge storage). In some embodiments, a capacitor insulator layer is made of a barium strontium titanate.

In some embodiments, a cathode layer of lithium-cobalt-oxide is covered by a LiPON electrolyte layer and a lithium (0.5)-cobalt-oxide anode layer. This anode layer is non-stoichiometric deposited using a source that has excess cobalt and oxygen relative to lithium as compared to that used for the cathode, and various embodiments use different lithium ratios.

Design and Fabrication of Solid-state Power Sources Fabricated as a Laminate on a Rigid or Flexible Direct Energy Conversion Material such as Photovoltaic Virtually all electronics require energy to operate and perform the designed functions. This energy typically comes from either an AC source such as a home wall electrical outlet or a battery mounted in the packaging of the electronic device. More recently, advances in the conversion of heat and light into energy have fueled research in the area of direct energy conversion (e.g., by photovoltaic cells). This has the potential to supply a large percentage of the world energy needs in a clean and safe manner. One problem with these methods of energy supply has been the cyclical nature of the energy being converted. Whether heat or light, the source usually goes away for a 6- to 12-hour period resulting in zero output from the unit. One way around this problem is to supply a battery with the unit to supply power during periods of low light or heat input. This is however not an ideal solution as today's rechargeable batteries are bulky and failure prone after several charge/discharge cycles. The present invention solves this problem by integrating its solid-state Lithium battery directly on the energy conversion substrate. The present battery has a distinct advantage over current technologies, in that it is not prone to failure or memory problems over tens of thousands of charge/discharge cycles, has very high capacity, is lightweight, can be fabricated on nearly any substrate and is cheap to manufacture. The resultant product is a reliable, portable power source with steady output over extended periods or rain or shine, night or day, warm or cold.

According to the present invention, solid-state processes are used to cofabricate direct energy conversion materials and energy storage on the same substrate. This is possible by using the low-temperature processes for solid-state batteries described above.

Figure 24B:
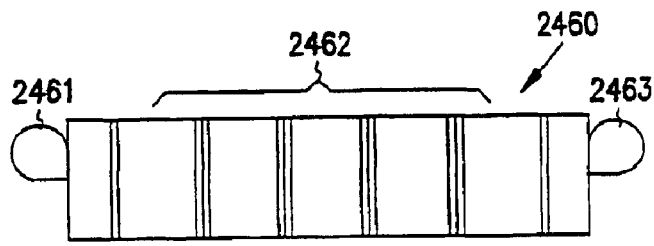
FIG. 24B shows a block diagram of a layer-deposition system 2460.

FIG. 24B shows a block diagram of a battery-layer-deposition system 2460. In some embodiments, system 2460 includes a supply reel 2461, a deposition chamber 2462 that deposits one or more layers of battery 2320 onto a substrate 2410 as described above, and a takeup reel 2463. Typically, deposition chamber 2462 is a vacuum chamber that encloses supply reel 2461 and takeup reel 2463, and successively deposits a plurality of layers, wherein each of one or more of the layers is immediately treated (e.g., by ion assist, laser surface anneal, heat surface anneal, or kinetic treatment), according to the present invention, to impart a high-quality surface structure to that layer or those layers before subsequent layers are deposited, and without substantial heating of the underlying layer(s) or substrate. For layers that need to be thicker, a longer deposition station is provided than the station for thinner layers. In some embodiments, the lower contact layer 2322 is deposited onto a starting substrate film, fabric, or foil 2410, then the cathode, electrolyte, anode, and anode-contact layers are deposited, wherein the cathode layer and/or the electrolyte layer are treated (e.g., by an ion-assist beam) before subsequent layers are deposited.

Figure 24C:
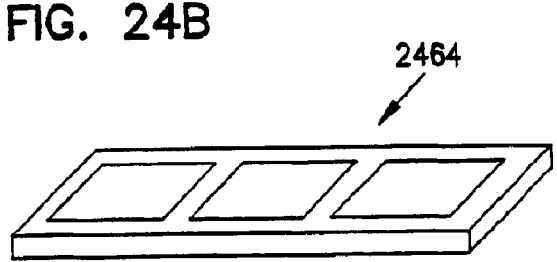
FIG. 24C shows a perspective view of a partially processed sheet 2464.

FIG. 24C shows the resulting item 2464, which is a continuous sheet of substrate material 2410 having batteries 2320 deposited on it. This partially built item 2464 is then used as the supply reel 2466 of layer-deposition system 2465 of FIG. 24D.

Figure 24D:
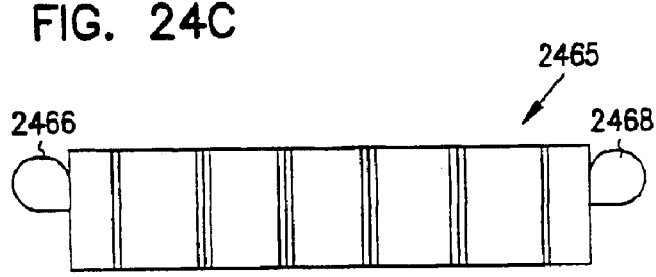
FIG. 24D shows a block diagram of a layer-deposition system 2465.

FIG. 24D shows a block diagram of a energy-conversion-layer-deposition system 2465. In some embodiments, system 2565 deposits layers that form a photovoltaic cell 2430 onto battery 2320 of FIG. 24A. In some embodiments, system 2460 and system 2465 are merged into a single system having a single supply reel 2461 and a single takeup reel 2468, and having layers of the battery 2320 and of the photovoltaic cell 2430 successively deposited. In other embodiments, other types of devices 2430 are deposited such as capacitors, antennae, circuitry, transducers, sensors, magneto-resistors (e.g., of the giant magneto-resistor type), etc.

Figure 24E:
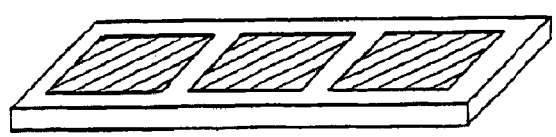
FIG. 24E shows a perspective view of a processed sheet 2469.
Figure 24F:
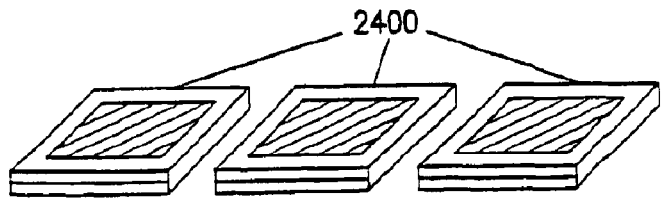
FIG. 24F shows a perspective view of a diced final device 2400.

FIG. 24E shows a perspective view of a processed sheet 2469 that is the result of processing be system 2460 and system 2465. Sheet 2469 is then cut or diced into individual devices 2400. FIG. 24F shows a perspective view of three diced final devices 2400. In other embodiments, sheet 2469 is cut into any desired number of devices 2400.

In other embodiments, system 2460 and system 2465 deposit a battery 2320 and a photovoltaic cell 2330 side-by-side on one face of substrate 2310, such as shown in FIG. 22G and FIG. 22H. In some such embodiments, one or more of the layers deposited for battery 2320 are also deposited for photovoltaic cell 2330 simultaneously of the same deposition material, thus saving process steps but making a wider device than if stacked as in FIG. 24A.

Figure 25A:
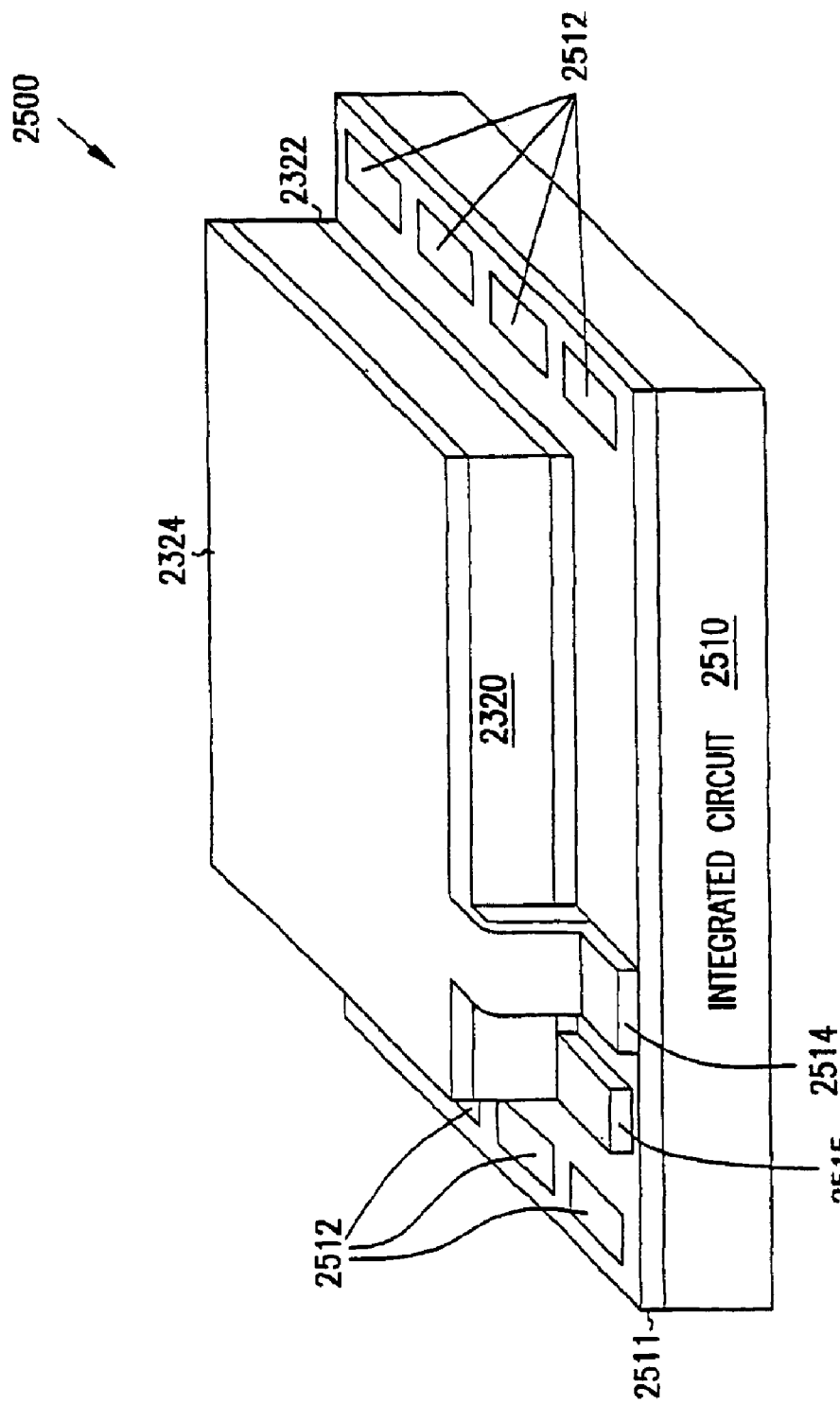
FIG. 25A shows a perspective view of an embodiment 2500 of the present invention having an integrated circuit overlaid with a battery.

FIG. 25A shows a perspective view of an embodiment 2500 of the present invention having an integrated circuit 2510 overlaid with a battery 2320. In some embodiments, integrated circuit 2510 includes a top insulator layer 2511 having a plurality of vias or openings 2512 to the active surface of the integrated circuit 2510 (the side with devices and connectors). Two of these vias are used as contacts 2514 and 2515 between integrated circuit 2510 and battery 2320. Battery 2320 is deposited as described for FIG. 23. In some embodiments, battery 2320 is deposited on an integrated circuit wafer before integrated circuit 2510 is diced apart from the other integrated circuits. In some embodiments, battery 2320 is deposited onto integrated circuit 2510 after integrated circuit 2510 is diced apart from the other integrated circuits. Some embodiments further include a passivation layer over the top and sides of battery 2320 such as layer 2331 of FIG. 23.

In other embodiments, a circuit such as circuit 2330 of FIG. 23 is used in place of integrated circuit 2510 of FIG. 25A. Thus, a pattern of vias and/or other devices or circuitry is deposited on a substrate, and battery 2320 is deposited on the top of the predefined circuitry/substrate, as in FIG. 25A. In some embodiments, a photovoltaic cell is used as such a circuit device/substrate, and battery 2320 is deposited directly on the premanufactured photovoltaic cell. In some embodiments, an integrated circuit such as 2440 of FIG. 24A is wired to the battery 2320 and the premanufactured photovoltaic cell to control charging of the battery from the cell and/or to control using power for other devices (such as a light source or hearing aid) from the photocell during periods of high amounts of light and power available from the photovoltaic cell, and using power from the battery during periods of little or no light and power available from the photovoltaic cell.

Virtually all electronics require energy to operate and perform the designed functions. This energy typically comes from either an AC source such as a home wall electrical outlet or a battery mounted in the packaging of the electronic device. Until the last few years, this approach has proved to be acceptable even though the inefficiencies caused waste of both energy and natural resources in that the device housing had to be made large enough to incorporate the energy package or conversion electronics. As electronic complexity increases, the wasted real estate and energy begin to become an issue as the demands of operator interface begin to compete with the energy source for area on the device. The application of the solid-state battery process of the present invention allows the cofabricating of electronics and the associated power source together on chip.

Solid-state processes are used to cofabricate electronics and solid-state rechargeable battery on a common substrate such as silicon used for IC processing. This is possible by using the low-temperature processes for solid-state batteries described above.

Referring to FIG. 25A, in some embodiments, the integrated circuit (IC) 2510 in wafer form is processed normally through final passivation including bond-pad etch. All thermal processing necessary for the electronics is performed conventionally. The IC in wafer form is sent to backend energy processing. In some embodiments, the design of the IC includes electronics for control of recharge for the solid-state energy source; contact vias for connecting the cathode plate and anode plate to the circuit. Using shadow masks with sufficient overlay accuracy, the necessary components of the energy structure 2320 are deposited using PVD or CVD as described above. A final passivation coating (such as 2331 of FIG. 23) is applied to the energy stack. The IC in wafer form with energy source integrated is sent for test, dicing and packaging. This provides integration of electronics and solid-state rechargeable batteries by cofabrication.

Design and Fabrication of Solid-state Power Sources Fabricated as a Laminate on the Packaging for the Device the Energy Source will Power Solid-state processes are used to cofabricate electronics and packaging. This is possible by using the low-temperature processes for solid-state batteries described above.

Figure 25D:
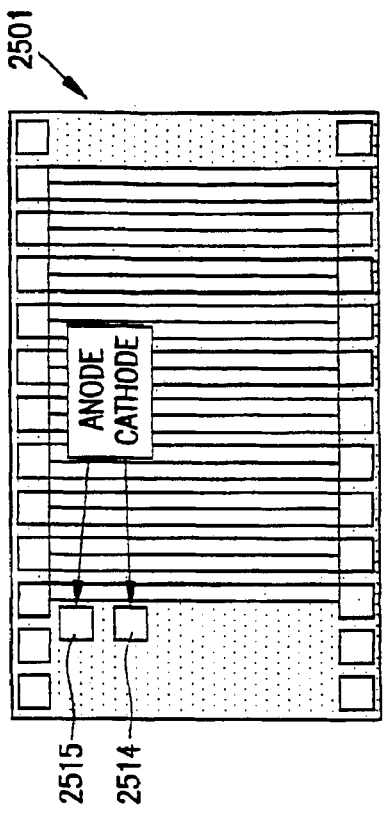
FIG. 25D shows a plan view integrated battery-IC 2501.
Figure 25E:
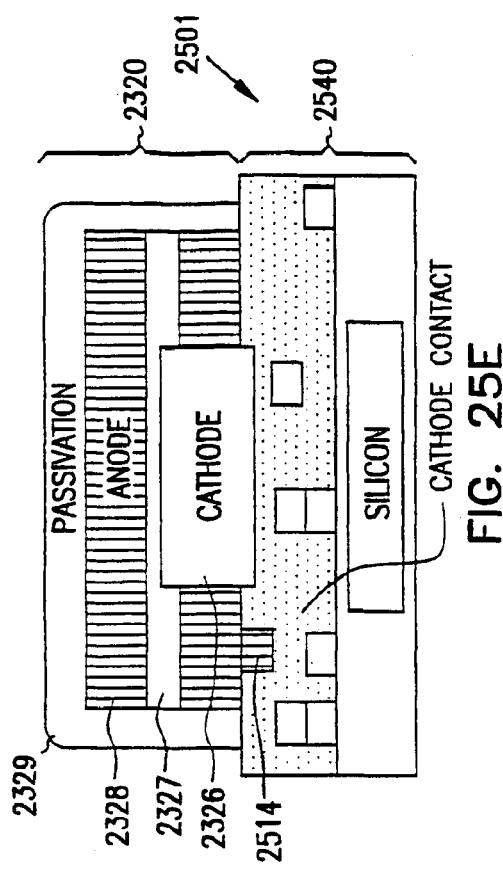
FIG. 25E shows an elevational view of integrated battery-IC 2501.
Figure 25B:
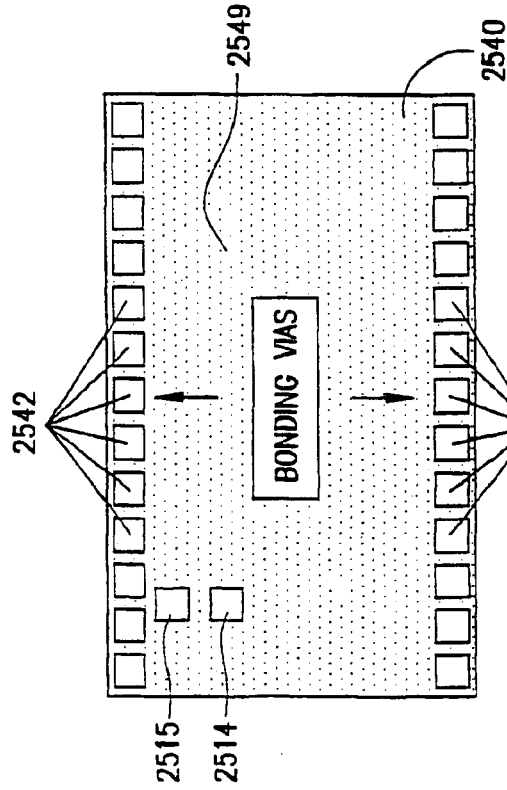
FIG. 25B shows a plan view of IC 2540.
Figure 25C:
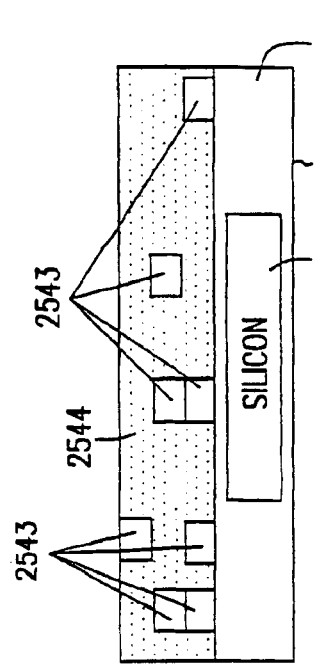
FIG. 25C shows an elevational view of IC 2540.

FIGS. 25B–25E show a fabrication sequence for cofabrication of solid-state integrated circuits and solid-state energy source such as that described above, but onto a packaged IC 2540. FIG. 25B shows a plan view and FIG. 25C shows an elevational view of IC 2540. In some embodiments, IC 2540 includes a silicon chip 2545 having integrated components such as transistors, resistors, memory, etc., a lower substrate 2546, and a wiring superstrate 2544 having deposited wires 2543 that extend to bonding vias 2542. FIG. 25D shows a plan view and FIG. 25E shows an elevational view of an integrated battery-IC 2501. Battery-IC 2501 includes a cathode 2326 (e.g., lithium cobalt oxide), electrolyte layer 2327 (e.g., LiPON), and anode layer 2328 (e.g., including copper, carbon, lithium, lithium-magnesium, and/or other suitable anode material). Passivation overcoat layer 2329 suitable to protect the inner components of battery 2320 is then deposited or grown.

In one embodiment, the packaged IC 2540 product is formed by conventional means. All machine work and cleaning is accomplished. The package 2540 is sent to energy processing for deposition of battery 2320 or other energy-storage device. The design of the package included a suitable area 2549 for deposition of battery components. Using shadow masks with sufficient overlay accuracy, the necessary components of the energy structure (e.g., a battery and/or photovoltaic cell) are deposited using the methods described above. A final passivation coating 2329 is applied to the energy stack structure. The package with energy structure integrated is sent for assembly.

In one embodiment, further electronics are attached to the package/energy entity 2501 by way of adhesive. The electronics are then hardwired to the package/energy entity. In a second embodiment, the electronics are mounted directly to the package/energy entity by 2501 way of solder bumps. In some embodiments, the entire assembly is optionally potted, then sealed by the package cover. In other embodiments, the battery is formed on a substrate suitable as a packaging material. The substrate is formed into individual package form factors. The package with energy structure integrated is sent for assembly.

Thus, the present invention provides integrated product packaging and solid-state rechargeable batteries by cofabrication where the battery is deposited on the already-formed package. The present invention also provides integrated product packaging and solid-state rechargeable batteries by cofabrication where the battery is deposited on a suitable package material, then formed into the package.

The present invention also provides a method of attaching electronics to a package/energy hybrid wherein the electronics are mounted with adhesive, then hardwired to the energy source. The present invention further provides a method of attaching electronics to a package/energy hybrid wherein the electronics are attached to the energy source via solder bumps.

FIG. 25F shows a block diagram of a layer-deposition system 2560 much the same as that of FIG. 24B, however rather than using a sheet of polymer or other homogenous substrate material 2410, system 2560 starts with a sheet 2561 having a plurality of processed packaged ICs 2540 that are received by takeup reel 2563.

FIG. 25G shows a perspective view of a processed sheet 2569. Sheet 2569 includes a plurality of preprocessed circuits 2540 each having a battery 2320 deposited on it by system 2560. Sheet 2569 is then cut or diced into individual devices 2501.

FIG. 26A shows a perspective view of an device 2600 of the present invention having an integrated circuit 2510 overlaid on its back with a battery 2320. This embodiment is similar to that of FIG. 25A, except that the battery 2320 is deposited on the back of IC 2510, and is wire-lead bonded to contact 2514 using wire 2614 from battery contact 2519 and to contact 2515 using wire 2615 from batter contact 2518.

In some embodiments, device 2600 further includes device 2650 such as a photovoltaic cell fabricated on a surface of integrated circuit 2510, for example, on the opposite side as that facing battery 2320. In some embodiments, such a photovoltaic cell 2650 provides power to IC 2510 for both operation of IC 2510 and for charging of battery 2320 during periods of relatively bright light, and then battery 2320 provides power to IC 2510 for operation during periods of relatively dim or no light. In some embodiments, device 2600 includes one or more devices 2650 such as sound transducers for such applications as a hearing aid having an combined transducer-battery-amplifier device. In some such embodiments, both a photovoltaic cell 2650 and one or more sound transducers 2650 are deposited in order to provide a light-rechargeable hearing aid which could be taken out of the ear at night and placed in a light-emitting recharging stand (e.g., that of FIG. 27L), avoiding the need to replace batteries or even to electrically connect to an external recharging circuit. In some embodiments, a photovoltaic cell and/or a sound transducer is/are deposited on one face of device 2600 for recharging and for sound pickup, and a sound transducer is deposited on an opposing face for use as s speaker for applications such as a hearing aid.

In yet other embodiments, 2600 further includes device 2650 such as a magnetoresistive sensor fabricated on a surface of integrated circuit 2510, for example, on the opposite side as that facing battery 2320. Such a device 2600 could be used in a compass, for example.

In some embodiments, embodiment 2600 further includes an antenna or electromagnetic radiation receiving loop 2662 fabricated on a surface of integrated circuit 2510, for example, on the opposite side as that facing battery 2320. In some such embodiments, device 2600 also includes one or more devices 2650 such as sound transducers for such applications as a hearing aid having an combined transducer-battery-amplifier device in order to provide a radio frequency-wave-rechargeable hearing aid which could be taken out of the ear at night and placed in an RF-emitting recharging stand (e.g., that of FIG. 27M), avoiding the need to replace batteries or even to electrically connect to an external recharging circuit.

In various embodiments, such an antenna or electromagnetic radiation receiving loop 2662 is fabricated on device 2202, 2203, 2204, 2206, 2207, 2208, 2300, 2400, or 2500 (or 2700 described below) or other battery devices described herein. In some such embodiments, electromagnetic radiation received wirelessly by antenna 2662 can be such low-frequency radiation as 50- or 60-hertz magnetic radiation from a coil connected to house current (e.g., that of FIG. 27L). In other such embodiments. RF radiation such as radio, TV, cellular, etc. having frequencies up to and exceeding 2.4 GHz is received. In some embodiments, multiple antennae are used, e.g., one for transducing communications signals and another for receiving recharging signals.

FIG. 26B shows a block diagram of a layer-deposition system 2660. System 2660 is much the same as system 2560 of FIG. 25B, except that the battery material is deposited on the back of the sheet, i.e., on the side opposite the active parts or connections of circuit 2510.

FIG. 26C shows a perspective view of a processed sheet 2669. Sheet 2669 includes a plurality of devices or circuits 2510 each having a battery 2320 on the back. FIG. 26D shows a perspective view of diced final devices 2600 after being dices or cut apart. FIG. 26E shows a perspective view of wired diced final device 2600 after being wired, e.g., by wires 2615 and 2616 as shown, or by deposited traces (not shown) that extend electrical connections from the top to the bottom of device 2600.

In some embodiments, a roll of flexible fabric 2661 suitable for use as a substrate for direct energy conversion has deposited on it the necessary elements and/or layers to form the desired unit (such as a photovoltaic cell) using roll-to-roll concepts. The roll is then taken to the energy deposition tool 2660 which is also configured to operate in a roll-to-roll mode. The battery 2320 is fabricated on the backside (the side opposite the active side of the device, e.g., the side having the light-reception face of a photovoltaic cell) of the roll. Electrical connection is made after fabrication using hardwire techniques, such as shown in FIG. 26E.

In other embodiments such as shown in FIGS. 24B–24F, a roll of flexible fabric 2461 suitable for use as a substrate for direct energy conversion (e.g., for a photovoltaic cell) is deposited with materials to form a solid-state lithium battery using roll-to-roll concepts in system 2460. The resulting roll 2463 is then taken to the direct energy conversion materials deposition tool 2465 which is also configured to operate in a roll-to-roll mode. The direct energy conversion material 2430 is deposited directly on the solid-state battery 2320. In some embodiments, electrical connection is made through vias formed during battery and device fabrication such as shown in FIG. 23.

In yet other embodiments, roll 2461 above is replaced by a different substrate, such as wafer 2961 of FIG. 29A described below, also suitable for use in direct energy conversion. The fabrication tools 2960 and 2965 are also configured to handle the new substrate form factor such as square plates or round wafers.

In still other embodiments, roll 2661 above is replaced by a different substrate, such as wafer 2971 of FIG. 29E below, also suitable for use in direct energy conversion. The fabrication tools 2960 and 2965 are also configured to handle the new substrate form factor such as square plates or round wafers.

Thus, the present invention provides a method for integrating solid-state lithium batteries with direct energy conversion materials on a flexible fabric. Further, the present invention provides a method for integrating solid-state lithium batteries with direct energy conversion materials on a rigid substrate.

FIG. 26F shows a perspective view of a hearing aid 2690 incorporating a wired diced final device 2600. In some embodiments, device 2600 includes a photovoltaic cell 2650 for recharging battery 2320 the operates hearing aid 2690. In some embodiments, sound transducers of conventional materials such as piezo-electric materials are deposited as layers by system 2660 to be used as the microphone and speaker of hearing aid 2690.

Figure 27A:
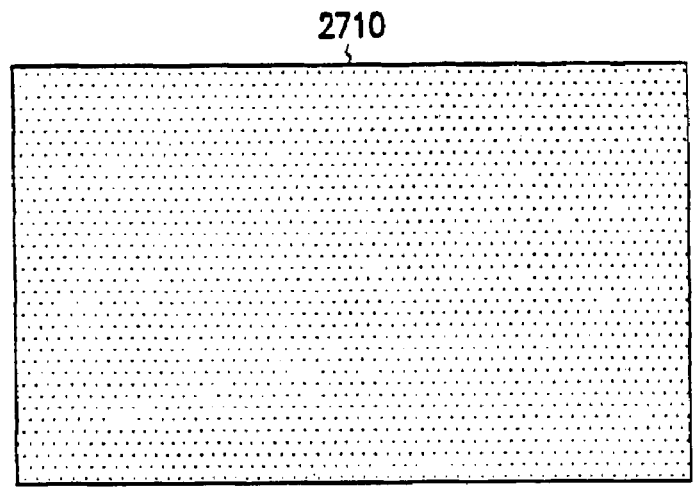
FIG. 27A shows a plan view of a starting substrate of an embodiment that will have an integrated battery and device sharing a common terminal.
Figure 27F:
FIG. 27F shows an elevation view of the starting substrate of FIG. 27A.
Figure 27B:
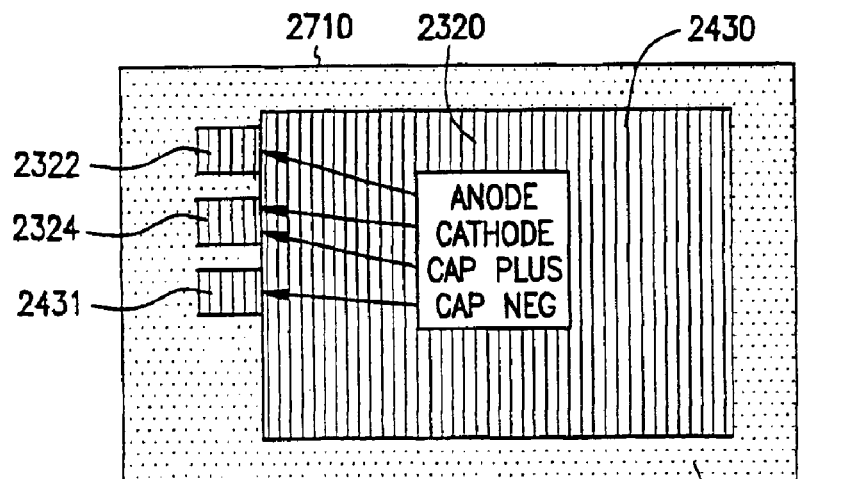
FIG. 27B shows a plan view of the substrate of FIG. 27A after deposition of the integrated battery and device sharing a common terminal.
Figure 27G:
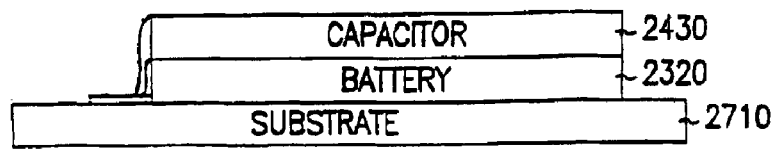
FIG. 27G shows an elevation view of the partially built device of FIG. 27B.
Figure 27C:
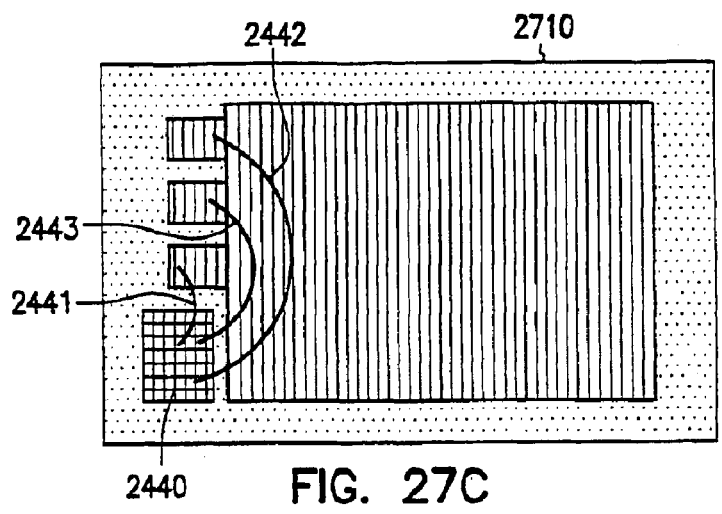
FIG. 27C shows a plan view of the substrate of FIG. 27B after placing and wiring a separately fabricated chip connected to the integrated battery and device sharing a common terminal.
Figure 27H:
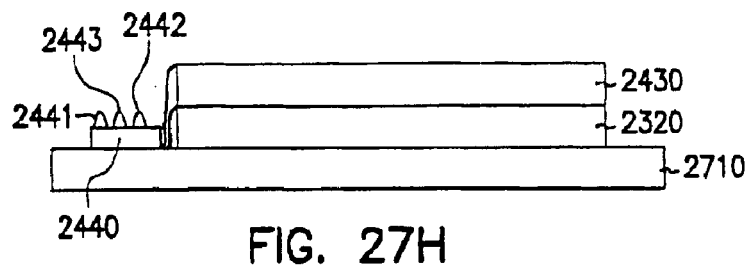
FIG. 27H shows an elevation view of the partially built device of FIG. 27C.
Figure 27D:
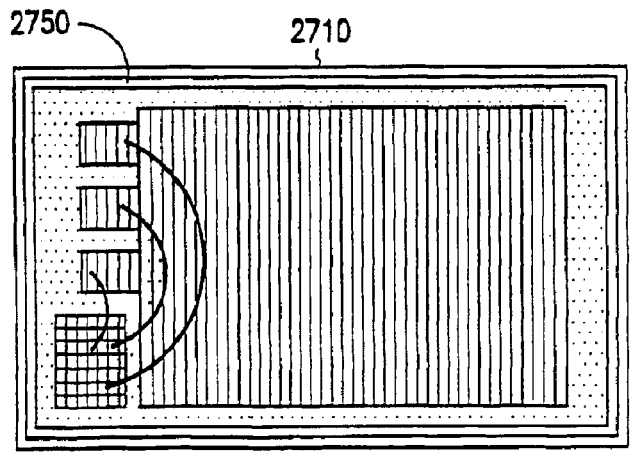
FIG. 27D shows a plan view of the substrate of FIG. 27C after placing and wiring a loop antenna.
Figure 27I:
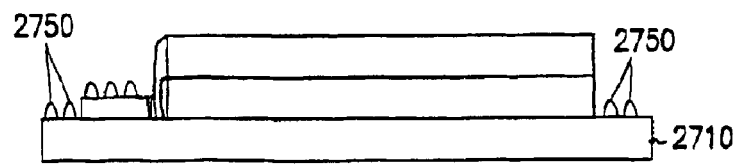
FIG. 27I shows an elevation view of the partially built device of FIG. 27D.
Figure 27E:
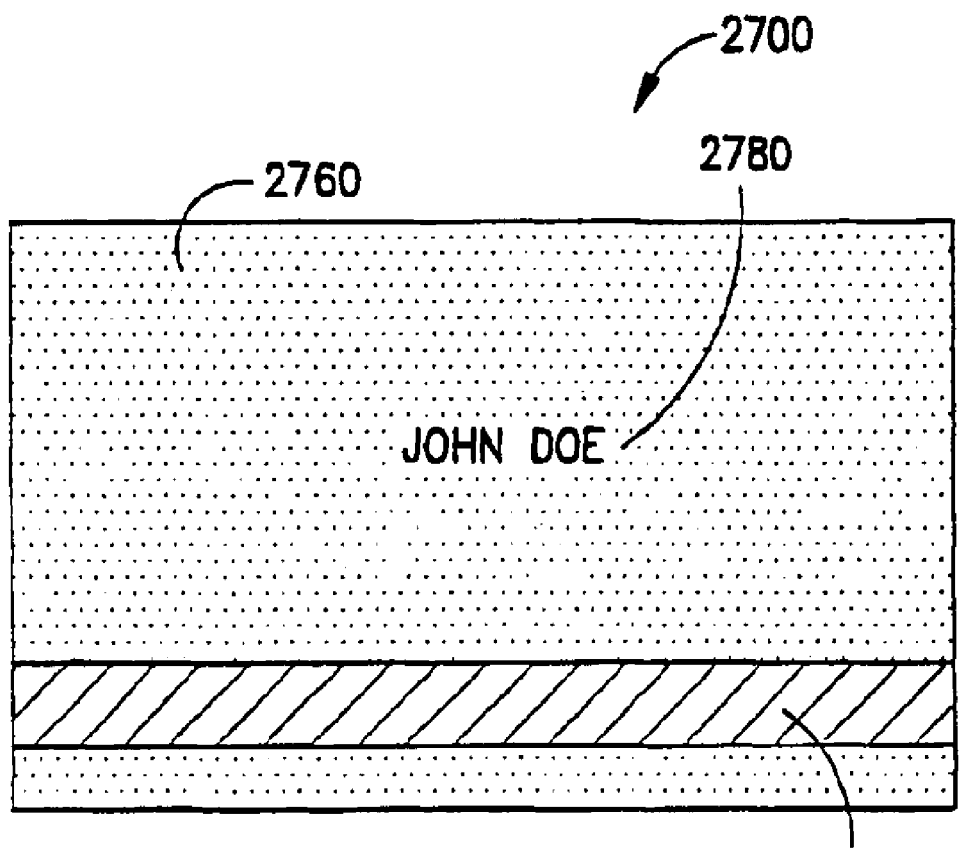
FIG. 27E shows a plan view of the substrate of FIG. 27D after a top encapsulation layer has been deposited.
Figure 27J:
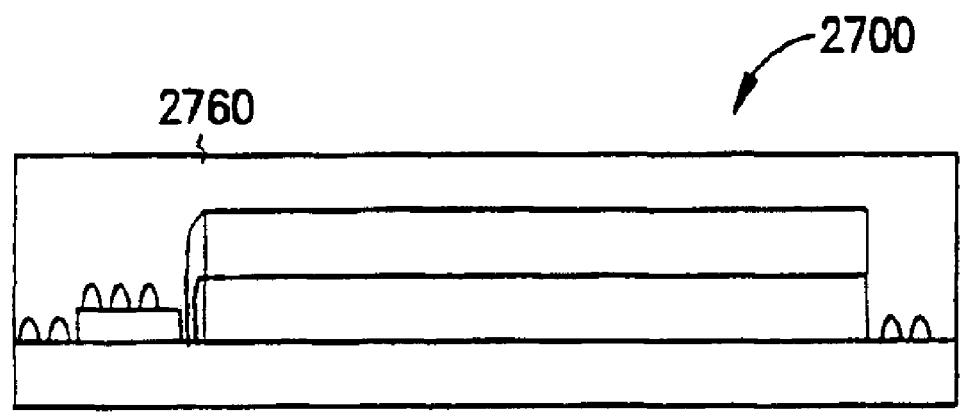
FIG. 27J shows an elevation view of the device of FIG. 27E.

FIG. 27A shows a plan view of a starting substrate 2710 of an embodiment that will have an integrated battery and device sharing a common terminal. FIG. 27F shows an elevation view of the starting substrate of FIG. 27A. FIG. 27B shows a plan view of the substrate 2710 of FIG. 27A after deposition of the integrated battery 2320 and device 2430 sharing a common terminal. In some embodiments, integrated battery 2320 and device 2430 are a thin-film battery and supercapacitor having electrical connections 2322, 2324, and 2431 such as shown and described in FIG. 24A above. FIG. 27G shows an elevation view of the partially built device of FIG. 27B. FIG. 27C shows a plan view of the substrate of FIG. 27B after placing and wiring a separately fabricated chip 2440 connected by wires 2441, 2442, and 2443 to the integrated battery 2320 and device 2430 sharing common terminal 2324. FIG. 27H shows an elevation view of the partially built device of FIG. 27C. FIG. 27D shows a plan view of the substrate 2710 of FIG. 27C after placing and wiring a loop antenna 2750. FIG. 27I shows an elevation view of the partially built device of FIG. 27D. FIG. 27E shows a plan view of the final device 2700 having the partially built device of FIG. 27D after a top encapsulation layer 2760 has been deposited. FIG. 27J shows a cross-section elevation view of the device 2700 of FIG. 27E. The elevational views of FIGS. 27E–27J are not to scale. In some embodiments, device 2700 is approximately the size and thickness of a common credit card. In some embodiments, a magnetic strip 2770 and raised lettering 2780 are also fabricated on device 2700.

Figure 27K:
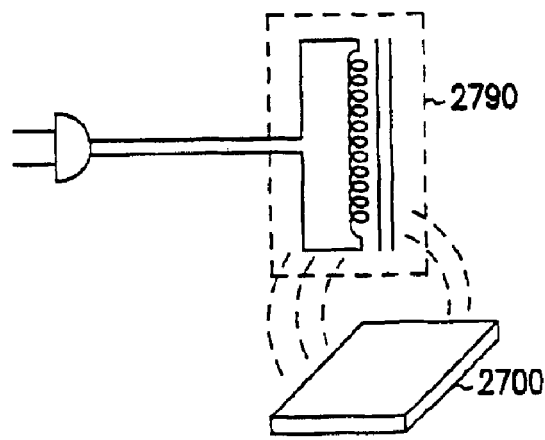
FIG. 27K shows an perspective view of the device of FIG. 27E at a magnetic-recharging station.

FIG. 27K shows an perspective view of the device of FIG. 27E at a magnetic-recharging station. In the embodiment shown, coil 2790 uses house current to generate a 60 Hz magnetic field, and together with coil 2750, form a transformer inducing current flow in coil 2750, which is rectified and used to recharge battery 2320.

Figure 27L:
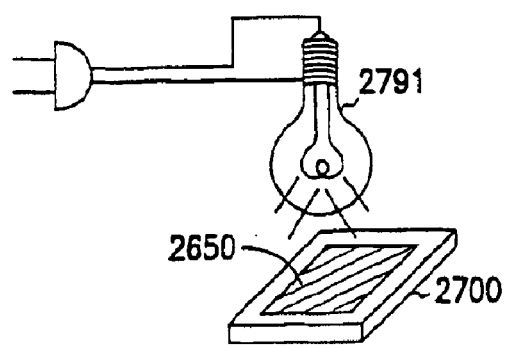
FIG. 27L shows an perspective view of the device of FIG. 27E at a light-recharging station.

FIG. 27L shows a perspective view of a device 2700 of FIG. 27E, but further including a photovoltaic cell 2650, at a light-recharging station that includes lamp 2791. In some embodiments, device 2700 is fabricated in a shape to fit in the ear, includes sound transducers, and functions as a hearing aid that can be recharged an indefinite number of times, eliminating the need to replace its battery.

Figure 27M:
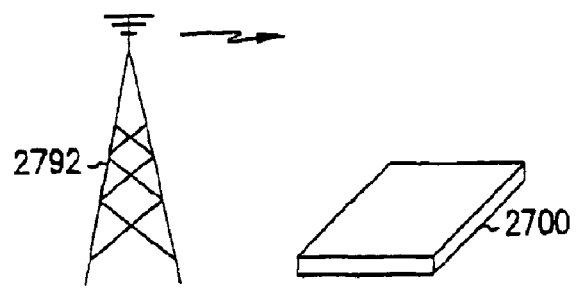
FIG. 27M shows a schematic of the device of FIG. 27E at a radio-wave-recharging station.

FIG. 27M shows a schematic of the device of FIG. 27E at a radio-wave-recharging station 2792. Radio waves from radio-wave-recharging station 2792 are picked up by antenna 2750, and the received radio wave's power is scavenged to recharge battery 2320 using a conventional recharging circuit, e.g., implemented in circuit 2440.

Solid-state rechargeable batteries such as those described above have the unique ability of being integrated directly with the electronics they will power. Further integration of thin-wire antenna/coil 2662 or 2750 to be used as one of the coils of a two-part transformer such as shown in FIG. 27K and/or RF-scavenging technology such as that used in keyless entry systems allows the recharging of the solid-state thin-film battery 2320 wirelessly (through the air). Using techniques already common in RF I.D. tagging, the communicated energy is converted into a D.C. voltage and used to perform functions on board. In the case where a battery already exists on board, the D.C. voltage is used to power up recharge circuitry to wirelessly recharge the on-board battery.

Certain needs exist within industry that would benefit from the integration of energy, storage communication and electronics on a single platform. One example is control of warehouse inventories where a small "credit card" is attached to an item in the warehouse. On board the "credit card" is an antenna, supercapacitor, solid-state battery and all required electronics. When the controller needs to know something about the package, the warehouse is queried via cellular or other wireless means with the I.D. of the package in question. The query "wakes up" the package and entices it to respond with whatever data is programmed to be released. The supercapacitor discharges into the antennae-driving circuitry bursting the data out to the central computer. At the same time, the electronics on the credit-card form factor device perform a self evaluation to see if any anomalies have or are occurring such as "battery needs charging." If the answer is yes, the central computer sends a signal of appropriate length to recharge the on-board battery using technology described herein.

Another application seeing significant enhancement from the integration of energy, communication and electronics on a single platform is an implantable device such as a pacemaker. This technology allows a battery having a very large number (if not infinite) charge/discharge cycles to be implanted as part of a pacemaker. When a "battery-low condition" is encountered, the battery is remotely recharged through the body using AC magnetic fields, sound or ultrasound, radio-frequency or other energy sources.

Solid-state processes are used to integrate electronics, solid-state rechargeable battery, and antenna on a single platform such as a "credit card" form factor. This is possible by using the low-temperature processes for solid-state batteries and supercapacitors described.

The present invention provides a platform integrating electronics, solid-state rechargeable batteries, and antenna on a single platform such as a credit card or implantable device allowing remote wireless recharging of the on-board battery.

FIGS. 27A–27J show a fabrication sequence if some embodiments of an example of a credit-card form factor I.D. tag with remote recharge capability.

Figure 31A:
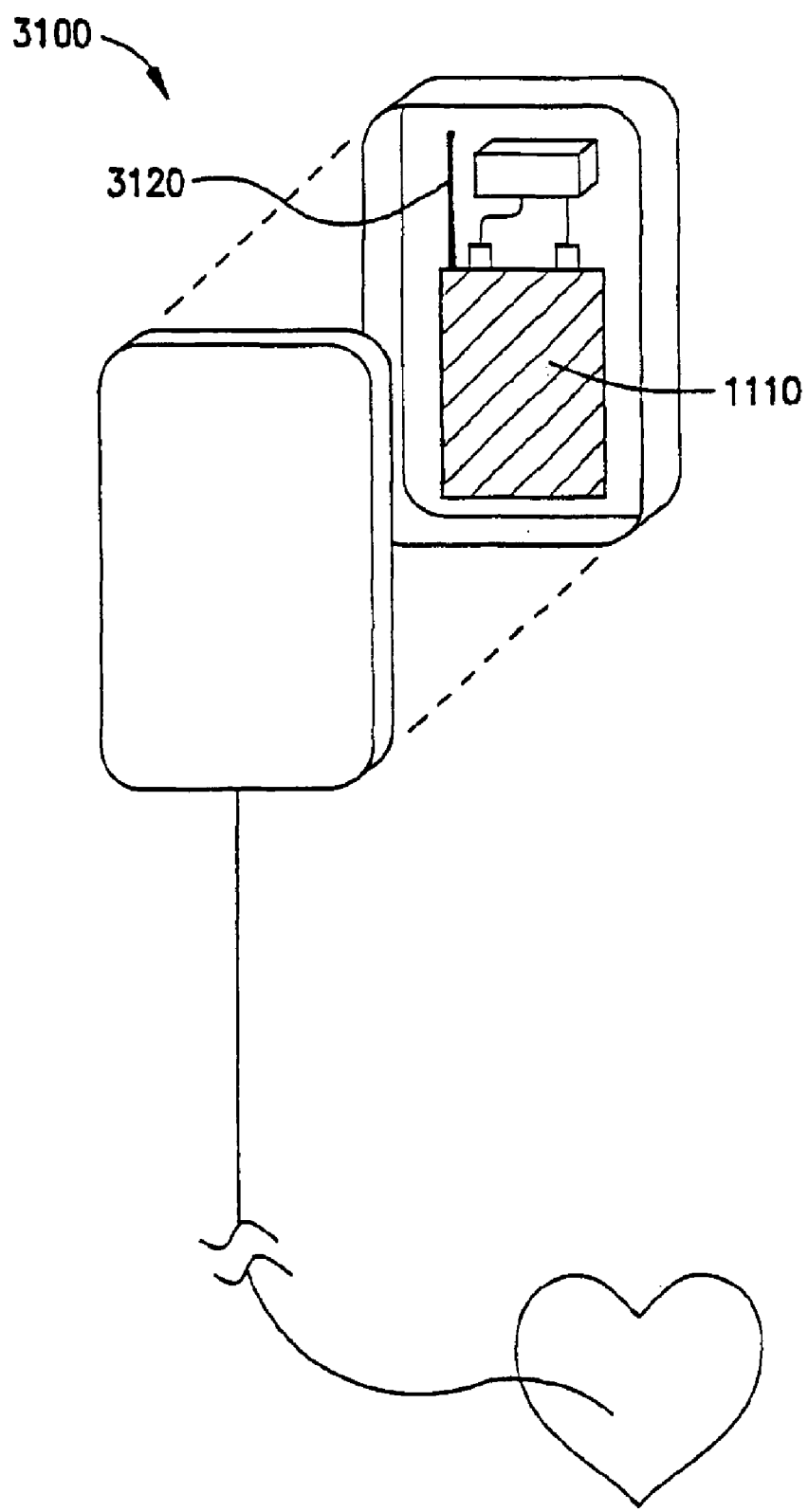
FIG. 31A is an exploded perspective view of a pacemaker according to this invention.
Figure 31B:
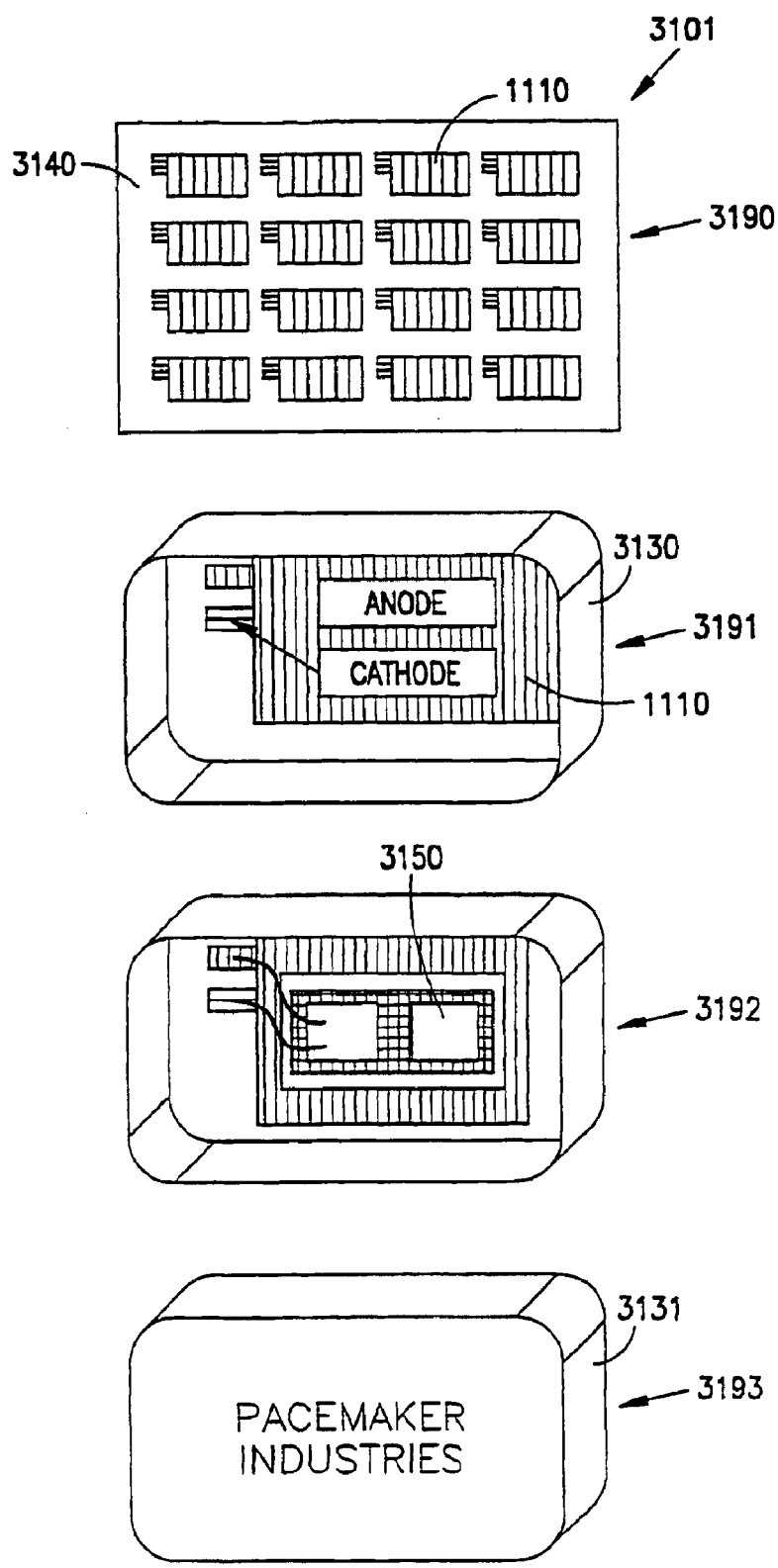
FIG. 31B is an exploded perspective view of one pacemaker as it is being formed.

FIG. 31B shows a fabrication sequence for an example of an implantable device such as a pacemaker 3101. This method starts with a substantially flat sheet deposited with batteries, which is then cut apart and formed into a three-dimensional shape. The method is otherwise similar to that of FIG. 31C.

Figure 31C:
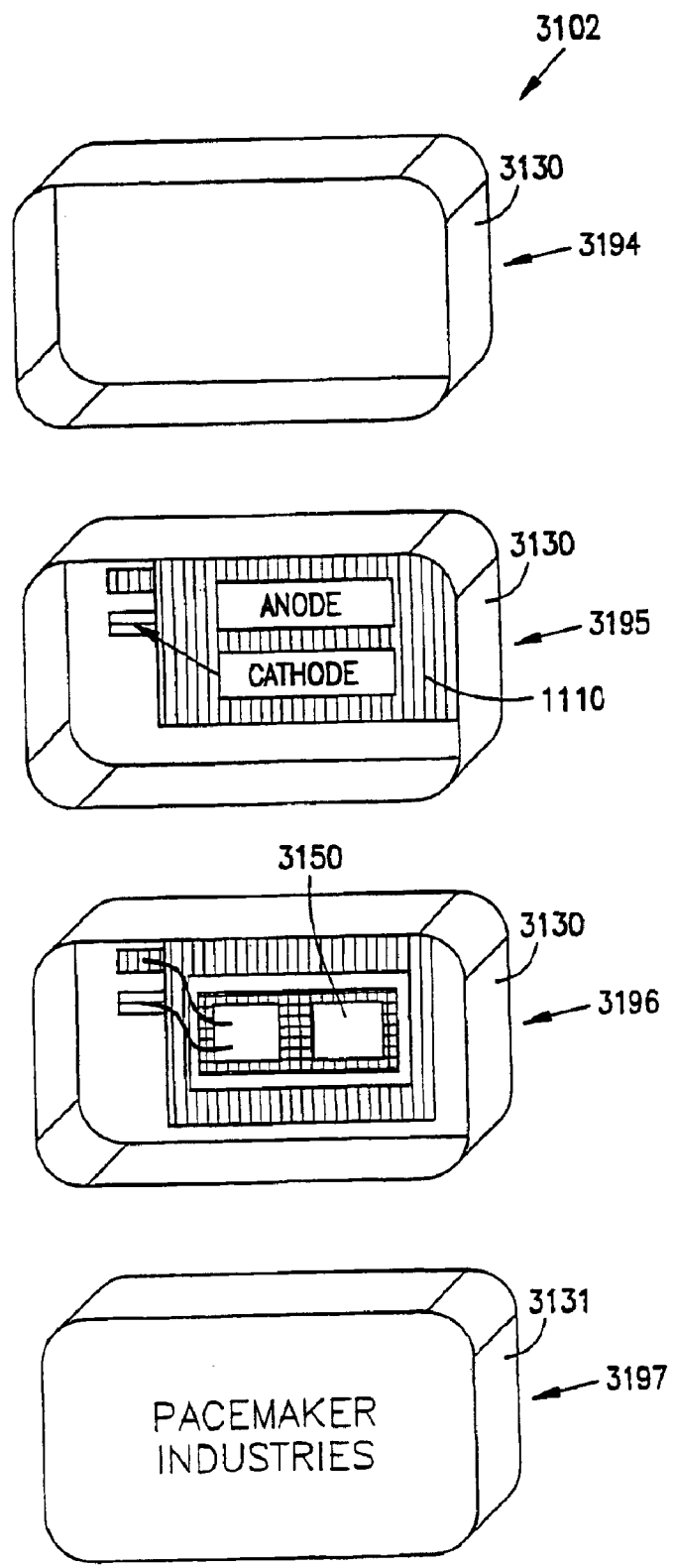
FIG. 31C is an exploded perspective view of another pacemaker as it is being formed.

FIG. 31C shows one method for making a pacemaker 3102. The method includes a plurality of steps carrying the reference numbers 3194, 3195, 3196 and 3197. The pacemaker 3102 includes a first half 3131 and a second half 3130. In the initial step, 3194, the second half 3130 is provided. A battery cell 1110 is formed on an interior surface of the pacemaker 3102, as shown by step 3195. The single cell 1110 is deposited on the interior surface, as shown by step 3195. The electronics 3150 are then placed onto the battery 1110 to form a circuit with the battery 1110, as depicted by step 3196. The first half 3131 of the enclosure is placed over the second half 3130 to form the assembled pacemaker 3102, as depicted by step 3197.

Solid-state rechargeable batteries such as those described above have the unique ability of being integrated directly with the electronics they will power. Further integration of thin-wire antenna and an energy burst device such as a supercapacitor would allow the device to communicate over large distances via any possible number of current communication methods including but not limited to cellular.

This invention relates to solid-state rechargeable batteries and the integration of such with wireless communication (antennae and electronics), supercapacitor and conventional electronics on a single platform.

Certain needs exist within industry that would benefit from the integration of energy, communication and electronics on a single platform. One example is control of warehouse inventories where a small "credit card" is attached to an item in the warehouse. On board the "credit care" are an antenna, supercapacitor, solid-state battery and all required electronics. This "credit card" allows tracking of location, time at location, description of item in question and/or information on the environment. When the controller needs to know something about the package, the warehouse is queried via cellular or other wireless means with the I.D. of the package in question. The query "wares up" the package and entices it to respond with whatever data is programmed to be released. The supercapacitor discharges into the circuitry driving the antennae bursting the data out to the central computer. At the same time, the electronics on the "credit card" performs a self evaluation to see if any anomalies have or are occurring such as battery needs charging. If the answer is yes, the central computer could send a signal of appropriate length to allow recharge of on-board battery using technology described above.

Solid-state processes are used to integrate electronics, solid-state rechargeable battery, supercapacitor and antenna on a single platform such as a "credit card" form factor. This is possible by using the low-temperature processes for solid-state batteries and supercapacitors described above.

Thus, the present invention provides for integrating electronics, solid-state rechargeable batteries, supercapacitors and antenna on a single platform such as a credit card or implantable device.

Method of Recycling and Re-using Solid-state Lithium-ion Batteries

FIG. 28A shows an elevation view of a battery 2800 having stacked cells 2801. Each cell includes an anode tab 2802 and a cathode tab 2803, wherein all of the anode tabs 2802 are soldered together, and all of the cathode tabs 2803 are soldered together. Optionally, battery 2800 is encapsulated with a potting material.

FIG. 28B shows a plan view of a single battery cell 2801 after recycling. In some embodiments, the anode tab 2802 and the cathode tab 2803 are "tinned" (covered with fresh solder) and/or solder bumped to facilitate reassembly soldering operations.

FIG. 28C shows a process 2810 used for recycling. Process 2810 includes providing batteries 2800 to be recycled into input bin 2820. In some embodiments, the batteries are de-potted at de-pot station 2822, de-soldered at de-solder station 2824, tested at test station 2826, and outputted into sorted output bins 2828 based on the testing results.

Of the 2 billion rechargeable batteries consumed in the United States in 1998, only about 300 million were actually recycled. That means about 1.7 billion recyclable batteries made it into landfills. Although more and more of these batteries are technically environmentally safe, this still represents a significant load on the landfill situation in the USA. The present invention provides a solution that will have its greatest impact as solid-state lithium-ion batteries begin to dominate the rechargeable battery market. In this invention, solid-state lithium-ion batteries have a date code and/or recycle value associated with them. Because of the very large (over 40,000) number of charge/discharge cycles possible with solid-state lithium batteries, the average expected life of a cell could exceed 100 years. It is therefore very likely that the product in which the cell is placed will lose its usefulness well before the battery cell is depleted. Thus, when the battery reaches the end of its useful life based on the obsolescence of the product it was in, the consumer will be enticed to recycle the battery based on the value returned to the consumer in exchange for recycling. This value could be a function of the date code and application the battery was used in. The recycler 2810 then disassembles the unit 2800, tests the single cells 2801, and then rebuilds the cells in whatever configuration is most in demand at that time. The rebuilt unit could then be sold at an appropriate cost and warranty on performance.

This invention relates to recycling of rechargeable batteries, specifically the recycling of batteries that are manufactured in such a way so as to allow the disassembly of the individual battery cells upon recycling.

For years the automotive industry has recycled certain high-cost components of the automobile. Using this philosophy, the present invention applies those principles to the recycling of rechargeable batteries. As battery technology advances, the batteries are actually outlasting the products they were designed for. The conventional solution is to depend on the consumer to recycle the no-longer useful battery by taking it to some place that will accept the battery. The data suggests that this is wishful thinking, as fully 80% of Americans do not recycle their rechargeable batteries. Rather, they throw them into the garbage and the battery ends up in a landfill. Although the newer battery chemistries are relatively benign to the environment, the sheer bulk of the disposed batteries can represent an enormous strain on landfills. This invention allows enticement of the consumer to recycle the batteries by offering a cash reward, or other inducement such as reduced cost on new batteries, in exchange for recycling. Since money is involved, this program should be able to be implemented on a wide scale making participation likely.

In one embodiment, rechargeable battery manufacturers are encouraged to manufacture their products in such a way that upon recycling, the battery can be broken down into individual cells and these cells rebuilt into "new" batteries. In some embodiments of the present invention provide such a recycling program, and provide batteries with features to facilitate recycling, for example, marking one or more of the cells of a battery with a code indicating such information as date of manufacture, voltage, capacity, value, composition physical size, and/or weight. An example is a cell-phone battery having a capacity of 1000 mAh (milliampere hours). Some embodiments involve the parallel assembly of approximately 10 individual cells into a battery pack that would have a capacity of 1000 mAh. These individual cells are fabricated on a grid that provides bonding tabs allowing the configuration of the cells in a variety of modes. Upon recycling, the batteries are de-potted, de-soldered and analyzed for robustness. Cells having data codes and test results indicating substantial life remaining would be repackaged according to market needs. In some embodiments, recycling rechargeable batteries involves the breaking down of the battery pack into individual cells which are tested and re-assembled into usable battery packs. Some embodiments include a method of determining the viability of recycled battery cells for use in rebuilt batteries such as measuring the charge-discharge voltage-current curve over one or more cycles. Some embodiments include a method of de-potting batteries such that the individual cells are accessible and not damaged, such as using a plastic potting compound that can later be dissolved using a solvent and/or heat that does not deteriorate the battery. Some embodiments include a method of disconnecting cells from the original battery pack and re-connecting into a new configuration, such as having solder tabs that extend beyond the battery pack so that the solder tabs can be desoldered without substantially heating the battery itself. Some embodiments include a recycling system based loosely on the system used by the automotive industry in rebuilding of starters, alternators etc. and the techniques used by lead acid battery outlets.

Figure 29A:
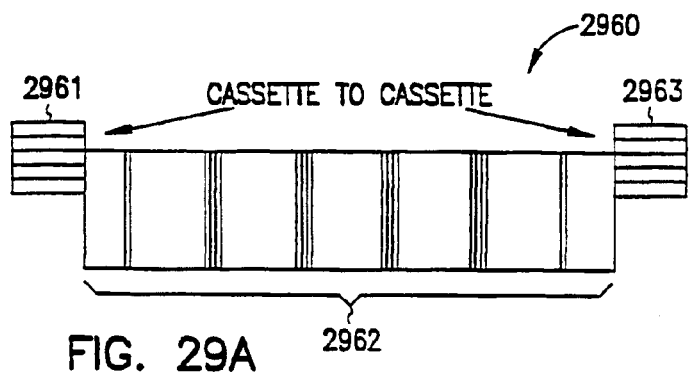
FIG. 29A shows a block diagram of a layer-deposition system 2960.
Figure 29B:
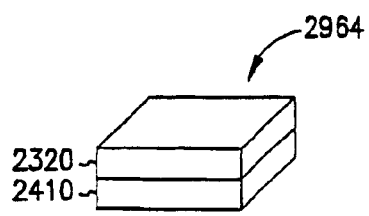
FIG. 29B shows a perspective view of a partially processed wafer 2964.

FIG. 29A shows a block diagram of a layer-deposition system 2960. System 2960 has layer deposition sections 2962 much the same as those of FIG. 2460 of FIG. 24B, except that it is set up to deposit layers onto wafers 2961 (or onto diced ICs 2510 rather than onto flexible substrates), resulting in processed wafers 2963. FIG. 29B shows a perspective view of a partially processed wafer 2964 having battery material 2320 on wafer 2961 or IC 2410.

Figure 29C:
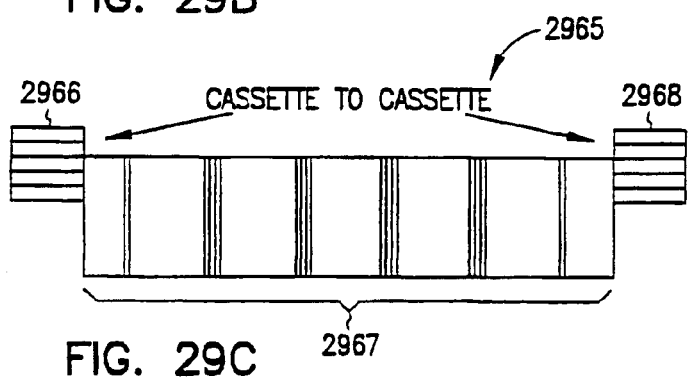
FIG. 29C shows a block diagram of a layer-deposition system 2965.
Figure 29D:
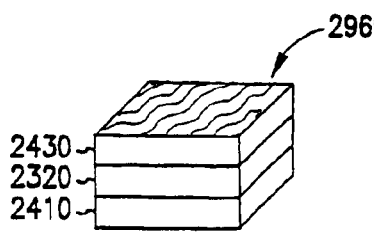
FIG. 29D shows a perspective view of a processed wafer 2969.

FIG. 29C shows a block diagram of a layer-deposition system 2965. System 2965 has layer deposition sections 2962 much the same as those of FIG. 2465 of FIG. 24D, except that it is set up to deposit layers onto wafers 2966 (or onto diced ICs 2510 rather than onto flexible substrates) by layer-deposition sections 2967, resulting in processed wafers 2968. FIG. 29D shows a perspective view of a processed sheet 2969 having battery material 2320 on wafer 2961 or IC 2410 and covered by a device 2430 such as a photovoltaic cell.

Figure 29E:
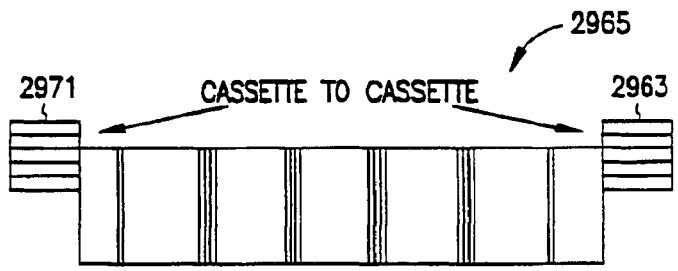
FIG. 29E shows a block diagram of a layer-deposition system 2965.
Figure 29F:
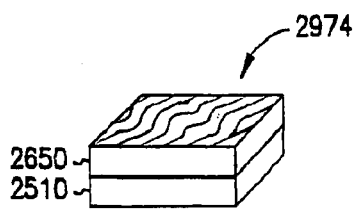
FIG. 29F shows a perspective view of a partially processed wafer 2974.
Figure 29G:
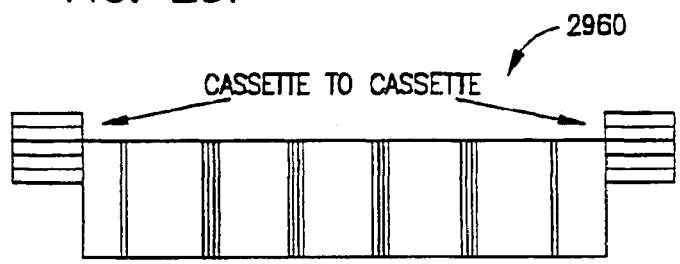
FIG. 29G shows a block diagram of a layer-deposition system 2960.
Figure 29H:
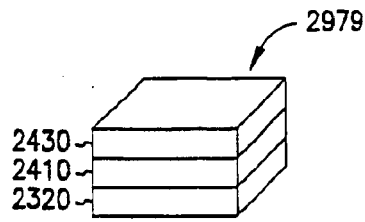
FIG. 29H shows a perspective view of a processed wafer 2979.
Figure 29I:
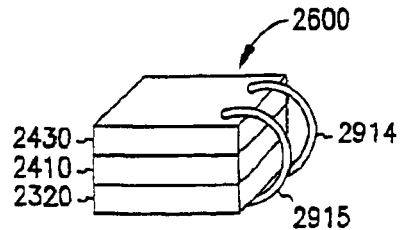
FIG. 29I shows a perspective view of wired diced final device 2600.

FIG. 29E shows a block diagram of a layer-deposition system 2965. In some such embodiments, system 2965 deposits layers forming a photovoltaic cell device 2650 onto a wafer 2971 or IC 2510. FIG. 29F shows a perspective view of a partially processed wafer 2974. FIG. 29G shows a block diagram of a layer-deposition system 2960. In some such embodiments, system 2960 deposits layers of a battery 2320. FIG. 29H shows a perspective view of a processed wafer 2979. In some embodiments, wafer 2979 represents a single device, and in other embodiments, wafer 2979 is diced or cut into a plurality of individual devices and then wired as necessary to connect the signals on the top of the device to the bottom of the device. FIG. 29I shows a perspective view of wired diced final device 2600 having wires 2914 and 2915.

Figure 30:
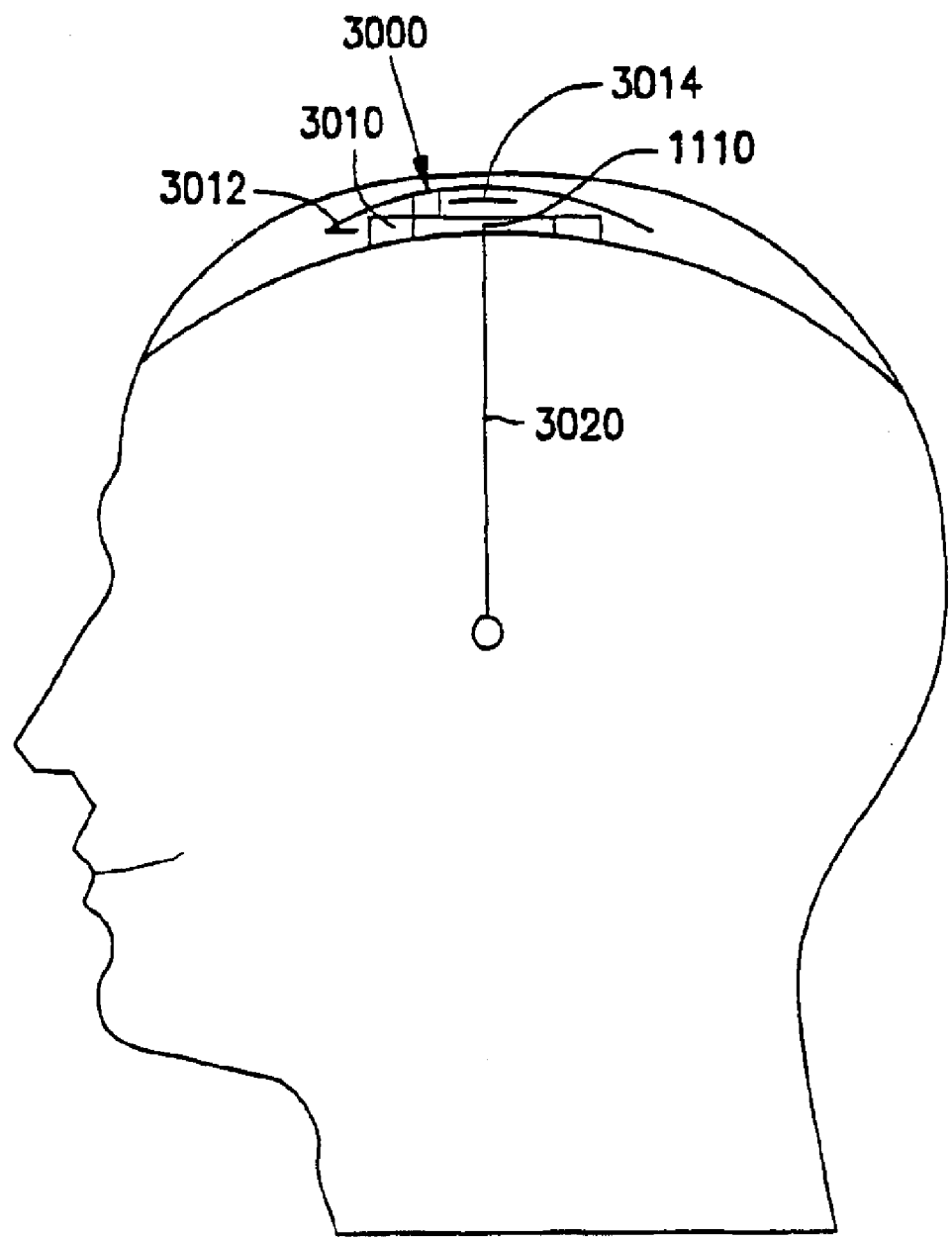
FIG. 30 is a perspective view of an implantable device according to this invention.

Turning now to FIGS. 30, 31 and 32, specific examples of devices will now be provided. FIG. 30 shows an implantable device 3000 used to stimulate specific portions of the brain. One use of such device 3000 is for deep brain neural stimulation, for example, in order to treat Parkinson's Disease. By sending signals to a specific portion of the brain the tremors associated with Parkinson's Disease may be reduced. In the past, a lead or conductor was implanted in the brain so that electrical signals may be sent to the specific area of the brain for reducing tremors. The lead passes under the skull and through the neck to a pocket near the patient's chest in current versions. As shown in FIG. 30, after a burr hole has been made in the skull, a port 3010 is placed in the burr hole. The port 3010 includes a cap 3012, which is used to hold the lead in place during implantation as well as after implantation. In this particular invention, the cap 3012 is made of a suitable biocompatible material. Imbedded within the cap is a battery cell 1110 or a series of battery cells 1110. The electronics necessary to deliver the signals at a desired rate or programmable rate is also imbedded within the cap 3012. An RF antenna 3014 is also placed within the cap so that the battery 1110 imbedded within the cap 3012 can be recharged by passing radio frequency into the cap or inductively coupling the required energy into the cap. Another embodiment may use the lead 3020 for an energizing antenna and may include a separate antenna for programming the electronics used to deliver signals to the brain.

FIG. 31A is directed toward a pacemaker 3100. Rather than include separate batteries within the case of the pacemaker 3100, the enclosure, or at least one enclosure portion, includes a battery 1110 or a series of cells 1110. The pacemaker 3100 may include an antenna 3120 which is used to direct radio frequency toward the pacemaker for recharging of the battery 1110 that is positioned within the case or enclosure of the pacemaker 3100.

FIG. 31B shows the method for making the pacemaker 3101. The method is comprised of a plurality of steps carrying the reference numbers 3190, 3191, 3192 and 3193. The pacemaker 3100 includes a first half 3131 and a second half 3130. A plurality of battery cells 1110 are formed on a substrate material 3140, as shown by step 3190. The substrate material 3140 is diced or cut resulting in a single cell 1110 on the sheet as diced. The single cell 1110 is adhesively bonded to the second half 3130 of the pacemaker 3100, as shown in step 3191. The electronics 3150 are then placed onto the battery 1110 to form a circuit with the battery 1110, as depicted by step 3192. The first half 3131 of the enclosure is placed over the second half 3130 to form the assembled pacemaker 3100.

Figure 32A:
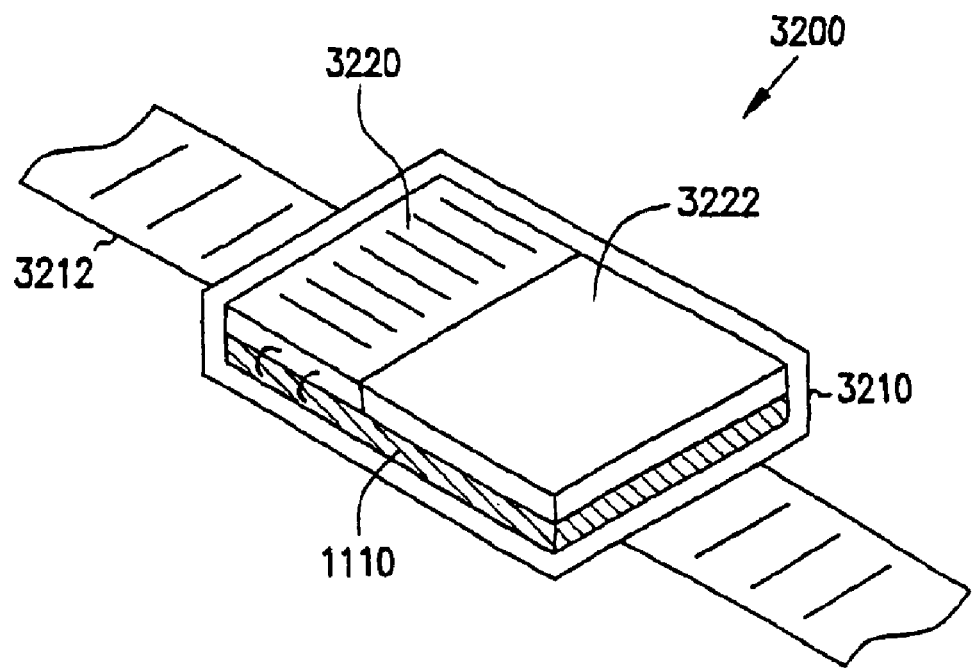
FIG. 32A is a perspective view of a first embodiment of a watch of the invention.

FIG. 32A is a perspective cutaway view of a watch 3200. The watch includes a case 3210 and a band 3212 for strapping onto a person's wrist. Within the case 3210 is a solar cell 3220 and an LCD 3222. The solar cell 3220 is attached to the battery or series of battery cells 1110. The LCD 3222 is attached to the battery and electronic (not shown). The battery powers the LCD 3222 and is associated to electronics associated with the watch 3200. The solar cell 3220 recharges the battery 1110 more or less continuously. Both the solar cell 3220 and the LCD 3222 appear at the crystal or glass portion of the watch. Advantageously, this type of watch can be sealed forever so that it can be made absolutely watertight.

Figure 32B:
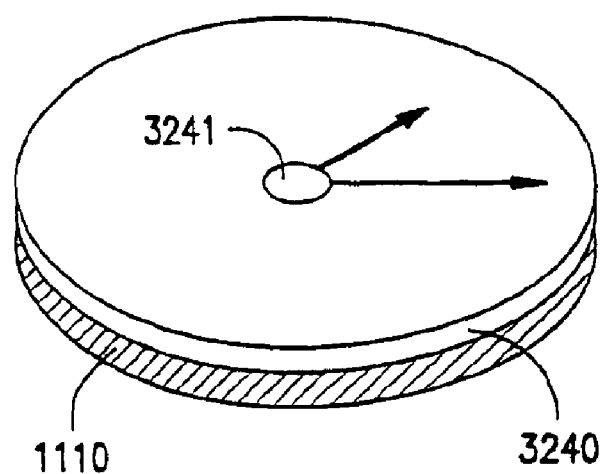
FIG. 32B is a perspective view of a second embodiment of a watch.

Another embodiment of a watch is shown in FIG. 32B. In this particular instance, a circular-shaped solar cell 3240 is positioned atop a circular-shaped battery cell 1110. The circular-shaped solar cell includes an opening 3241 therein. A set of hands for an analog watch may be inserted through the opening. The crystal or glass face of the watch will then be opened to the solar cell 3240 so that it can continuously charge the battery 1110, which in turn powers the working portion of the watch.

CONCLUSION

Described above are an improved method and system for fabrication of solid-state energy devices and the solid-state energy devices per se. In some embodiments, the present method focuses the energy for forming films having fewer defects and/or certain crystal properties directly at a certain film. By focusing the energy, collateral damage to other parts of a structure or device are minimized. Accordingly, a wider array of materials, devices and structures are available with which an energy storage device or energy conversion device is fabricated according to the present invention.

In one embodiment, the method includes depositing a first film on a substrate by depositing a first material to a location on the substrate, and supplying energized ions of a second material different than the first material to the location on the substrate to control growth of a crystalline structure of the first material at the location. Electrolyte and anode layers are subsequently formed. In some embodiments, the film is "annealed" as it is deposited. In some embodiments, the energy "annealing" the film is only directed at the material of the film.

In one embodiment, the secondary source is an ion source with the capability of supplying energetic ions having an energy greater than 5 eV. In another embodiment, the energy range is about 5 eV to about 3,000 eV. In one embodiment, the energy range of is about 5 eV to about 1,000 eV. The energy range in a further embodiment is about 10 eV to about 500 eV. In another embodiment, the energy range is in the range of about 60 eV to 150 eV. In some embodiments, the energy is in the range of about 100 eV to about 200 eV. In some embodiments, the energy is in the range of about 50 eV to about 250 eV. In some embodiments, the energy is in the range of about 40 eV to about 275 eV. In some embodiments, the energy is in the range of about 30 eV to about 300 eV. In some embodiments, the energy is in the range of about 20 eV to about 350 eV. In some embodiments, the energy is in the range of about 15 eV to about 400 eV. In another embodiment, the energy range is about 140 eV.

In some embodiments, the cathode layer is formed without a post-deposition anneal step being performed thereon as the present method provides the necessary energy to grow a sufficiently crystalline layer by use of the secondary source. In some embodiments, the cathode layer is not annealed at all.

In some embodiments, the substrate is formed of a material that will degrade due to thermal effects at a high temperature such as an anneal temperature for conventional cathode thin films. In one embodiment, the substrate will thermally degrade at a temperature of less than 700 degrees Celsius. In one embodiment, the substrate will thermally degrade at a temperature of less than 300 degrees Celsius. In one embodiment, the substrate will thermally degrade at a temperature of less than 250 degrees Celsius. In one embodiment, the substrate will thermally degrade at a temperature of less than 100 degrees Celsius. In some embodiments, the thermal degradation temperature is about 600 degrees Celsius. In some embodiments, the thermal degradation temperature is about 550 degrees Celsius. In some embodiments, the thermal degradation temperature is about 500 degrees Celsius. In some embodiments, the thermal degradation temperature is about 450 degrees Celsius. In some embodiments, the thermal degradation temperature is about 400 degrees Celsius. In some embodiments, the thermal degradation temperature is about 350 degrees Celsius. In some embodiments, the thermal degradation temperature is about 300 degrees Celsius. In some embodiments, the thermal degradation temperature is about 250 degrees Celsius.

Some embodiments of the method include depositing a seed material on a first film to assist in the low energy deposition of the lithium intercalation material of a subsequent film thereon. In an embodiment, the seed material assists in orienting the crystal structure of the subsequent film. In some embodiments, the seed layer is an electrically conductive layer. In some embodiments, the seed material provides nucleation sites for the film deposited thereon. In some embodiments, the seed layer includes islands of material. In some embodiments, the seed layer includes at least one of Ta, TaN, Cr, and CrN. In some embodiments, the seed layer includes one or more of W, WN, Ru, and RuN. In some embodiments, the seed layer has a surface free energy that is higher than a surface free energy of film material being grown thereon.

Another aspect of the present invention provides structure and methods for controlling the temperature of the substrate and any films formed thereon during subsequent depositing steps. This allows a more temperature sensitive material to be used as the substrate while preventing thermal degradation effects of the substrate.

In one embodiment of the method, subsequent films, including the electrolyte film and the anode film, are deposited using a deposition source and another source. In one embodiment, the second source provides energy to orient the crystalline structure of the electrolyte film and the anode film and influence the stoichiometry of the resulting films. In some embodiments, these films are treated by energy from the second source treats the material from the deposition source as it directs material to the target substrate.

In another embodiment of the method, the battery, and/or layers of the battery are subject to a post fabrication cryogenic anneal to correct defects in the crystalline structure. In some embodiments, the cryogenic anneal is repeated multiple times. In some embodiments, the cryogenic anneal cools the battery to about negative (−)160 degrees Celsius to about negative (−)50 degrees Celsius. In some embodiments, the cryogenic anneal cools the battery to about negative (−)120 degrees Celsius to about negative (−)50 degrees Celsius. In some embodiments, the cryogenic anneal cools the battery to about negative (−)100 degrees Celsius to about negative (−)50 degrees Celsius. In some embodiments, the cryogenic anneal cools the battery to about negative (−)80 degrees Celsius to about negative (−)50 degrees Celsius. In some embodiments, the cryogenic anneal cools the battery to about negative (−)150 degrees Celsius. In some embodiments, the cryogenic anneal cools the battery to about negative (−)110 degrees Celsius. In some embodiments, the cryogenic anneal cools the battery to about negative (−)90 degrees Celsius. In some embodiments, the cryogenic anneal cools the battery to about negative (−)75 degrees Celsius. In some embodiments, the cryogenic anneal cools the battery to about negative (−)25 degrees Celsius.

Another important aspect of the methods described herein pertains to the quality of the crystalline materials, e.g., size, of the crystallites in the thin layer. Crystallite size relates to the electrical performance of lithium intercalation materials in lithium batteries and in other devices. Crystallite size in the layers deposited according to the methods described herein is adequately large to achieve commercially viable electrical properties in the devices described herein. In some embodiments, the crystallite size is greater than about 200 Angstroms. In some embodiments, the crystallite size is greater than about 300 Angstroms. In some embodiments, the crystallite size is greater than about 400 Angstroms. In some embodiments, the crystallite size is greater than about 500 Angstroms. In some embodiments, the crystallite size is greater than about 600 Angstroms. In some embodiments, the crystallite size is greater than about 650 Angstroms.

The energy-storage devices, such as thin-film batteries, capacitors, and supercapacitors include an ultra-thinned electrolyte film interposed between two electrode films. Such ultra-thinned electrolyte films improve electrical performance of the energy-storage devices by decreasing the resistance within the electrolyte layer while still maintaining the required electron insulating property between the two electrodes. In some embodiments, the electrolyte film allows ionic transport therethrough. In some embodiments, the film between the electrodes is a dielectric material. By using the methods described herein, such ultra-thin electrolyte films of high structural quality and stoichiometric control are fabricated.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled.

The invention claimed is:

1. A method of fabricating a solid-state energy-storage device, comprising:
   providing a substrate;
   depositing a first film layer on the substrate by a process that includes simultaneously:
   (a) depositing a first material to a location on the substrate, and
   (b) supplying energized ions of a second material different than the first material directed towards the first material to supply energy thereto and assisting growth of crystalline structure of the film layer during the deposition of the first material on the substrate;
   forming an electrolyte second layer on the first layer; and
   forming a third layer on the second layer, wherein providing the substrate includes forming a first contact layer on the substrate that at least partially separates the first layer from the substrate.

2. The method of claim 1, wherein providing the substrate includes forming a second contact layer on the substrate separate from the first contact layer.

3. The method of claim 1, wherein depositing the first layer includes using physical vapor deposition to direct the first material to the location on the substrate.

4. The method of claim 1, wherein the supplying the energized second material includes supplying ions having an energy within the range of about 5 to about 3000 eV.

5. The method of claim 1, wherein supplying the energized second material includes supplying ions from a source gas including $O_2$.

6. The method of claim 1, wherein supplying the energized second material includes supplying ions from a source gas including $N_2$.

7. The method of claim 1, wherein supplying the energized second material includes supplying ions from a source gas including a noble gas.

8. The method of claim 1, wherein supplying the energized second material includes supplying ions from a source gas including argon.

9. The method of claim 1, wherein supplying the energized second material includes supplying ions from a source gas including a hydrocarbon precursor.

10. The method of claim 1, wherein supplying the energized second material includes focusing a beam of the ions at the location on the substrate.

11. The method of claim 1, wherein supplying the energized second material includes supplying a non-focused beam of the ions.

12. The method of claim 1, wherein supplying the energized second material includes supplying ions having an energy within the range of about 5 eV to about 200 eV.

13. The method of claim 1, wherein supplying the energized second material includes controlling stoichiometry of a growing film of first material.

14. The method of claim 1, wherein supplying the energized second material includes supplying ions having an energy within the range of about 10 eV to about 500 eV.

15. The method of claim 1, wherein supplying the energized second material includes supplying ions having an energy within the range of about 60 eV to about 150 eV.

16. The method of claim 1, wherein supplying the energized second material includes supplying ions having an energy of about 140 eV.

17. The method of claim 1, wherein at least the depositing of the first film using chemical vapor deposition to direct the first material toward the substrate.

18. The method of claim 1, wherein at least the forming of the electrolyte second film includes using chemical vapor deposition to direct electrolyte material toward the substrate.

19. The method of claim 1, wherein at least the forming of the third film includes using chemical vapor deposition to direct third film material toward the substrate.

20. The method of claim 1, depositing the first layer includes depositing an intercalation material in the first layer to have a crystal orientation essentially perpendicular to a boundary between the first layer and the second layer; and wherein forming the third layer includes forming an anode for a thin-film battery.

21. The method of claim 1, wherein forming the electrolyte second layer on the first layer includes depositing a fifth material to a location on the substrate and at least partially in contact with the first layer, and supplying energized ions of a sixth material different than the fifth material to the location on the substrate to form the electrolyte second layer.

22. The method of claim 1, wherein forming the third layer on the electrolyte second layer includes depositing a third material to a second location at least partially in contact with the electrolyte second layer and separate from the first layer, and supplying energized ions of a fourth material different than the third material to the second location to control growth of a crystalline structure of the third material at the location to form the third layer.

23. The method of claim 1, wherein supplying the energized second material includes supplying particles of the energized second material simultaneously with the first material but along a path that is not coincident with a path along which the first material travels.

24. The method of claim 1, wherein supplying the energized second material includes supplying energized ions to the location on the substrate simultaneously with deposition of the first material.

25. The method of claim 1, wherein providing the substrate includes providing a substrate having a thermal degradation temperature of less than 700 degrees Celsius.

26. The method of claim 1, wherein providing the substrate includes providing a substrate having a thermal degradation temperature of less than about 300 degrees Celsius.

27. The method of claim 1, wherein providing the substrate includes providing a substrate having a thermal degradation temperature of less than about 250 degrees Celsius.

28. The method of claim 1, wherein the supplying the energized second material includes controlling growth of the first material into a crystalline structure.

29. The method claim 1, wherein the supplying of the energized second material includes supplying energized ions.

30. The method of claim 1, wherein the device is a thin-film lithium battery.

31. A method of fabricating a solid-state energy-storage device, comprising:
   providing a substrate;
   depositing a first film layer on the substrate by a process that includes simultaneously:
   (a) depositing a first material to a location on the substrate, and
   (b) supplying energized ions of a second material different than the first material directed towards the first material to supply energy thereto and assisting growth of crystalline structure of the film layer during the deposition of the first material on the substrate;
   forming an electrolyte second layer on the first layer; and
   forming a third layer on the second layer, wherein depositing the first layer includes depositing an intercalation material in the first layer to have a crystal orientation essentially perpendicular to a boundary between the first layer and the second layer, wherein depositing the intercalation first layer includes growing crystallite size of at least about 100 Angstroms.

32. The method of claim 31, wherein depositing the intercalation first layer includes growing crystallite size of at least about 200 Angstroms.

33. The method of claim 31, wherein depositing the intercalation first layer includes growing crystallite size of about 240 Angstroms.

34. The method of claim 33, wherein depositing the intercalation first layer includes depositing a $LiCoO_2$ material as the first layer.

35. The method of claim 34, wherein depositing the $LiCoO_2$ intercalation first layer includes depositing the $LiCoO_2$ intercalation first layer as a cathode layer.

36. The method of claim 31, wherein depositing the first layer includes using physical vapor deposition to direct the first material to the location on the substrate.

37. The method of claim 31, wherein the supplying the energized second material includes supplying ions having an energy within the range of about 5 to about 3000 eV.

38. The method of claim 31, wherein supplying the energized second material includes supplying ions from a source gas including $O_2$.

39. The method of claim 31, wherein supplying the energized second material includes supplying ions from a source gas including $N_2$.

40. The method of claim 31, wherein supplying the energized second material includes supplying ions from a source gas including a noble gas.

41. The method of claim 31, wherein supplying the energized second material includes supplying ions from a source gas including argon.

42. The method of claim 31, wherein supplying the energized second material includes supplying ions from a source gas including a hydrocarbon precursor.

43. The method of claim 31, wherein supplying the energized second material includes focusing a beam of the ions at the location on the substrate.

44. The method of claim 31, wherein supplying the energized second material includes supplying a non-focused beam of the ions.

45. The method of claim 31, wherein supplying the energized second material includes supplying ions having an energy within the range of about 5 eV to about 200 eV.

46. The method of claim 31, wherein supplying the energized second material includes controlling stoichiometry of a growing film of first material.

47. The method of claim 31, wherein supplying the energized second material includes supplying ions having an energy within the range of about 10 eV to about 500 eV.

48. The method of claim 31, wherein supplying the energized second material includes supplying ions having an energy within the range of about 60 eV to about 150 eV.

49. The method of claim 31, wherein supplying the energized second material includes supplying ions having an energy of about 140 eV.

50. The method of claim 31, wherein at least the depositing of the first film using chemical vapor deposition to direct the first material toward the substrate.

51. The method of claim 31, wherein at least the forming of the electrolyte second film includes using chemical vapor deposition to direct electrolyte material toward the substrate.

52. The method of claim 31, wherein at least the forming of the third film includes using chemical vapor deposition to direct third film material toward the substrate.

53. The method of claim 31, wherein depositing the first layer includes depositing an intercalation material in the first layer to have a crystal orientation essentially perpendicular to a boundary between the first layer and the second layer.

54. The method of claim 31, wherein forming the electrolyte second layer on the first layer includes depositing a fifth material to a location on the substrate and at least partially in contact with the first layer, and supplying energized ions of a sixth material different than the fifth material to the location on the substrate to form the electrolyte second layer.

55. The method of claim 31, wherein forming the third layer on the electrolyte second layer includes depositing a third material to a second location at least partially in contact with the electrolyte second layer and separate from the first layer, and supplying energized ions of a fourth material different than the third material to the second location to control growth of a crystalline structure of the third material at the location to form the third layer.

56. The method of claim 31, wherein supplying the energized second material includes supplying particles of the energized second material simultaneously with the first material but along a path that is not coincident with a path along which the first material travels.

57. The method of claim 31, wherein the device is a thin-film lithium battery.

58. A method of fabricating a solid-state energy-storage device, comprising:
   providing a substrate;
   forming a seed film on the substrate;
   forming a first film on the seed film by:
      (a) depositing a first material to a location on the seed film, and
      (b) supplying a second material different than the first material adjacent the location to control growth of a crystalline structure of the first material at the location;
   forming an electrolyte second film on the first film; and
   forming a third film on the electrolyte second film.

59. The method of claim 58, wherein forming the third film includes forming a second seed film on a surface of the electrolyte second film and thereafter forming the third film on the second seed film.

60. The method of claim 59, wherein the third film includes a lithium intercalation material, and wherein forming the second seed film includes depositing an amorphous seed material to diminish undesirable growth structures of the lithium intercalation material of the third film.

61. The method of claim 59, wherein the third film includes a lithium intercalation material, and wherein forming the second seed film includes depositing a nanocrystalline seed material with fine grains to diminish undesirable growth structures of the lithium intercalation material of the third film.

62. The method of claim 59, wherein forming the second seed film includes depositing an electrically conductive seed material.

63. The method of claim 62, wherein depositing seed material includes depositing a seed material comprising one or more of Ta, TaN, Cr, and CrN.

64. The method of claim 62, wherein depositing seed material includes depositing a seed material comprising one or more of, W, WN, Ru, and RuN.

65. The method of claim 58, wherein forming the second seed film includes depositing a seed material having a surface free energy that is higher than a surface free energy of the third film.

66. The method of claim 58, wherein forming the seed film includes depositing a seed material having a surface free energy that is higher than a surface free energy of the first film.

67. The method of claim 66, wherein cryogenically annealing includes first packaging the device prior to cryogenically annealing.

68. The method of claim 58, wherein the first film includes a lithium intercalation material, and wherein forming the seed film includes depositing an amorphous seed material to diminish undesirable growth structures of the lithium intercalation material of the first film.

69. The method of claim 58, wherein the first film includes a lithium intercalation material, and wherein forming the seed film includes depositing a nanocrystalline seed material with fine grains to diminish undesirable growth structures of the lithium intercalation material of the first film.

70. The method of claim 58, wherein forming the seed film includes depositing an electrically conductive seed material.

71. The method of claim 70, wherein depositing seed material includes depositing a seed material comprising one or more of Ta, TaN, Cr, and CrN.

72. The method of claim 70, wherein depositing seed material includes depositing a seed material comprising one or more of, W, WN, Ru, and RuN.

73. The method of claim 58, wherein the device is a thin-film lithium battery.

74. A method of fabricating a solid-state energy-storage device, comprising:
providing a substrate;
depositing a first layer on the substrate by:
(a) depositing a first material to a location on the substrate, and
(b) supplying energized particles of a second material different than the first material to the substrate adjacent the location to control growth of a crystalline structure of the first material at the location;
forming an electrolyte second layer on the first layer;
forming a third layer on the electrolyte second layer, and
after performing the above steps, cryogenically annealing the energy-storage device.

75. The method of claim 74, wherein supplying energized particles includes supplying energized ions.

76. The method of claim 75, wherein cryogenically annealing the energy-storage device includes exposing the energy-storage device to liquid nitrogen vapor.

77. The method of claim 75, wherein cryogenically annealing includes lowering the temperature of the energy-storage device to a near cryogenic temperature, then raising the temperature to a near deposition temperature, and then cooling the energy-storage device to an ambient temperature.

78. The method of claim 77, the lowering, raising, and cooling steps are repeated.

79. The method of claim 77, wherein the lowering, raising, and cooling steps are repeated less than six times.

80. The method of claim 74, wherein the device is a thin-film lithium battery.

81. A method of fabricating a solid-state energy-storage device, comprising:
providing a substrate;
depositing a first film layer on the substrate by a process that includes simultaneously:
(a) depositing a first material to a location on the substrate, and
(b) supplying energized ions of a second material different than the first material directed towards the first material to supply energy thereto and assisting growth of crystalline structure of the film layer during the deposition of the first material on the substrate;
forming an electrolyte second layer on the first layer; and
forming a third layer on the second layer,
wherein the substrate has a thermal degradation temperature of less than 700 degrees;
wherein the first layer is a first film,
wherein the first material is a first electrode material deposited using a deposition source;
wherein the supplying of the energized second material includes supplying particles energized above about 5 eV from a second source such that the particles provide energy to the first electrode material to deposit the first electrode material into a highly ordered crystal film;
wherein the electrolyte second layer is an electrolyte second film formed so as to be in contact with the first film;
wherein the third layer is a film that includes a second electrode material that includes an intercalation material; and
wherein the substrate is not subjected to a high temperature anneal.

82. The method of claim 81, wherein providing the substrate includes providing a substrate having a seed film thereon.

83. The method of claim 81, wherein supplying the energized second material includes focusing a beam of the ions at the location on the substrate.

84. The method of claim 81, wherein supplying the energized second material includes supplying a non-focused beam of the ions.

85. The method of claim 81, wherein supplying the energized second material includes controlling stoichiometry of a growing film of first material.

86. The method of claim 81, wherein at least the depositing of the first film using chemical vapor deposition to direct the first material toward the substrate.

87. The method of claim 81, wherein at least the forming of the electrolyte second film includes using chemical vapor deposition to direct electrolyte material toward the substrate.

88. The method of claim 81, wherein at least the forming of the third film includes using chemical vapor deposition to direct third film material toward the substrate.

89. The method of claim 81, wherein the device is a thin-film lithium battery.

90. A method of fabricating a solid-state energy-storage device, comprising:
providing a substrate;
forming a seed film on the substrate;
depositing a first film layer on the seed film by a process that includes simultaneously:
(a) depositing a first material to a location on the substrate, and
(b) supplying energized ions of a second material different than the first material directed towards the first material to supply energy thereto and assisting growth of crystalline structure of the film layer during the deposition of the first material on the substrate;
forming an electrolyte second layer on the first layer; and
forming a third layer on the second layer, wherein providing the substrate includes providing a substrate having a first contact layer on the substrate.

91. An apparatus comprising:

means for providing a substrate;

means for forming a first seed film on the substrate;

means for forming a first film on the seed film by:
  (a) depositing a first material to a location on the first seed film, and
  (b) supplying a second material different than the first material adjacent the location to control growth of a crystalline structure of the first material at the location;

means for forming an electrolyte second film on the first film; and means for forming a third film on the electrolyte second film.

92. The apparatus of claim 91, wherein the means for forming the third film includes means for forming a second seed film on a surface of the electrolyte second film and thereafter forming the third film on the second seed film.

93. The apparatus of claim 92, wherein the third film includes a lithium intercalation material, and wherein the means for forming the second seed film includes means for depositing an amorphous seed material to diminish undesirable growth structures of the lithium intercalation material of the third film.

94. The apparatus of claim 92, wherein the third film includes a lithium intercalation material, and wherein the means for forming the second seed film includes means for depositing a nanocrystalline seed material with fine grains to diminish undesirable growth structures of the lithium intercalation material of the third film.

95. The apparatus of claim 92, wherein the means for forming the second seed film includes means for depositing an electrically conductive seed material.

96. The apparatus of claim 95, wherein the means for depositing seed material of the second seed film includes means for depositing a seed material comprising one or more of Ta and TaN.

97. The apparatus of claim 95, wherein the means for depositing seed material of the second seed film includes means for depositing a seed material comprising one or more of Cr, and CrN.

98. The apparatus of claim 95, wherein the means for depositing seed material of the second seed film includes means for depositing a seed material comprising one or more of W and WN.

99. The apparatus of claim 95, wherein the means for depositing seed material of the second seed film includes means for depositing a seed material comprising one or more of Ru, and RuN.

100. The apparatus of claim 92, wherein the means for forming the seed film includes means for depositing a seed material having a surface free energy that is higher than a surface free energy of the first film.

101. The apparatus of claim 92, wherein the first film includes a lithium intercalation material, and wherein the means for forming the seed film includes means for depositing an amorphous seed material to diminish undesirable growth structures of the lithium intercalation material of the first film.

102. The apparatus of claim 92, wherein the first film includes a lithium intercalation material, and wherein the means for forming the seed film includes means for depositing a nanocrystalline seed material with fine grains to diminish undesirable growth structures of the lithium intercalation material of the first film.

103. The apparatus of claim 102, wherein the means for depositing seed material of the first seed film includes means for depositing a seed material comprising one or more of Ta, TaN, Cr, and CrN.

104. The apparatus of claim 102, wherein the means for depositing seed material of the first seed film includes means for depositing a seed material comprising one or more of W, WN, Ru, and RuN.

105. The apparatus of claim 92, wherein the means for forming the first seed film includes means for depositing an electrically conductive seed material.

106. The apparatus of claim 92, wherein the device is a thin-film lithium battery.

107. The apparatus of claim 91, wherein means for forming the second seed film includes depositing a seed material having a surface free energy that is higher than a surface free energy of the third film.

* * * * *

UNITED STATES PATENT AND TRADEMARK OFFICE
CERTIFICATE OF CORRECTION

PATENT NO. : 6,962,613 B2
DATED : November 8, 2005
INVENTOR(S) : Mark L. Jenson

It is certified that error appears in the above-identified patent and that said Letters Patent is hereby corrected as shown below:

Column 55,
Line 66, insert -- includes -- after "film".

Column 56,
Line 7, insert -- wherein -- after ",".

Column 57,
Line 61, insert -- includes -- after "film".

Column 59,
Line 55, insert -- wherein -- after ",".

Column 60,
Line 10, insert -- Celsius -- after "degrees".
Line 40, insert -- includes -- after "film".

Signed and Sealed this

Twenty-fifth Day of April, 2006

JON W. DUDAS
*Director of the United States Patent and Trademark Office*